(12) United States Patent
Fraser

(10) Patent No.: US 7,160,694 B2
(45) Date of Patent: Jan. 9, 2007

(54) NUCLEIC ACIDS ENCODING TANGO405 AND FUNCTIONAL FRAGMENTS AND USES THEREOF

(75) Inventor: Christopher C. Fraser, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/766,511

(22) Filed: Jan. 19, 2001

(65) Prior Publication Data

US 2003/0170621 A1 Sep. 11, 2003

Related U.S. Application Data

(63) Continuation-in-part of application No. 09/578,063, filed on May 24, 2000, now Pat. No. 6,764,677, which is a continuation-in-part of application No. 09/333,159, filed on Jun. 14, 1999, now Pat. No. 7,033,780, said application No. 09/766,511 is a continuation-in-part of application No. 09/596,194, filed on Jun. 16, 2000, now abandoned, which is a continuation-in-part of application No. 09/342,364, filed on Jun. 29, 1999, now abandoned, said application No. 09/766,511 is a continuation-in-part of application No. 09/608,452, filed on Jun. 30, 2000, now abandoned, which is a continuation-in-part of application No. 09/393,996, filed on Sep. 10, 1999, now abandoned, said application No. 09/766,511 is a continuation-in-part of application No. 09/345,680, filed on Jun. 30, 1999, now abandoned.

(51) Int. Cl.
*C12P 21/06* (2006.01)

(52) U.S. Cl. ............... 435/69.1; 435/252.3; 435/320.1; 435/325; 435/6; 536/23.5

(58) Field of Classification Search .............. 435/69.1, 435/252.3, 320.1, 325, 6; 536/23.5; 530/350
See application file for complete search history.

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 5,594,120 A | 1/1997 | Brenner et al. |
| 6,046,158 A * | 4/2000 | Ariizumi et al. ............... 514/2 |

FOREIGN PATENT DOCUMENTS

| WO | WO 87/07907 A1 | 12/1987 |
|---|---|---|

OTHER PUBLICATIONS

NCI-CGAP, Database on Genbank, EST AI184538, Nov. 10, 1998.
Hillier et al., Database on Genbank, EST AA176796, Mar. 9, 1998.
Hillier et al., Database on Genbank, EST AA173251, Mar. 9, 1998.
NCI-CGAP, Database on Genbank, EST AI380446, Mar. 30, 1999.
NCI-CGAP, Database on Genbank, EST AI304312, Feb. 1, 1999.
Hillier et al., Database on Genbank, EST AA234670, Aug. 7, 1997.
Marra et al., Database on Genbank, EST AA021860, Jan. 21, 1997.
Hudson, T., Database on Genbank, STS G07283, Oct. 19, 1995.
Yang et al., Cloning and Characterization of a Novel Matrix Metalloproteinase (MMP), CMMP, from chicken embryo fibroblasts. The Journal of Biological Chemistry, 1998, vol. 273, No. 28, pp. 17893-17900, see accession No. AF062392.
Saus et al., The Complete Primary Structure of Human Matrix Metalloproteinase-3. The Journal of Biological Chemistry. 1998, vol. 263, No. 14, pp. 6742-6745, see accession No. J03209.
GenBank, U.S. National Library of Medicine, (Bethesda, MD, USA), Accession No. AF148882.
Pharmacia Biotech Catalog, 1996, pp. 107, 110-117, 139, 163-165.
Aragane et al., "Involvement of Dectin-2 in Ultraviolet Radiation-Induced Tolerance" The Journal of Immunology 171:3801-3807, 2003.
Kanazawa et al., "Molecular Cloning of Human Dectin-2" The Journal of Investigative Dermatology pp. 1522-1524, 2004.
Fernandes et al., "Characterization of a Novel Receptor That Maps Near the Natural Killer Gene Complex: Demonstration of Carbohydrate Binding and Expression in Hematopoietic Cells" Cancer Research 59:2709-2717, 1999.
Ariizumi, Kiyoshi, University of Texas Southwestern Faculty Profile abstract. Retrieved from the internet on Oct. 19, 2005. URL: http://utsouthwestern.edu/findfac/research/0,2357,10221,00.html/>.

* cited by examiner

*Primary Examiner*—Lorraine Spector
*Assistant Examiner*—Dong Jiang
(74) *Attorney, Agent, or Firm*—Millennium Pharmaceuticals Inc.

(57) ABSTRACT

The invention provides isolated nucleic acids encoding a variety of proteins having diagnostic, preventive, therapeutic, and other uses. These nucleic and proteins are useful for diagnosis, prevention, and therapy of a number of human and other animal disorders. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening, and therapeutic methods using compositions of the invention are also provided. The nucleic acids and polypeptides of the present invention are useful as modulating agents in regulating a variety of cellular processes.

11 Claims, 39 Drawing Sheets

```
Hum.  MRRQPAKVAALLLGLLLECTEAKKHCWYFEGLYPTYICRSYEDCCGSRCCVRALSIQRLWYFWFLLMMG   : 70
      :: :  ::::::::::::: ::::::::::::::::::::::::::::::::::::::::::::::::
Mur.  MGRRLGRVAALLLGLLVECTEAKKHCWYFEGLYPTYICRSYEDCCGSRCCVRALSIQRLWYFWFLLMMG   : 70

Hum.  VLFCCGAGFFIRRMYPPPLIEEPAFNVSYTRQPPNPGPGAQQPGPPYTDPGGPGMNPVGNSMAMAFQV    : 140
      ::::::::::::::::::::::::: :::::::::::::::: :  ::::::::::::::::::::::
Mur.  VLFCCGAGFFIRRMYPPPLIEEPTFNVSYTRQPPNPAPGAQQMGPPYTDPGGPGMNPVGNTMAMAFQV    : 140

Hum.  PPNSPQGSVACPPPPAYCNTPPPPYEQVVKAK  : 170
      ::::: :   :  :  :::::::::::::: :
Mur.  QPNSPHGGTTYPPPPSYCNTPPPPYEQVVKDK  : 170
```

Fig. 1A

```
slit  MRGVGWQMLSLSLGLVLA------ILNKVAPQACPAQCS-CSGSTVDCHGLALRSVPRNIPRNTERLDLNG
          .: .   :  : ::.:             .:.::  .::.  :. :: ::::   :    ::::
325   MCGLQFSLPCLRLFLVVTCYLLLLHK-EILGCSSVCQLCTGRQINCRNLGLSSIPKNFPESTVFLYLTG slit  NNITRITKTDFAGLRHLRVLQLMENKISTIERGAFQDLKELERLRLNRNHLQLFPELLFLGTAKLYRLDL
      :::  : :::::..:: ::::  ::  ::::::::.:::::::::::::::::.::::::::::::::
325   NNISYINESELTGLHSLVALYLDNSNILYVYPKAFVQLR------HLY--FLFLNNFIKRLDslit  SENQIQAIPRKAFRGAVDIKNLQLDYNQISCIEDGAFRALRDLEVLTLNNNNITRLSVASFNHMPKLRTF
            :  ::: :.: :::  :: :::: :::  :.::: :::. :::::::.:::::::.::.::::
325   ----PGI----FKGLLNRNLYLQYNQVSFVPRGVFNDLVSVQYLNLQRNRLTVLGSGTF------ slit  RLHSNNLYCDCHLAWLSDWLRQRPRVGLYTQCMGPSHLRGHNVAEVQKREFVCSGHQSFMAPSCSVLHCP
                                              ::
325   ------------------------------------VGM------VA-------------

Fig. 2B
```

```
            280          290         300         310         320         330         340
Slit  AACTCSNNIVDCRGKGLTEIPTNLPETITEIRLEQNTIKVIPPGAFSPYKKLRRIDLSNNQISELAPDAF
                                                         ::  :: ::::::  :
325   ---------------------------------------------------LRILDLSNNNI-------
                                                                    190

350         360         370         380         390         400         410
Slit  QGLRSLNSLVLYGNKITELPKSLFEGLFSLQLLLNANKINCLRVDAFQDLHNLNLLSLYDNKLQTIAKG
        ::                                              .:::  :::  :
325   --LR----------------------------------------ISE---SGFQHLENLACL------
                                                                     200

420         430         440         450         460         470         480
Slit  TFSPLRAIQTMHLAQNPFICDCHLKWLADYLHTNPIETSGARCTSPRRLANKRIGQIKSKKFRCSAKEQY
                                ::  :
325   ------------------------YLGSN----------------------------------------
                                210

490         500         510         520         530         540         550
Slit  FIPGTEDYRSKLSGDCFADLACPEKCRCREGTTVDCSNQKLNKIPEHIPQYTAELRLNNNEFTVLEATGIF
                                            :::::                    ::   ::
325   ---------------------------------NLTKVP-----------------------SNAFEVLKS---
                                        220
```

Fig. 2C

```
slit  KKLPQLRKINFSNNKITDIEEGAFEGASGVNEILLTSNRLENVQHKMFKGLESLKTLMLRSNRITCVGND
      560       570       580       590       600       610       620
325   -----LRRLSLSHNPIEAIQ---PFA-------------------FKGLANLEYLLLKNSRIRNVTRD
           230                                    250       260       270 slit  SFIGLSSVRLLSLYDNQITTVAPGAFDTLHSLSTNLLANPFNCNCYLAWLGEWLRKKRIVTGNPRCQKP
      630       640       650       660       670       680       690
325   GFSGINNLKHLILSHND--------------------LEN----------------------------
           280                            290 slit  YFLKEIPIQDVAIQDFTCDDGNDDNSCSPLSRCPTECTCLDTVVRCSNKGLKVLPKGIPRDVTELYLDGN
      700       710       720       730       740       750       760
325   --------------------------------------------------------------LNSD slit  QFTLVPKELSNYKHLTLIDLSNNRISTLSNQSFSNM-TQLLTLILSYNRLRCIPPRTFDGLKSLRLLSLH
      770       780       790       800       810       820       830
325   -----KNLIYLKLDRNRIISIDNDTFENMGASLKILNLSFNNLTALHPRV---LKPL-----
           300       310       320       330       340 slit  TFSLL----------------------------------------------------
325   ----------------------------------------------------------
```

Fig. 2D

```
              840        850        860        870        880        890        900
Slit   GNDISVVPEGAFNDLSALSHLAIGANPLYCDCNMQWLSDWVKSEYKEPGIARCAGPGEMADKLLLTTPSK
            : :: ..: .. :.: : : ::: .:.: : :: .  :
325    ------------------------SSLIHLQANSNPWECNCKLLLGIRDWLAS---------------
                              350        360        370

910        920        930        940        950        960        970
Slit   KFTCQGPVDVNILAKCNPCLSNPCKNDGTCNSDPVDFYRCTCPYGFKGQDCDVPIHACISNPCKHGGTCH
         :    :       ::  ::::::::: ::::::   ::: :  :: :: :: :::::::
325    ----SAITLNI-------------------Y------------CQNP-----------PSMRG------
          380                                                  390

980        990       1000       1010       1020       1030       1040
Slit   LKEGEEDGFWCICADGFEGENCEVNVDDCEDNDCENNSTCVDGINNYTCLCPPEYTGELCEEKLDFCAQD
         : . : :   :.:.                :. :::
325    ----RALRYI------------------NITNCV-----------------------------------
          400

1050       1060       1070       1080       1090       1100       1110
Slit   LNPCQHDSKCILTPKGFKCDCTPGYVGEHCDIDFDDCQDNKCKNGAHCTDAVNGYTCICPEGYSGLFCEF
                                             : : ::
325    ------------------------------------TSSIN-----------------------------
                                          410
```

Fig. 2E

```
              1120       1130       1140       1150       1160       1170       1180
              .    :    .    :    .    :    .    :    .    :    .    :    .    :
Slit  SPPMVLPRTSPCDNFDCQNGAQCIVRINEPICQCLPGYQGEKCEKLVSVNFINKESYLQIPSAKVRPQTN
325   ----VSRAWA----------------VVK-------------------------SPHIHKTTALMMAWHKV---
                  420                                                  430

1190       1200       1210       1220       1230       1240       1250
              .    :    .    :    .    :    .    :    .    :    .    :    .    :
Slit  ITLQIATDEDSGILLYKGDKDHIAVELYRGRVRASYDTGSHPASAIYSVETINDGNFHIVELLALDQSLS
325   TTNGSP------LENTETENIT----FWERIPTS--------PAGRFFQENAFGNP-LETTAVLPVQIQLT
          440                450                      470               480

1260       1270       1280       1290       1300       1310       1320
              .    :    .    :    .    :    .    :    .    :    .    :    .    :
Slit  LSVDGGNPKIITNLSKQSTLNFDSPLYVGGMPGKSNVASLRQAPGQNGTSFHGCIRNLYINSELQDFQKV
325   TSV-------TLNLEKNSALPNDAA----SMSGKTSLI------------------CT-------QEVEKL
      490             500                  510                               520

1330       1340       1350       1360       1370       1380       1390
              .    :    .    :    .    :    .    :    .    :    .    :    .    :
Slit  PMQTGILPGCEPCHKKVCAHGTCQPSSQAGFTCECQEGWMGPLCDQRTNDPCLGNKCVHGTCLPINAFSY
325   NEAFDILLA----------------------------F-----------------------------FIL
      530
```

*Fig. 2F*

```
              1400       1410       1420       1430       1440       1450       1460
slit  SCKCLEGHGGVLCDEEEDLFNPCQAIKCKHGKCRLSGLGQPYCECSSGYTGDSCDREISCRGERIRDYYQ
         ::            ::         .:        .:       ..       ..      .:
325   AC------VL-----IIFLIYKVVQFKQ---KLKA-----------SENS------RENRL-EYY-
              540             550              560                 570

1470       1480       1490       1500       1510       1520
slit  KQQGYAACQTTK-KVSRLECRGGCAGGQCCGPLRSKRRKYSFECTDGSSFVDEVEKVVKCGCTRCVS
         ::       ..        ..         ..         ..        ..       ..
325   ---SF--YQSARYNVTASICNTSPNSLESPGLEQIRLHK-------QIVPENEAQVI-LFEHSAL
              580             590              600           610     620
```

Fig. 2G

```
slit  CAGAGCAGGTGGAGAGGCGGGTGGGAGAGGCGTGTGCCTGAGTGGGCTCTACTGCCTTGTTCCATATTATT
              10        20        30        40        50        60        70
325   ---------------------------------------------------------------------- slit  TTGTGCACATTTCCCTGGCACTCTGGGTTGCTAGCCCCGCCCGGGCCTCAGACACTGCGCGGT
              80        90       100       110       120       130       140
325   -------------------------------------------------------------- slit  TCCCCTCGGAGCAGCAAGCTAAAGAAAGCCCCCAGTGCCGGGCGAGGAAGAGGCGGGGAAAGATGCGC
             150       160       170       180       190       200       210
325   ----------------------------------------------------------------- slit  GGCGTTGGCTGGCAGATGCTGTCCCTGTCGCTGGGGTTAGTGCTGGCGATCCTGAACAAGGTGGCACCGC
             220       230       240       250       260       270       280
325   -------------------------------------------GTCG------:::------------ACC---
                                                                       :::
```

Fig. 2H-1

```
Slit  AGGCGTGCCCGGGCGCAGTGCTCTTGCTCGGGCCAGCAGCACAGTGGACTGTGTCACGGGCTGGCGCTGCCGCAGCGT
           290       300       310       320       330       340       350
325   ----------------------------------------------------------------------CACG---CGT
                                                                             10

Slit  GCCCAGGAATATCCCCCGCAAACACCGAGAGACTGGATTAAATGGAAATAACATCACAAGAATTACGAAG
           360       370       380       390       400       410       420
325   --CCGGAAATGTC--------------------------------------------------------
         20

Slit  ACAGATTTGCTGGTCTTAGACATCTAAGAGTTCTTCAGCTTATGGAGAATAAGATTAGCACCATTGAAA
           430       440       450       460       470       480       490
325   ----------------------------GTTCTTCAGATTTAAAAAGAAAA------------------
                                       30              40

Slit  GAGGAGCATTCCAGGATCTTAAAGAACTAGAGAGACTGCGTTTAAACAGAAATCACCTTCAGCTGTTTCC
           500       510       520       530       540       550       560
325   ----CTGAATC------AGCT-GAGTG---------TTAAT---AATACG---------AATTTCC
           60              70                    80
```

Fig. 2H-2

```
slit  TGAGTTGCTGTGTTCTTGGACTGCGAAGCTATACAGGCTTGATCTCAGTGAAAACCAAATTCAGGCAATC
       :    ::::::: :  ::  ::: ::::::::.:              :::  :::::::::::::::
325   T------TTTCTTG---C--CAATTCTGATCTGA-----ACAGA-AAATCCAAGAACAGG---------
              90             100          110         120        130 slit  CCAAGGAAAGCTTTCCGTGGGGCAGTTGACACATAAAAAATTTGCAACTGGATTACAACCAGATCAGCTGTA
                                       :: :: ::     :::   ::::::::  ::    : :
325   ------------------------------GATATGTG----TGGATTACA-----------------GTT
                                          140                              150 slit  TTGAAGATGGGGCATTCAGGGCTCTCCGGGACCTGGAAGTGCTCACTCTCAACATAACAACATTACTAG
      : :               :::: ::     :::   :::               :  
325   TT----------------CTCT----GCC-T---TGC----CTACGA----------------------
                          160           170 slit  ACTTTCTGTGGCAAGTTTCAACCATATGCCTAAACTTAGGACTTTTCGACTGCATTCAAACAACCTGTAT
                        : :::: :: ::                                  ::
325   --------------------TCTTT------------------------------------------AT
                          190                                            200
```

Fig. 2H-3

```
Slit  TGTGACTGCCACCTGGCCTCTCCGACTGGCTTCGCCAAAGGCCTCGGGTTGGTCTGTACACTCAGT
      :: ::: :::::::  :   ::  :   ::   ::   ::::::: ::  :: :: :  :: :: :
325   TATTACT-CCACAAAG----------------AAATAC------TTGGA-TGTTCG-TC--T
              210                    220                230

Slit  GTATGGGCCCCTCCCACCTGAGAGGCCATAATGTAGCCGAGGTTCAAAAACGAGAATTTGTCTGCAGTGG
       ::::::         ::        :::                    ::::::: ::: :: :
325   GTTTG------TC------------AGC----------------------TCTGCACTGG
      240                                                250

Slit  TCACCAGTCATTTATGGCTTCCTTCTGTAGTGTTTGCACTGCCCTGCCGCCTGTACCTGTAGCAACAAT
            :  ::  :::: :                 : :::        ::: ::  :::
325   G----AGACAAATTA-----------------ACTGCC----------GTAACTTAGGC-----
            260                      270                280

Slit  ATCGTAGACTGTCGTGGGAAAGGTCTCACTGAGAGATCCCCACAAATCTTCCAGAGACCACCATCACAGAAATAC
          :::: :   ::::    :  :         ::: ::: :::::  :::::: :: :   ::::: :
325   ------CTTTCGAG---TATTC---CTAAGA----------ATTTTCCTGAAAA--GT-ACAGTTTTTC
             290            300              310                 320
```

Fig. 2H-4

```
         1130      1140      1150      1160      1170      1180      1190
slit GTTTGGAACAGAACACAATCAAAGTCATCCCTCCTGGAGCTTTCTCACCATATAAAAAGCTTAGACGAAT
     : :: : : : :: :                      : : : : :  : : : :: :  : :: :: :
 325 ---TGTATCTGA-----------------------CTGGGAATAATATATCTTATATAAATGAAAGT-GAAT
        330                                 340       350       360       370

1200      1210      1220      1230      1240      1250      1260
slit TGACCTGAGCAATAATCAGATCTCTGAACTTGCACCAGATGCTTTCCAAGGACTACGCTCTCTGAATTCA
     : : : :                                                 : : : : :
 325 TAAC-----------------------------------------------AGGACTTC------ATTCT
        390                                                  380

1270      1280      1290      1300      1310      1320      1330
slit CTTGTCCTCTATGGAAATAAAATCACAGAACTCCCCAAAAGTTTATTGAAGGACTGTTTTCCTTACAGC
     : : : :: :             : : :               : : : :: :  : : :: :: :
 325 CTTGT-----------------AGC---------------ATTGTATTTGGA------TAATTCTAACA---
        390                                       400            410       420

1340      1350      1360      1370      1380      1390      1400
slit TCCTATTATTGAATGCCAACAAGATAAACTGCCTTCGGGTAGATGCTTTTCAGGATCTCCACAACTTGAA
     :  : :: :  : : : :     :           : : :: :         : :   :: :: : :
 325 TTCTGTATGTATAT-CCAAAA--------GCCTTTG------TTCAATTGAGG------CATCTATAT
        430            440              450                        460
```

Fig. 2H-5

```
slit  CCTTCTCTCCCTATATGACAACAAGCTTCAGACCATGCCAAGGGGACCTTTTCACCTCTTCGGGCCATT
      :::: : ::::::::: ::                                  ::::: ::       :       T
325   T-TTCTATTTCTAAATAA------------------------------------TTTCA------------T
      470                 480                              490 slit  CAAACTATGCATTTGGCCCAGAACCCCTTTATTTGTGACTGCCATCTCAAGTGGCTAGCGGATTATCTCC
      ::::::  ::   :::::::: ::       : ::::::                 ::: ::
325   CAAAC---GC-TTAGATCCTGGA-------ATATTT--------------------AAGGGACTTT----TAAATCTTC
      500                         510                               520         530 slit  ATACCAACCCGATTGAGACCAGTGGTGCCCGTTGCACCAGCCCCCGCCCTGGCAAACAAAAGAATTGG
      :: :                                                                  ATTTATATTT
325   GTA-------------------------------------------------------------------ATTTATATTT
      540                                                                    550 slit  ACAGATCAAAAGCAAGAAATTCCGTTGTTCAGCTAAAGAACAGTATTTCATTCCAGGTACAGAAGATTAT
      :::: ::  :::: :::::   :::::: ::    ::    ::    :::::    ::::::  :
325   ACAGT--ATAATCAGGTA--TCTTTTGTTC--CGAGAGG--AGTATTTAAT---------------------
      560               570            580         590
```

Fig. 2H-6

```
            1690      1700      1710      1720      1730      1740      1750
Slit  CGATCAAATTAAGTGTGGAGACTGCTGCTTTGCGGATCTGGCTTGCCCTGAAAAGTGTCGCTGTGAAGGAACCA
          :::::::.::                     :::::::
325   -GATCTAGTTT---------------------CAGTTCAG-----------------------------------
      600                              610

1760      1770      1780      1790      1800      1810      1820
Slit  CAGTAGATTGCTCTAATCAAAAGCTCAACAAAATCCCGGAGCACACATTCCCCAGTACACTGCAGAGTTGCG
      .:::  :::::::                  ::::  :::  ::: :::       :::   :::
325   -------TACTTAAATCTA------------CAAA-----GGAA-------TCGCCT----CACTG--------
             620                     630          640

1830      1840      1850      1860      1870      1880      1890
Slit  TCTCAATAATAATGAATTTACCGTGTTGGAAGCCACAGGAATCTTTAAGAAACTTCCTCAATTACGTAAA
              .::  :::::::             :::              ::::
325   --------TCC---TTGGGAG----------TGG----------------TACCT-------------------
              650                     660

1900      1910      1920      1930      1940      1950      1960
Slit  ATAAAACTTTAGCAACAATAAGATCACAGATATTGAGGAGGAGCATTTGAAGGAGCATCTGGTGTGTAAATG
                          ::::  .:::      :::                    :::
325   ---------------------TTGTTGGTATGGTTGCT-------------------CTTCGG-----------
                           670                                  680
```

Fig. 2H-7

```
            1970      1980      1990      2000      2010      2020      2030
slit  AAATACTTCTTACGAGTAATCGTTTGGAAAATGTGCAGCATAAGATGTTCAAGGGATTGGAAAGCCTCAA
          :::::::       ::  :::::                                         ::
325   --ATACTT-----GATTTATC-----------------------------------------------A
              690

2040      2050      2060      2070      2080      2090      2100
slit  AACTTTGATGTTGAGAAGCAATCGAATAACCTGTGTGGGGAATGACAGTTTCATAGGACTCAGTTCTGTG
           :::     ::::: :: :::::::::::    :::  :: :::::  ::::::::::
325   AAC-----------AATAAC---ATTTGAGGATATCAGAATCAG----------------------
      700                       710       720

2110      2120      2130      2140      2150      2160      2170
slit  CGTTTGCTTTCTTTGTATGATAATCAAATTACTACAGTTGCACCAGGGCATTTGATACTCTCCATTCTT
         :::::                                                              
325   ----GCTTTC-----------------------------------------------------------
          730

2180      2190      2200      2210      2220      2230      2240
slit  TATCTACTCTAAAACCTCTTGGCCAATCCTTTTAACTGCTAACTGCTACCTGGCTTGGTTGGGAGAGTGGCT
         :: ::::::   :::::::  :::::::                     :: :::::::        :
325   ------AACATCTTGA--AAACCTT-------------------------GCTTGTTTGTAT-----T
             740         750                                760
```

Fig. 2H-8

```
slit  GAGAAAGAAGAGAATTGTCACGGGAAATCCTAGAGTGTCAAAAACCATACTTCCTGAAAGAAATACCCATC
      :::::::::..::::::.:::      ..:::::...:::::::      :::::..:
 325  TAGGAAGTAATAATTTA--ACAAAAGTACC----ATCAAATGCCTTT--------GAAGTAC---------
           780         790            800            810 slit  CAGGATGTGGCCATTCAGGACTTCACTTGTGATGACGGAAATGATGACAATAGTTGCTCCCCACTTTCTC
                   .::::::.:::::..                     ::..:::::::
 325  --------TTAAAAGTCTT-----------------AGAAGACTTT---------CTTTGTCTC------
                820                          830              840 slit  GCTGTCCTACTGAATGTACTTGCTTGGATACAGTCGTCCGATGTAGCAACAAGGGTTTGAAGGTCTTGCC
      ::            ::        ::..   :.      :: ::       :::::::..
 325  ATAATCCTATTGAA---------GCA---ATACAG-C--CCTTTG---CA----------TTTAAGGACTTGCC
            850            860        870                   880         890 slit  GAAAGGTATTCCAAGAGATGTCACAGAGTTGTATCTGGATGGAAACCAATTTACACTGGTTCCCAAGGAA
                                                    :::  :::    :::
 325  AA-------------------------------------------TCTGGA---ATACC---TCC-----
                                                         900
```

Fig. 2H-9

```
                   2530      2540      2550      2560      2570      2580      2590
slit CTCTCCAACTACAAACATTAACACTTATAGACTTAAGTAACAACAGAATAAGCACGCTTTCTAATCAGA
     :::.  :  .:::::..  :  ::::::..:  .:::::::  .::::..::  :: .:::::..
325  ---TCCTGAAAAATTCAAGAA-----TTAGGA----ATGTTACTA-GGGATGGG--------TTTAGT--GG
                910       920       930        940         950

2600      2610      2620      2630      2640      2650      2660
slit GCTTCAGCAACATGACCCAGCTCCTCACCTTAATTCTTAGTTACAACCGTCTGAGATGTATTCCTCCTCG
     : :: .:.::..::    ::.::::..    ::::::..:::::: :.   ::::    :::
325  AATTAATAATCTTAA----------ACATTTGATCTTAA-----------GTCA-TAATGA--------
        960       970          980        990

2670      2680      2690      2700      2710      2720      2730
slit CACCTTTGATGGATTAAAGTCTCTCTTCGATTACTTCTCTACATGGAAATGACATTTCTGTTGTGCCTGAA
     ::  .::::::: ::::::.::   .::  ::  .::   ::.:: :::: :.:::: ::.::::::
325  -TTTAGAGAATTTAAAT----TCTGACACATTCAGT--TTGTTAAAGA-ATT--TAATTTACCTTAA
          1000        1010        1020         1030         1040       1050

2740      2750      2760      2770      2780      2790      2800
slit GGTGCTTTCAATGATCTTTCTGCATTATCACATCTAGCAATTGGAGCCAACCCTCTCTTTACTGTGATTGTA
     :  ::::::. ::..  :: ::::::      ::::::         ::::::::: ::  .:::.
325  G-----TTAGATAGAA---ACAGAATAAT-------TAGCATT---------------GATAATGAT
              1060           1070              1080
```

Fig. 2H-10

```
slit  ACATGCAGTGGTTATCCGACTGGGTGAAGTCGGAATATAAGGAGCCTGGAATTGCTCGTCGTTGTGCTGGTCC
      2810      2820      2830      2840      2850      2860      2870
      : :::                                      :  :::: ::::: :
325   ACAT------------------------------------TTGAAAATATGGGAGCAT----------CTTTGAA--GATCC
      1090                                          1100      1110              1120 slit  TGGAGAAATGGCAGATAAACTTTTACTCCACAACTCCCTCCAAAAAATTACCTGTCAAGGTCCTGTGGAT
      2880      2890      2900      2910      2920      2930      2940
                                                       ::: ::::::::
325   T-------------------------------------------------TAATCTGTCAT---------
      1130 slit  GTCAATATTCTAGCTAAGTGTAACCCCTGCCTATCAAATCCGTGTAAAAATGATGGCACATGTAATAGTG
      2950      2960      2970      2980      2990      3000      3010
           ::::       ::                              :::::  :::::          ::
325   -TTAATAAATCTTACA---------------------------GCCTTGC--ATCCAAG----------G
            1140                                      1150      1160 slit  ATCCAGTTGACTTTTACCGATGCACCTGTCCATATGGTTTCAAGGGGCAGGACTGTGATGTCCCAATTCA
      3020      3030      3040      3050      3060      3070      3080
           ::::        :::             ::::::                          ::::::
325   GTCC--------TTAAGCCGT------TGTC---------TTCATTG-------TTCATTG----ATTCA
      1170              1180                                             1190
```

Fig. 2H-11

```
          3090      3100      3110      3120      3130      3140      3150
slit TGCCTGCATCAGTAACCCATGTAAACATGGAGGAACTTGCCACTTAAAGGAAGGAGAAGATGGATTC
     :  :::::  :::::  :  :::    :::  :  :::      ::     ::  :: ::: :
325  T------CTTCAGG------CAAATT------------CTAATC-CTT-----GGGAATGTAACTGCAAAC
              1200              1210              1220          1230

3160      3170      3180      3190      3200      3210      3220
slit TGGTGTATTTGTGCTGATGGATTTGAAGGAGAAATTGTGAAGTCAACGTTGATGATTGTGAAGATAATG
     :  ::  ::    :::: ::                :::::              :::::       :
325  T------TTTGGGC------------------------CTTCGA----------------------G
              1240

3230      3240      3250      3260      3270      3280      3290
slit ACTGTGAAAATAATTCTACACATGTGTCGATGGCATTAATAACTACACATGCCTTTGCCCACCTGAGTATAC
     ::::                  :::::::::       :::::  :::::       :::::
325  ACTG------------------TAGCAT--------CTTCA---GCCATTAC--------------
     1250                  1260          1270

3300      3310      3320      3330      3340      3350      3360
slit AGGTGAGTTGTGTGAGGAGAAGCTGGACTTCTGTGCCCCAGGACCCCTGAACCCCTGCCAGCACGATTCAAAG
                       ::::::::::::  :::          :::::::
325  ------------------TCTAAACATCTATT----GTCAGAATCCCC--------------------
                       1280                1290
```

Fig. 2H-12

```
slit  TGCATCCTAACTCCAAAGGGATTCAAATGTGACTGCACACCAGGGTACGTAGGTGAACACTGCGACATCG
      :: :::::.:                       :::::.::           :::::.:
325   --CATCCATGC----------------------GTGGCAGAGCA-----------TTACGTT---------
        3370    3380    3390    3400    3410    3420    3430
        1300                            1310    1320 slit  ATTTTGACGACTGCCAAGACAACAAGTGTAAAAACGGAGCCCACTGCACAGATGCAGTGAACGGCTATAC
      :: :::.:: :  :: :::  ..:::.::::::::.                 :::::.: ::::
325   ATATTAAC-------ATTACAAATTGTGTTA-------------------------CATCTTCA-----ATAA
        3440    3450    3460    3470    3480    3490    3500
        1330            1340    1350                            1360 slit  GTGCATATGCCCCGAAGGTTACAGTGGCTTGTTCTGTGAGTTTTCTCCACCCATGGTCCTCCCCTCGTACC
      ::: ::  :: :: ::.:       : :::::::     .::::::::  :.:::::::.
325   ATGTAT----CCAGAG------CTTGGGCT-GTT----GTAAAATCTCCCTC--ATATTCATCACAAGA--C
        3510    3520    3530    3540    3550    3560    3570
        1370            1380            1390    1400    1410 slit  AGCCCCTGTGATAATTTGATTGTCAGAATGGAGCTCAGTGTATCGTCAGAATAAATGAGCCAATATGTC
      ::: :::: ::  :       :::::::::.     .:::::::::  ::            ::   ::
325   TAC---TGCGCTAAT---GATGGCCTG-------GCATAAAGTAAC--CA------------CAA--ATGGC
        3580    3590    3600    3610    3620    3630    3640
        1420            1430            1440                    1450
```

Fig. 2H-13

```
slit  AGTGTTTGCCTGGCTATCAGGGAGAAAAGTGTGAAAATTGGTTAGTGTGAATTTTATAAACAAAGAGTC
      :::      ::   :: ::::: ::::::                  :::::: :::: ::::::::
325   AGT-----CCT--CT-----GGAAATACTGAGAC-----------TGAGAACATTACTTTCTGGGAA-
      1460         1470               1480          1490         1500 slit  TTATCTTCAGATTCCTTCAGCCAAGGTTCGGCCCTCAGACGAACACATAACACTTCAGATTGCCACAGATGAA
      : :::::::::                   :::   ::   :::::: ::::::::::::::::
325   ---CGAATTCCTAC---------------TTCACCTGCTGGTAGA-TTTTTTCAAGAGAATGCCTTTGGTAA-
         1510                      1520           1530         1540         1550 slit  GACAGCGGGAATCCCTCCTGTATAAGGGTGACAAAGACCATATCGCGGTAGAACTCTATCGGGGGCGTGTTC
      :::          ::: :     ::    :: :::   ::           :::::::
325   -------TCCATTA-----GAGACTA----CA---GCAGTGTTAC-CTGT----GCAAATAC-
             1560              1570         1580         1590 slit  GTGCCAGCTATGACACCGGCTCTCATCCAGCTTCTGCCATTTACAGTGTGGAGACAATGATGGAAA
      :::::::::::::::           ::::::::::::::::::::::::::::::
325   AA-CTTACTA------------CTTCTGTTACCTTGAACT---TGGAAAAAACAGTGCT------
         1600              1610         1620         1630
```

Fig. 2H-14

```
             3930      3940      3950      3960      3970      3980      3990
slit CTTCCACATTGTGGAACTACTTGCCTTGGATCAGAGTCTCTCTTTGTCCGTGGATGGTGGGAACCCCAAA
     ::::: ..:::..:::::                              ..::::::
325  CTACCG---AATGATGCTGCTT-----------------------------CAATGTC-----AGGGAA---
     1640      1650                                      1660

4000      4010      4020      4030      4040      4050      4060
slit ATCATCACTAACTTGTCAAAGCAGTCCACTCTGAATTTTGACTCTCCACTCTATGTAGGAGCATGCCAG
     ::::::..::::: ::::                              ::::: .::::
325  AACATCTCTAATTTGT---------------------ACACAAGAAGTTGA----------------------
     1670      1680                         1690

4070      4080      4090      4100      4110      4120      4130
slit GGAAGAGTAACGTGGCATCTCTGCGCCAGGCCCCTGGGCCAGAACGGAACCAGCTTCCACGGCTGCATCCG
     ::::: .:: :::::                                ::: :.:::  ::::
325  -GAAGTTGAATGAGGCTT------------------------------TTGACATTTTG---CTAGCTT---
     1700      1710                                  1720       1730

4140      4150      4160      4170      4180      4190      4200
slit GAACCTTTACATCAACAGTGAGCTGCAGGACTTCCAGAAGGTGCCGATGCAAACAGGCATTTTGCCTGGC
     :::::: :  :::  :::                     :::                 ::::::
325  -----TTTTCATC----TTAGCTT---------------GTG---TTTTAATCATTTT-----------
             1740                          1750       1760
```

Fig. 2H-15

```
Slit  TGTGAGCCATGCCACAAGAAGGTGTGTGCCCATGCCAGCCCAGCAGCCAGGCTTCACCT
      ::::  ::   :::   ::            ::  ::::  :::::::::::::  :
325   TTTGATC--TAC-----AAAGTTGTT------------------------CAGTTTA----A
      1770           1780                                 1790

Slit  GCGAGTGCCAGGAAGGATGGGGATGGGCCCCTCTGTGACCAACGGACCAATGACCCTTGCCTTGGAAATAA
      :  ::::::  ::::::    ::::                        ::::  ::::::::
325   ACAAAAACTA--AAGG-----------------CATCAGAAAAACT---------------CAAGGAAAAT
      1800                               1810                      1820

Slit  ATGCGTACATGGCACCTGCTTGCCCATCAATGCGTTCTCCTACAGCTGTAAGTGCTTGGAGGGCCATGGA
         ::   ::   ::::::   :::                  :::  ::::::::::::    ::
325   AGACTTGAATA-CTACAGCTT------------------TTATCAGTCAGCAAGGTATA-----ATGTA
      1830       1840                          1850       1860        1870

Slit  GGTGTCCCTCTGTGATGAAGAGGAGGATCTGTTTAACCCATGCCAGGCGATCAAGTGCAAGCACGGGAAGT
      ::    ::  ::  :::               ::                    ::::::    ::
325   ACTG-CCTCAAT-TTG-------------------TAACACTTCCC--------CAAATTCT--CT-AGAAAGT
      1880              1890                      1900           1910
```

Fig. 2H-16

```
slit  GCAGGCTTTCAGGTCTGGGGCAGCCCTACTGTGAATGCAGCAGTGGATACACGGGGACAGCTGTGATCG
         4490      4500      4510      4520      4530      4540      4550
      :::::::           ::::::                       ::::::  ::  ::::::::
325   CCTGGCTT------GGAGCAG------------------------------ATTC------GACTTCA-TAAACA
         1920      1930                                         1940 slit  AGAAATCTCTTGTCGAGGGAAAGGATAAGAGATTATTACCAAAAGCAGCAGGGCTATGCTGCTTGCCAA
         4560      4570      4580      4590      4600      4610      4620
      ::::::  ::     :                              :::  :::::  ::  ::::::
325   AATTGT-TC----C--------TGAAAATGAG------------GCA-CAGGTC-ATTCTTTTTG----A
         1950             1960                     1970      1980 slit  ACAACCAAGAAGGTGTCCCGATTAGAGTGCAGAGGTGTGCAGGAGGGCAGTGCTGTGGACCGCTGA
         4630      4640      4650      4660      4670      4680      4690
      :::  :                                                    ::::::::
325   ACATTC-------------------------------------------------TGCTTTATAACTC---
         1990                                                    2000 slit  GGAGCAAGCGGGGGAAATACTCTTTCGAATGCACTGACGGCTCCTCCTTTGTGGACGAGGTTGAGAAAGT
         4700      4710      4720      4730      4740      4750      4760
        :::            :: :::::  ::::::::   ::         ::              ::
325   --AACTAA-------ATATTGTCTATAAGAAACT---TCAGTGCCA-------TGGACATGATTTAAA---
         2010      2020      2030        2040                2050
```

Fig. 2H-17

```
              4770      4780      4790      4800      4810      4820      4830
Slit  GGTGAAGTGCGGGCTGTGTACGAGGTGTGTGTCCTAAACACACTCCCGGCAGCTCTGTCTTGGAAAAGGTTG
         ::                                               :::        ::.:.:::
325   ------CTG----------------------AAAC----CTC-----------------CTT---ATATAATTA
            2060                                                  2070

4840      4850      4860      4870      4880      4890      4900
Slit  TATACTTCTTGACCATGTGGGACTAATGAATGCTTCATAGTGGAAATATTTGAAATATATTGTAAAATAC
      ::::::  :.:   ::         ..::.:  .  .:.:: .:::  .:: ::::::::  ::  ---
325   TATACTT-TAGT---TGGAAATATATGAATTATATGAGGTTAGCATTATTAAAATATGTTTTTAA---
           2080    2090           2100     2110     2120     2130

4910      4920      4930      4940      4950
Slit  AGAACAGACTTATTTTATTATGAGAATAAAGACTTTTTTTCTGCATTTG
          .::::.::::::::::     ..:    ::::.::: :  :  ::
325   ---------TAAAAAAAAAAAAAAAAAAAAAAGGGCG-----GCCGC----
                   2140      2150      2160
```

Fig. 2H-18

```
ALT   ------------------------------------------------------------
T364  MPLSLGAEMWGPEAWLLLLLLASFTGRCPAGELETSDVVTVVLGQDAKLPCFYRGDSGEQVGQVAWARV
               10        20        30        40        50        60        70

ALT   ------------------------------------------------------------
T364  DAGEGAQELALLHSKYGLHVSPAYEGRVEQPPPPRNPLDGSVLLRNAVQADEGEYECRVSTFPAGSFQAR
               80        90       100       110       120       130       140

ALT   ---------------------KGTTSSRSFKHSRSAAVTSEFHL
                                10        20
T364  LRLRVLVPPLPSLNPGPALEEGQGLTLAASCTAEGSPAPSVTWDTEVKGTTSSRSFKHSRSAAVTSEFHL
              150       160       170       180       190       200       210

ALT   VPSRSMNGQPLTCVVSHPGLLQDQRITHILHVSFLAEASVRGLEDQNLWHIGREGAMLKCLSEGQPPPSY
         :::::::::::::::::::::::::::::::::::::::::::::::::::::::::::::::::::
               30        40        50        60        70        80        90
T364  VPSRSMNGQPLTCVVSHPGLLQDQRITHILHVSFLAEASVRGLEDQNLWHIGREGAMLKCLSEGQPPPSY
              220       230       240       250       260       270       280
```

Fig. 3B

```
              100       110       120       130       140       150       160
ALT  NWTRLDGPLPSGVRVDGDTLGFPPLTTEHSGIYVCHVSNEFSSRDSQVTVDVLADPQEDSGKQVDLVSAS
     ::::::::::::::::::::::::::::::::::::::::::::::::::::::::: ::::::::::::
T364 NWTRLDGPLPSGVRVDGDTLGFPPLTTEHSGIYVCHVSNEFSSRDSQVTVDVL-DPQEDSGKQVDLVSAS
              290       300       310       320       330        340

170       180       190       200       210       220
ALT  VVVVGVIAALLFCLLVVVVVLMSRYHRRKAQQMTQKYEEELTLTRENSIRRLHSHHTDPRSQ-------
     :::::::::::::::::::::::::::::::::::::::::::::::::::::::::::::
T364 VVVVGVIAALLFCLLVVVVVLMSRYHRRKAQQMTQKYEEELTLTRENSIRRLHSHHTDPRSQPEESVGLR
              350       360       370       380       390       400       410

230       240       250       260       270
ALT  -------SEEPEGRSYSTLTTVREIETQTELLSPGSGRAEEEDQDEGIKQAMNHFVQEN
            ::::::::::::::::::::::::::::::::::::::::::::::::::::
T364 AEGHPDSLKDNSSCSVMSEEPEGRSYSTLTTVREIETQTELLSPGSGRAEEEDQDEGIKQAMNHFVQEN
              420       430       440       450       460       470       480

280       290
ALT  GTLRAKPTGNGIYINGRGHLV
     :::::::::::::::::::::
T364 GTLRAKPTGNGIYINGRGHLV
              490       500       510
```

Fig.3C

```
              10        20        30        40        50        60        70
human MMQEQQPQSTEKRGWLSLRLWSVAGISIALLSACFIVSCVVTYHFTYGETGKRLSELHSYHSSLTCFSEG
      :::::: ::   ::  :: :::::  ::  ::::: ::::::::  :  :  :::::::::::::::::
murine MVQERQSQGKGVC-W-TLRLWSAAVISMLLLSTCFIASCVVTYQFIMDQPSRRLYELHTYHSSLTCFSEG
              10        20        30        40        50        60

80        90       100       110       120       130
human TKVPA--WGCCPASWKSFGSSCYFISSEEKVWSKSEQNCVEMGAHLVVFNTEAEQNFIVQQLNESFSYFL
      : :::  :::: : :::::::::::: ::::: ::::::::: ::::::: :::::::: :::::::::
murine TMVSEKMWGCCPNHWKSFGSSCYLISTKENFWSTSEQNCVQMGAHLVVINTEAEQNFITQQLNESLSYFL
              70        80        90       100       110       120       130

140       150       160       170       180       190       200
human GLSDPQGNNNWQWIDKTPYEKNVRFWHLGEPNHSAEQCASIVFWKPTGWGWNDVICETRRNSICEMNKIY
      ::::: :::     :    :            :::    :  :       ::  :::::::::::::::
murine GLSDPKVMAN-------------KMSGSG--------------------TPMNPIFQKSGVF
             140                  150             160         170
```

Fig. 4C human L murine Q

```
human  ATGATGCAAGAGCAGCAACCCTCAAAGTACAGAGAAAAGAGGCTGGTTGTCCCTGAGACTCTGGTGG
       :: ::::::: ::         ::::::::: ::    :                :::::::::::::::
murine ATGGTGCAGGAAAGACAATCCCA----------AGGGAAGGGAGTCTGCTGAGACCCTGAGACTCTGGTCAGCTG
              10         20         30         40         50         60 human  CTGGGATTTCCATTGCACTCCCTCAGTGCTTGCTTCATTGTGAGCTGTGAGTAACTTACCATTTTACATA
       :::::::::::::::: ::::   :::::::::::::::::::::::::::: :::: ::::: ::::
murine CTGTGATTTCCATGTTACTCTTGAGTACCTGTTTCATTGCGAGCTGTGGTGACTTACCAATTATTAT
              80         90        100        110        120        130 human  TGGTGAAACTGGCAAAAGGCTGTCTGAACTACACTCATCATATCATTCAAGTCTCCACCTGCTTCAGTGAAGGG
       ::: :::::::::::: :::::::::::::::::    ::: :  ::::::::::::::::::::::::::::
murine GGACCAGCCCAGTAGAAGACTATATGAACTTCACACACATTCCAGTCTCCACCTGCTTCAGTGAAGGG
              150        160        170        180        190        200 human  ACAAAGGTGTCAGAAAAAATGTGCCCAGCC------TGGGGATGTTGCCCAGCTTCTTGGAAGTCATTTGGTTCCAGTTGCTACT
       ::  :::::::::::::::                ::::::::::::::::::        ::::::::::::::::::::::
murine ACTATGTGTGTCAGAAAATCACTGGAAGTGCTGCCCAAATCACTGGAAGTGCTGCCCAAATGTGGGGATGCTGCCCAAATCACTGGAAGTCATTTGGCTCCAGCTGCTACC
              220        230        240        250        260        270
```

Fig. 4D

```
                280        290        300        310        320        330        340
human    TCATTTCCAGTGAAGAGAAGGTTTGGTCTAAGAGTGAGCAGAACTGTGTTGAGATGGGAGCACATTTGGT
         :::::::: :: ::::: ::::: ::: :   : ::::::::::::::::::::::::::::::::::
murine   TCATTTCTACCAAGGAGAACTTCTGGAGCACCAGTGAGCAGAACTGTGTTCAGATGGGGGCTCATCTGGT
                280        290        300        310        320        330        340

350        360        370        380        390        400        410
human    TGTGTTCAACACAGAGAAGCAGAGCAGAATTTCATTGTCCAGCAGTGAATGAGTCATTTTCTTATTTCTG
         :::::::::: :::::::::::::::::::::::::   :  ::::::::::::::::::::: :::::
murine   GGTGATCAATACTGAAGCGGAGCAGAATTTCATCACCCAGCAGTGAATGAGTCACTTTTCTTACTTCCTG
                350        360        370        380        390        400        410

420        430        440        450        460        470        480
human    GGGCTTTCAGAGACCCAGTCC-CAAGGTAATAATTGGCAATGGATTGATAAGACACCTTATGAGAAAATGTCA
         :: ::: ::::::::::::::  :::::::: :::::::::::::::::::::::::: ::::::::::::
murine   GGTCTTTCGGATCC-CAAGGTAATAATGGCAAATGGCAATGGATCGATGATACTCCCTTTCAGTCAAAATGTCA
                420        430        440        450        460        470        480

490        500        510        520        530        540        550
human    GATTTTGGCACCTAGGTGAGCCCAATCATTCTGCAGAGCAATGTGCTTCAATAGTCTTCTGGAAACCTAC
         :: ::: ::::::: :::::: ::::::::: ::::: :::::::::::::::  :::::
murine   GGTTCTGGCACCCCCATGAACCTTCCAGAAGACCCGGTGTGTTTCAA-------------------------
                490        500        510        520        530

Fig. 4E
``` human AGGATGGGGCTGGAATGATGTTATCTGTGAAACTAGAAGGAATTCAATATGTGAGATGAATAAGATTTAC
murine ------------------------------------------------------------------ human CTA
murine ---

Fig. 4F

```
                10        20        30        40        50        60        70
mT405   MVQERQSQGKGVCWTLRLWSAAVISMLLLSTCFIASCVVTYQFIMDQPSRRLYELHTYHSSLTCFSEGTM
         ::::::::::::::::::::::::::::::::::::::::::::::::::::::::::::::::::::::
Dectin  MVQERQSQGKGVCWTLRLWSAAVISMLLLSTCFIASCVVTYQFIMDQPSRRLYELHTYHSSLTCFSEGTM
                10        20        30        40        50        60        70

80        90       100       110       120       130       140
mT405   VSEKMWGCCPNHWKSFGSSCYLISTKENFWSTSEQNCVQMGAHLVVINTEAEQNFITQQLNESLSYFLGL
         ::::::::::::::::::::::::::::::::::::::::::::::::::::::::::::::::::::::
Dectin  VSEKMWGCCPNHWKSFGSSCYLISTKENFWSTSEQNCVQMGAHLVVINTEAEQNFITQQLNESLSYFLGL
                80        90       100       110       120       130       140

150       160                      170
mT405   SDPKVMAN---GNGSMILLSVKMSGSGTPMNP--------------IF------QKSGVFQ
        ::: ::: :   :::::::  :            :                 :
Dectin  SDPQGNGKWQWIDDTPFSQNVRFWHPHEPNLPEERCVSIVYWNPSKWGWNDVFCDSKHNSICEMKKIYL
               150       160       170       180       190       200
```

Fig. 4G

```
hT405   MMQEQQPQSTEKRGWLSLRLMSVAGISIALLSACFIVSCVVTYHFTYGETGKRLSELHSYHSSLTCFSEG
        ::::::  ::::: :: ::.::.. :: ::  :: :.::::::: . : :::: : :.::::::::::
Dectin  MVQERQSQGKGVC-W-TLRLWSAAVISMLLLSTCFIASCVVTYQFIMDQPSRRLYELHTYHSSLTCFSEG
             10        20        30        40        50        60        70 hT405   TKVPA--WGCCPASWKSFGSSCYFISSEEKVWSKSEQNCVEMGAHLVVFNTEAEQNFIVQQLNESFSYFL
        ::  :  :::: . ::::::::::::..:: ::::::::.:::::::: :::::::::.::::: ::::
Dectin  TMVSEKMWGCCPNHWKSFGSSCYLISTKENFWSTSEQNCVQMGAHLVVINTEAEQNFITQQLNESLSYFL
         80        90       100       110       120       130       140 hT405   GLSDPQGNNNWQWIDKTPYEKNVRFWHLGEPNHSAEQCASIVFWKPTGWGWNDVICETRRNSICEMNKIYL
        :::::::::: :::: ::: :::::: :   :  : :: :::: :  ::::::: ::. ::::::.::::
Dectin  GLSDPQGNGKWQWIDDTPFSQNVRFWHPHEPNLPEERCVSIVYWNPSKWGWNDVFCDSKHNSICEMKKIYL
         150       160       170       180       190       200
```

Fig. 4H

SEQUENCE LISTING

<160> NUMBER OF SEQ ID NOS: 85
<210> SEQ ID NO 1
<211> LENGTH: 2964
<212> TYPE: DNA
<213> ORGANISM: Homo sapiens

<400> SEQUENCE: 1

| | | | | | |
|---|---|---|---|---|---|
| gtcgacccac | gcgtccgcgg | acgcgtgggg | acggctcccg | gctgcagtct | gcccgcccgc | 60 |
| cccgcgcggg | ggccgagtcg | cgaagcgcgc | ctgcgacccg | gcgtccggc | gcgctggaga | 120 |
| ggacgcgagg | agccatgagg | cgccagcctg | cgaaggtggc | ggcgctgctg | ctcgggctgc | 180 |
| tcttggagtg | cacagaagcc | aaaaagcatt | gctggtattt | cgaaggactc | tatccaacct | 240 |
| attatatatg | ccgctcctac | gaggactgct | gtggctccag | gtgctgtgtg | cgggccctct | 300 |
| ccatacagag | gctgtggtac | ttctggttcc | ttctgatgat | gggcgtgctt | ttctgctgcg | 360 |
| gagccggctt | cttcatccgg | aggcgcatgt | acccccgcc | gctgatcgag | gagccagcct | 420 |
| tcaatgtgtc | ctacaccagg | cagccccaa | atcccggccc | aggagcccag | cagccggggc | 480 |
| cgccctatta | cactgaccca | ggaggaccgg | ggatgaaccc | tgtcgggaat | ccatggcaa | 540 |
| tggcttttcca | ggtcccaccc | aactcacccc | agggagtgt | ggcctgcccg | ccccctccag | 600 |
| cctactgcaa | cacgcctccg | cccccgtacg | aacaggtagt | gaaggccaag | tagtgggtg | 660 |
| cccacgtgca | agaggagaga | caggagaggg | cctttccctg | gcctttctgt | cttcgttgat | 720 |
| gttcacttcc | aggaacggtc | tcgtgggctg | ctaagggcag | ttcctctgat | atcctcacag | 780 |
| caagcacagc | tctctttcag | gctttccatg | gagtacaata | tatgaactca | cactttgtct | 840 |
| cctctgttgc | ttctgtttct | gacgcagtct | gtgctctcac | atggtagtgt | ggtgacagtc | 900 |
| cccgagggct | gacgtccta | cggtggcgtg | accagatcta | caggagagag | actgagagga | 960 |
| agaaggcagt | gctggaggtg | caggtggcat | gtagaggggc | caggccgagc | atcccaggca | 1020 |
| agcatccttc | tgcccgggta | ttaataggaa | gccccatgcc | gggcggctca | gccgatgaag | 1080 |
| cagcagccga | ctgagctgag | cccagcaggt | catctgctcc | agcctgtcct | ctcgtcagcc | 1140 |
| ttcctcttcc | agaagctgtt | ggagagacat | tcaggagaga | gcaagcccct | tgtcatgttt | 1200 |
| ctgtctctgt | tcatatccta | aagatagact | tctcctgcac | cgccagggaa | gggtagcacg | 1260 |
| tgcagctctc | accgcaggat | ggggcctaga | atcaggcttg | ccttggaggc | ctgacagtga | 1320 |
| tctgacatcc | actaagcaaa | tttatttaaa | ttcatgggaa | atcacttcct | gccccaaact | 1380 |
| gagacattgc | attttgtgag | ctcttggtct | gatttggaga | aaggactgtt | acccattttt | 1440 |
| ttggtgtgtt | tatggaagtg | catgtagagc | gtcctgccct | ttgaaatcag | actgggtgtg | 1500 |
| tgtcttccct | ggacatcact | gcctctccag | ggcattctca | ggcccggggg | tctccttccc | 1560 |
| tcaggcagct | ccagtggtgg | gttctgaagg | gtgctttcaa | aacggggcac | atctggctgg | 1620 |
| gaagtcacat | ggactcttcc | agggagagag | accagctgag | gcgtctctct | ctgaggttgt | 1680 |
| gttgggtcta | agcgggtgtg | tgctgggctc | caaggaggag | gagcttgctg | ggaaaagaca | 1740 |
| ggagaagtac | tgactcaact | gcactgacca | tgttgtcata | attagaataa | agaagaagtg | 1800 |
| gtcggaaatg | cacattcctg | gataggaatc | acagctcacc | ccaggatctc | acaggtagtc | 1860 |
| tcctgagtag | ttgacggcta | gcggggagct | agttccgccg | catagttata | gtgttgatgt | 1920 |
| gtgaacgctg | acctgtcctg | tgtgctaaga | gctatgcagc | ttagctgagg | cgcctagatt | 1980 |
| actagatgtg | ctgtatcacg | gggaatgagg | tgggggtgct | tattttttaa | tgaactaatc | 2040 |

-continued

```
agagcctctt gagaaattgt tactcattga actggagcat caagacatct catggaagtg    2100
gatacggagt gatttggtgt ccatgctttt cactctgagg acatttaatc ggagaacctc    2160
ctggggaatt ttgtgggaga cacttgggaa caaaacagac accctgggaa tgcagttgca    2220
agcacagatg ctgccaccag tgtctctgac caccctggtg tgactgctga ctgccagcgt    2280
ggtacctccc atgctgcagg cctccatcta aatgagacaa caaagcacaa tgttcactgt    2340
ttacaaccaa gacaactgcg tgggtccaaa cactcctctt cctccaggtc atttgttttg    2400 cattttaat gtctttattt tttgtaatga aaaagcacac taagctgccc ctggaatcgg     2460
gtgcagctga ataggcaccc aaaagtccgt gactaaattt cgtttgtctt tttgatagca    2520
aattatgtta agagacagtg atggctaggg ctcaacaatt ttgtattccc atgtttgtgt    2580
gagacagagt ttgttttccc ttgaacttgg ttagaattgt gctactgtga acgctgatcc    2640
tgcatatgga agtcccactt tggtgacatt tcctggccat tcttgtttcc attgtgtgga    2700
tggtgggttg tgcccacttc ctggagtgag acagctcctg tgtgtagaa ttcccggagc     2760 gtccgtggtt cagagtaaac ttgaagcaga tctgtgcatg ctttcctct gcaacaattg     2820 gctcgtttct cttttttgtt ctcttttgat aggatcctgt ttcctatgtg tgcaaaataa    2880
aaataaattt gggcaaaaaa aaaaaaaaaa aaaaaaaaa aaaaaaaaaa aaaaaaaaa      2940 aaaaaaaaaa aaaagggcgg ccgc                                          2964
```

<210> SEQ ID NO 2
<211> LENGTH: 516
<212> TYPE: DNA
<213> ORGANISM: Homo sapiens

<400> SEQUENCE: 2

```
atgaggcgcc agcctgcgaa ggtggcggcg ctgctgctcg gctgctcttt ggagtgcaca    60
gaagccaaaa agcattgctg gtatttcgaa ggactctatc caacctatta tatatgccgc    120
tcctacgagg actgctgtgg ctccaggtgc tgtgtgcggg ccctctccat acagaggctg    180
tggtacttct ggttccttct gatgatgggc gtgcttttct gctgcggagc cggcttcttc    240
atccggaggc gcatgtaccc cccgccgctg atcgaggagc agccttcaa tgtgtcctac     300 accaggcagc ccccaaatcc cggcccagga gcccagcagc cggggccgcc ctattacact    360
gacccaggag gaccggggat gaaccctgtc gggaattcca tggcaatggc tttccaggtc    420
ccacccaact caccccaggg gagtgtggcc tgcccgcccc ctccagccta ctgcaacacg    480
cctccgcccc cgtacgaaca ggtagtgaag gccaag                              516
```

<210> SEQ ID NO 3
<211> LENGTH: 172
<212> TYPE: PRT
<213> ORGANISM: Homo sapiens

<400> SEQUENCE: 3

```
Met Arg Arg Gln Pro Ala Lys Val Ala Ala Leu Leu Leu Gly Leu Leu
  1               5                  10                  15

Leu Glu Cys Thr Glu Ala Lys Lys His Cys Trp Tyr Phe Glu Gly Leu
                 20                  25                  30

Tyr Pro Thr Tyr Tyr Ile Cys Arg Ser Tyr Glu Asp Cys Cys Gly Ser
             35                  40                  45

Arg Cys Cys Val Arg Ala Leu Ser Ile Gln Arg Leu Trp Tyr Phe Trp
         50                  55                  60

Phe Leu Leu Met Met Gly Val Leu Phe Cys Cys Gly Ala Gly Phe Phe
```

```
                65                  70                  75                  80
Ile Arg Arg Arg Met Tyr Pro Pro Leu Ile Glu Glu Pro Ala Phe
                    85                  90                  95

Asn Val Ser Tyr Thr Arg Gln Pro Pro Asn Pro Gly Pro Gly Ala Gln
                100                 105                 110

Gln Pro Gly Pro Pro Tyr Tyr Thr Asp Pro Gly Gly Pro Gly Met Asn
                115                 120                 125

Pro Val Gly Asn Ser Met Ala Met Ala Phe Gln Val Pro Pro Asn Ser
                130                 135                 140

Pro Gln Gly Ser Val Ala Cys Pro Pro Pro Ala Tyr Cys Asn Thr
145                 150                 155                 160

Pro Pro Pro Pro Tyr Glu Gln Val Val Lys Ala Lys
                165                 170

<210> SEQ ID NO 4
<211> LENGTH: 22
<212> TYPE: PRT
<213> ORGANISM: Homo sapiens

<400> SEQUENCE: 4

Met Arg Arg Gln Pro Ala Lys Val Ala Ala Leu Leu Leu Gly Leu Leu
1               5                   10                  15

Leu Glu Cys Thr Glu Ala
                20

<210> SEQ ID NO 5
<211> LENGTH: 150
<212> TYPE: PRT
<213> ORGANISM: Homo sapiens

<400> SEQUENCE: 5

Lys Lys His Cys Trp Tyr Phe Glu Gly Leu Tyr Pro Thr Tyr Tyr Ile
1               5                   10                  15

Cys Arg Ser Tyr Glu Asp Cys Cys Gly Ser Arg Cys Cys Val Arg Ala
                20                  25                  30

Leu Ser Ile Gln Arg Leu Trp Tyr Phe Trp Phe Leu Leu Met Met Gly
                35                  40                  45

Val Leu Phe Cys Cys Gly Ala Gly Phe Phe Ile Arg Arg Arg Met Tyr
            50                  55                  60

Pro Pro Pro Leu Ile Glu Glu Pro Ala Phe Asn Val Ser Tyr Thr Arg
65                  70                  75                  80

Gln Pro Pro Asn Pro Gly Pro Gly Ala Gln Gln Pro Gly Pro Pro Tyr
                85                  90                  95

Tyr Thr Asp Pro Gly Pro Gly Met Asn Pro Val Gly Asn Ser Met
                100                 105                 110

Ala Met Ala Phe Gln Val Pro Pro Asn Ser Pro Gln Gly Ser Val Ala
                115                 120                 125

Cys Pro Pro Pro Ala Tyr Cys Asn Thr Pro Pro Pro Pro Tyr Glu
            130                 135                 140

Gln Val Val Lys Ala Lys
145                 150

<210> SEQ ID NO 6
<211> LENGTH: 38
<212> TYPE: PRT
<213> ORGANISM: Homo sapiens

<400> SEQUENCE: 6
```

Lys Lys His Cys Trp Tyr Phe Glu Gly Leu Tyr Pro Thr Tyr Ile
1               5                   10                  15

Cys Arg Ser Tyr Glu Asp Cys Cys Gly Ser Arg Cys Cys Val Arg Ala
            20                  25                  30

Leu Ser Ile Gln Arg Leu
        35

<210> SEQ ID NO 7
<211> LENGTH: 21
<212> TYPE: PRT
<213> ORGANISM: Homo sapiens

<400> SEQUENCE: 7

Trp Tyr Phe Trp Phe Leu Leu Met Met Gly Val Leu Phe Cys Cys Gly
1               5                   10                  15

Ala Gly Phe Phe Ile
            20

<210> SEQ ID NO 8
<211> LENGTH: 91
<212> TYPE: PRT
<213> ORGANISM: Homo sapiens

<400> SEQUENCE: 8

Arg Arg Arg Met Tyr Pro Pro Pro Leu Ile Glu Glu Pro Ala Phe Asn
1               5                   10                  15

Val Ser Tyr Thr Arg Gln Pro Pro Asn Pro Gly Pro Gly Ala Gln Gln
            20                  25                  30

Pro Gly Pro Pro Tyr Tyr Thr Asp Pro Gly Gly Pro Gly Met Asn Pro
        35                  40                  45

Val Gly Asn Ser Met Ala Met Ala Phe Gln Val Pro Pro Asn Ser Pro
    50                  55                  60

Gln Gly Ser Val Ala Cys Pro Pro Pro Ala Tyr Cys Asn Thr Pro
65                  70                  75                  80

Pro Pro Pro Tyr Glu Gln Val Val Lys Ala Lys
                85                  90

<210> SEQ ID NO 9
<211> LENGTH:
<212> TYPE:
<213> ORGANISM:

<400> SEQUENCE: 9

000

<210> SEQ ID NO 10
<211> LENGTH:
<212> TYPE:
<213> ORGANISM:

<400> SEQUENCE: 10

000

<210> SEQ ID NO 11
<211> LENGTH: 2915
<212> TYPE: DNA
<213> ORGANISM: Mus sp.

<400> SEQUENCE: 11
gtcgacccac gcgtccggcc gcgcgtcctt ctgccggctt cagctcgtat ccccggagtc      60

-continued

```
cacccgcccg tcccggggtg cggactggcc ctgagctggc cgtacagccc ggcttcggac      120
ggtcctcgct ggagccatgg gccgccggct cggcagggtg gcggcgctgc tgctcgggct      180
gctagtggag tgcactgagg ccaaaaaaca ttgctggtat tttgaaggac tctatcccac      240
atactatata tgccgttcct atgaagactg ctgtggctcc aggtgctgtg tgagggccct      300
ttccatacag aggctgtggt attttttggtt cctgctgatg atgggtgtgc tgttctgctg      360
tggtgccggt ttcttcattc gccggcgcat gtatccgcca ccactcattg aggagcccac      420
attcaatgtg tcctatacca ggcagccacc aaatcctgct ccaggagcac agcaaatggg      480
accgccatat tacaccgacc ctggaggacc cgggatgaat cctgttggca ataccatggc      540
tatggctttc caggtccagc ccaattcacc tcacggaggc acaacttacc cacccctcc      600 ttcctactgc aacacgcctc accccccta tgaacaggtg gtgaaggaca gtagcaaga       660 tgctacatca aaggcaaaga ggatggacag gcccttttgt ttaccttccc atcctcaccg      720
atacttgctg ataggggtgg tccaagggaaa acttggatat tctcaaagca gcccagctc       780 tctttcaagt cttttgtgga ggacatttga atccacactg tctcctctgt tgcttctgtt      840
tctgatgtag tctgtgctct ctgagagagt gtggcaacag tccctgaggg ttgatattcc      900
tagggtgtcc agggtagatc ctcgggagag aggctaaggg gaaaggaagg catagcctgt      960
gtgttagggg gcagataaag tggtcaggct gagataagac tcacatgatg cagtagttgg     1020
cagtgaactt cgaagagaca ctatccacca tcccagccca ttctcctaat agaagctgtg     1080
gggctgtgtt gttgatgctc tttggtctcc actcacattt tgaaaatagg ctttcctctg     1140
caggaatagg aaagacccaa gtacatattt gcttccactt aaaaatgagg gtcagaacca     1200
ggcctcagtt ggacatctat agttaaataa aggccattag agaggggaaa tctttaagtt     1260 agggaaatt ctctaaatgg agacattgcg ttttatgaat catcgtctgg ctttctttt       1320 agtgcatgta ttgaagtgag ggtgtccttt gagatcagat ggggagagtg aactctgcgg     1380
ggggtggggt gtctctactc agagggctcc aacacccttt tcttaggtag ttctggtgat     1440
gggttttatg ggcactatag agctgagggg cacattaggc cgggtagtta cattgaccct     1500
tggagaggaa gaggacagcc aaagaaactc agcaaagcaa gaccagcatt gctgagttag     1560 agctaggggtt gtatgtgatc ccaacagaga tgtgctggcc tcagaagagg ggacgtttgt     1620
ggatagagcc gtgaaaacct acttagttgc acagatgaca taatcaaaag tagagaaaga     1680
agtgtagtta gagatgccat ttcccaggtg agaatcagag ctcatccata gatttacaag     1740
tagtggctgg agttaacagt atggagttct tttcccttgc gtagttagtc acgttgatgt     1800
gtatttaaac ccaggttgag accttgtgta ctaagagcaa ggaagtatag ctaagatgtc     1860
tagattattt atatgtagta tggtggggag tggggctgca aggaaggggg ctgacattgt     1920
aaatgagaaa atcagagcca tttgataaac tgttacttgt tggatcaggc atccaaaagt     1980
gtctcttgag tggacattga gtattcttta ccacctacaa gaccaggagg catggtgtca     2040
ttctccattg gggtatttat atgaggtaga ggttcaggaa tcgacagtag ctgtgtgggc     2100
ttagtttaag gactgaaagc atagggactg gtagacagtt tcataggaaa ctgcggggaa     2160
ggaatggata ccttaaaga cagtttgtgg atgcagatgc tgccacccat cattgagcac      2220
ccttgtgtct ctggcttcct gtcactggat ccagtacccc tccatgcttg ggtccttgtt     2280
ttacataaga caacaaagca caatgtctgc tgtttacaat caagacgact acatggtcca     2340
aacatttctt ctctcttcta tcacttgtgg ctttaacttc catttcctcc gttccttttt     2400
```

```
aaaatcaaga agcacagtca gagctgcccc tgggattgca tcagggaacg gctgatcaag    2460
gcattcagtg tccatgacta aatcttatct ttttgatagc aaatccttt aagaaactga     2520 acaattgcta aggctcagca attttatact ccaatgtctg tgtaaggtaa attttgtttg    2580
ccattgagcc cacattggaa ttccttctga cgtcaacact gacaatgcct atggaaattg    2640
cacttctggg tatatgtccc agcatccttg ttttcttatg tttggtgagt aaggctcacc    2700
ccttccagca gctctacttc tgtgtgctga ggtcctgtag agccggggct tgggcacaga    2760
catgaggcag acttgtgcat gctctttctt ggcaacactt ggctcatatt tcttgttctc    2820
ttttgataga gtcctgtttc ctatgtattt aaaaaataat aaaagtgaat ttagtcaaaa    2880
aaaaaaaaaa aaaaaaaaaa aaaagggcg gccgc                                2915
```

<210> SEQ ID NO 12
<211> LENGTH: 516
<212> TYPE: DNA
<213> ORGANISM: Mus sp.

<400> SEQUENCE: 12

```
atgggccgcc ggctcggcag ggtggcggcg ctgctgctcg ggctgctagt ggagtgcact     60
gaggccaaaa acattgctg gtattttgaa ggactctatc ccacatacta tatgccgt      120 tcctatgaag actgctgtgg ctccaggtgc tgtgtgaggg cccttttccat acagaggctg   180 tggtatttt ggttcctgct gatgatgggt gtgctgttct gctgtggtgc cggtttcttc    240
attcgccggc gcatgtatcc gccaccactc attgaggagc ccacattcaa tgtgtcctat    300
accaggcagc caccaaatcc tgctccagga gcacagcaaa tgggaccgcc atattacacc    360
gaccctggag gacccgggat gaatcctgtt ggcaatacca tggctatggc tttccaggtc    420
cagcccaatt cacctcacgg aggcacaact tacccacccc ctccttccta ctgcaacacg    480
cctccacccc cctatgaaca ggtggtgaag gacaag                              516
```

<210> SEQ ID NO 13
<211> LENGTH: 172
<212> TYPE: PRT
<213> ORGANISM: Mus sp.

<400> SEQUENCE: 13

```
Met Gly Arg Arg Leu Gly Arg Val Ala Ala Leu Leu Gly Leu Leu
1               5                   10                  15

Val Glu Cys Thr Glu Ala Lys Lys His Cys Trp Tyr Phe Glu Gly Leu
            20                  25                  30

Tyr Pro Thr Tyr Tyr Ile Cys Arg Ser Tyr Glu Asp Cys Cys Gly Ser
        35                  40                  45

Arg Cys Cys Val Arg Ala Leu Ser Ile Gln Arg Leu Trp Tyr Phe Trp
    50                  55                  60

Phe Leu Leu Met Met Gly Val Leu Phe Cys Cys Gly Ala Gly Phe Phe
65                  70                  75                  80

Ile Arg Arg Arg Met Tyr Pro Pro Leu Ile Glu Glu Pro Thr Phe
                85                  90                  95

Asn Val Ser Tyr Thr Arg Gln Pro Pro Asn Pro Ala Pro Gly Ala Gln
            100                 105                 110

Gln Met Gly Pro Pro Tyr Tyr Thr Asp Pro Gly Gly Pro Gly Met Asn
        115                 120                 125

Pro Val Gly Asn Thr Met Ala Met Ala Phe Gln Val Gln Pro Asn Ser
    130                 135                 140
```

```
Pro His Gly Gly Thr Thr Tyr Pro Pro Pro Ser Tyr Cys Asn Thr
145                 150                 155                 160

Pro Pro Pro Pro Tyr Glu Gln Val Val Lys Asp Lys
                165                 170
```

<210> SEQ ID NO 14
<211> LENGTH:
<212> TYPE:
<213> ORGANISM:

<400> SEQUENCE: 14

000

<210> SEQ ID NO 15
<211> LENGTH: 150
<212> TYPE: PRT
<213> ORGANISM: Mus sp.

<400> SEQUENCE: 15

```
Lys Lys His Cys Trp Tyr Phe Glu Gly Leu Tyr Pro Thr Tyr Tyr Ile
1               5                   10                  15

Cys Arg Ser Tyr Glu Asp Cys Cys Gly Ser Arg Cys Cys Val Arg Ala
                20                  25                  30

Leu Ser Ile Gln Arg Leu Trp Tyr Phe Trp Phe Leu Leu Met Met Gly
            35                  40                  45

Val Leu Phe Cys Cys Gly Ala Gly Phe Phe Ile Arg Arg Arg Met Tyr
        50                  55                  60

Pro Pro Pro Leu Ile Glu Glu Pro Thr Phe Asn Val Ser Tyr Thr Arg
65                  70                  75                  80

Gln Pro Pro Asn Pro Ala Pro Gly Ala Gln Gln Met Gly Pro Pro Tyr
                85                  90                  95

Tyr Thr Asp Pro Gly Gly Pro Gly Met Asn Pro Val Gly Asn Thr Met
                100                 105                 110

Ala Met Ala Phe Gln Val Gln Pro Asn Ser Pro His Gly Gly Thr Thr
            115                 120                 125

Tyr Pro Pro Pro Ser Tyr Cys Asn Thr Pro Pro Pro Tyr Glu
            130                 135                 140

Gln Val Val Lys Asp Lys
145                 150
```

<210> SEQ ID NO 16

<400> SEQUENCE: 16

000                                                                 3

<210> SEQ ID NO 17

<400> SEQUENCE: 17

000                                                                 3

<210> SEQ ID NO 18

<400> SEQUENCE: 18

000                                                                 3

<210> SEQ ID NO 19
<211> LENGTH:
<212> TYPE:

<213> ORGANISM:

<400> SEQUENCE: 19

000

<210> SEQ ID NO 20

<400> SEQUENCE: 20

000                                                                          3

<210> SEQ ID NO 21
<211> LENGTH: 2169
<212> TYPE: DNA
<213> ORGANISM: Homo sapiens

<400> SEQUENCE: 21

| | | | | | |
|---|---|---|---|---|---|
| gtcgacccac | gcgtccggaa | atgtcgttct | tcagatttaa | aaagaaaacc | tttactgaat | 60 |
| cagctgagtg | ttaataatac | gaatttcctt | ttcttgccaa | ttctgatctg | aacagaaaat | 120 |
| ccaagaacag | ggatatgtgt | ggattacagt | tttctctgcc | ttgcctacga | ctgtttctgg | 180 |
| ttgttacctg | ttatctttta | ttattactcc | acaaagaaat | acttggatgt | tcgtctgttt | 240 |
| gtcagctctg | cactgggaga | caaattaact | gccgtaactt | aggccttttcg | agtattccta | 300 |
| agaattttcc | tgaaagtaca | gttttttctgt | atctgactgg | gaataatata | tcttatataa | 360 |
| atgaaagtga | attaacagga | cttcattctc | ttgtagcatt | gtatttggat | aattctaaca | 420 |
| ttctgtatgt | atatccaaaa | gcctttgttc | aattgaggca | tctatatttt | ctatttctaa | 480 |
| ataataattt | catcaaacgc | ttagatcctg | gaatatttaa | gggacttttta | aatcttcgta | 540 |
| atttatattt | acagtataat | caggtatctt | tgttccgag | aggagtattt | aatgatctag | 600 |
| tttcagttca | gtacttaaat | ctacaaagga | atcgcctcac | tgtccttggg | agtggtacct | 660 |
| ttgttggtat | ggttgctctt | cggatacttg | atttatcaaa | caataacatt | ttgaggatat | 720 |
| cagaatcagg | ctttcaacat | cttgaaaacc | ttgcttgttt | gtatttagga | agtaataatt | 780 |
| taacaaaagt | accatcaaat | gcctttgaag | tacttaaaag | tcttagaaga | ctttctttgt | 840 |
| ctcataatcc | tattgaagca | atacagccct | ttgcatttaa | aggacttgcc | aatctggaat | 900 |
| acctcctcct | gaaaaattca | agaattagga | atgttactag | ggatgggttt | agtggaatta | 960 |
| ataatcttaa | acatttgatc | ttaagtcata | atgatttaga | gaatttaaat | tctgacacat | 1020 |
| tcagtttgtt | aaagaattta | atttaccttta | agttagatag | aaacagaata | attagcattg | 1080 |
| ataatgatac | atttgaaaat | atgggagcat | ctttgaagat | ccttaatctg | tcatttaata | 1140 |
| atcttacagc | cttgcatcca | agggtcctta | agccgttgtc | ttcattgatt | catcttcagg | 1200 |
| caaattctaa | tccttgggaa | tgtaactgca | aacttttggg | ccttcgagac | tggctagcat | 1260 |
| cttcagccat | tactctaaac | atctattgtc | agaatccccc | atccatgcgt | ggcagagcat | 1320 |
| tacgttatat | taacattaca | aattgtgtta | catcttcaat | aaatgtatcc | agagcttggg | 1380 |
| ctgttgtaaa | atctcctcat | attcatcaca | agactactgc | gctaatgatg | gcctggcata | 1440 |
| aagtaaccac | aaatggcagt | cctctggaaa | atactgagac | tgagaacatt | actttctggg | 1500 |
| aacgaattcc | tacttcacct | gctggtagat | ttttcaaga | gaatgccttt | ggtaatccat | 1560 |
| tagagactac | agcagtgtta | cctgtgcaaa | tacaacttac | tacttctgtt | accttgaact | 1620 |
| tggaaaaaaa | cagtgctcta | ccgaatgatg | ctgcttcaat | gtcagggaaa | acatctctaa | 1680 |
| tttgtacaca | agaagttgag | aagttgaatg | aggcttttga | cattttgcta | gcttttttca | 1740 |

-continued

```
tcttagcttg tgtttaatc attttttga tctacaaagt tgttcagttt aaacaaaaac    1800
taaaggcatc agaaaactca agggaaaata gacttgaata ctacagcttt tatcagtcag    1860
caaggtataa tgtaactgcc tcaatttgta acacttcccc aaattctcta gaaagtcctg    1920
gcttggagca gattcgactt cataaacaaa ttgttcctga aaatgaggca caggtcattc    1980
ttttgaaca ttctgcttta taactcaact aaatattgtc tataagaaac ttcagtgcca    2040
tggacatgat ttaaactgaa acctccttat ataattatat actttagttg gaaatataat    2100
gaattatatg aggttagcat tattaaaata tgtttttaat aaaaaaaaaa aaaaaaaag    2160
ggcggccgc                                                            2169

<210> SEQ ID NO 22
<211> LENGTH: 1866
<212> TYPE: DNA
<213> ORGANISM: Homo sapiens

<400> SEQUENCE: 22
atgtgtggat tacagttttc tctgccttgc ctacgactgt ttctggttgt tacctgttat     60
cttttattat tactccacaa agaaatactt ggatgttcgt ctgtttgtca gctctgcact    120
gggagacaaa ttaactgccg taacttaggc ctttcgagta ttcctaagaa ttttcctgaa    180
agtacagttt ttctgtatct gactgggaat aatatatctt atataaatga agtgaatta    240
acaggacttc attctcttgt agcattgtat ttggataatt ctaacattct gtatgtatat    300
ccaaaagcct tgttcaatt gaggcatcta tattttctat ttctaaataa taatttcatc    360
aaacgcttag atcctggaat atttaaggga cttttaaatc ttcgtaattt atatttacag    420
tataatcagg tatcttttgt tccgagagga gtatttaatg atctagtttc agttcagtac    480
ttaaatctac aaaggaatcg cctcactgtc cttgggagtg gtacctttgt tggtatggtt    540
gctcttcgga tacttgattt atcaaacaat aacattttga ggatatcaga atcaggcttt    600
caacatcttg aaaaccttgc ttgtttgtat ttaggaagta ataatttaac aaaagtacca    660
tcaaatgcct ttgaagtact aaaagtgtct agaagacttt ctttgtctca taatcctatt    720
gaagcaatac agcccttgc atttaaagga cttgccaatc tggaatacct cctcctgaaa    780
aattcaagaa ttaggaatgt tactagggat gggttagtg gaattaataa tcttaaacat    840
ttgatcttaa gtcataatga tttagagaat ttaaattctg acacattcag tttgttaaag    900
aatttaattt accttaagtt agatagaaac agaataatta gcattgataa tgatacattt    960
gaaaatatgg gagcatcttt gaagatcctt aatctgtcat ttaataatct tacagccttg    1020
catccaaggg tccttaagcc gttgtcttca ttgattcatc ttcaggcaaa ttctaatcct    1080
tgggaatgta actgcaaact ttgggccctt cgagactggc tagcatcttc agccattact    1140
ctaaacatct attgtcagaa tcccccatcc atgcgtggca gagcattacg ttatattaac    1200
attacaaatt gtgttacatc ttcaataaat gtatccagag cttgggctgt tgtaaaatct    1260
cctcatattc atcacaagac tactgcgcta atgatggcct ggcataaagt aaccacaaat    1320
ggcagtcctc tggaaaatac tgagactgag acattactt tctgggaacg aattcctact    1380
tcacctgctg gtagatttt tcaagagaat gcctttggta atccattaga gactacagca    1440
gtgttacctg tgcaaataca acttactact tctgttacct tgaacttgga aaaaacagt    1500
gctctaccga atgatgctgc ttcaatgtca gggaaaacat ctctaatttg tacacaagaa    1560
gttgagaagt tgaatgaggc ttttgacatt tgctagctgt ttttcatctt agcttgtgtt    1620
ttaatcattt ttttgatcta caaagttgtt cagtttaaac aaaaactaaa ggcatcagaa    1680
```

-continued

```
aactcaaggg aaaatagact tgaatactac agcttttatc agtcagcaag gtataatgta    1740
actgcctcaa tttgtaacac ttccccaaat tctctagaaa gtcctggctt ggagcagatt    1800
cgacttcata acaaattgt tcctgaaaat gaggcacagg tcattctttt tgaacattct     1860
gcttta                                                               1866
```

<210> SEQ ID NO 23
<211> LENGTH: 622
<212> TYPE: PRT
<213> ORGANISM: Homo sapiens

<400> SEQUENCE: 23

```
Met Cys Gly Leu Gln Phe Ser Leu Pro Cys Leu Arg Leu Phe Leu Val
1               5                   10                  15

Val Thr Cys Tyr Leu Leu Leu Leu His Lys Glu Ile Leu Gly Cys
            20                  25                  30

Ser Ser Val Cys Gln Leu Cys Thr Gly Arg Gln Ile Asn Cys Arg Asn
        35                  40                  45

Leu Gly Leu Ser Ser Ile Pro Lys Asn Phe Pro Glu Ser Thr Val Phe
    50                  55                  60

Leu Tyr Leu Thr Gly Asn Asn Ile Ser Tyr Ile Asn Glu Ser Glu Leu
65                  70                  75                  80

Thr Gly Leu His Ser Leu Val Ala Leu Tyr Leu Asp Asn Ser Asn Ile
                85                  90                  95

Leu Tyr Val Tyr Pro Lys Ala Phe Val Gln Leu Arg His Leu Tyr Phe
            100                 105                 110

Leu Phe Leu Asn Asn Asn Phe Ile Lys Arg Leu Asp Pro Gly Ile Phe
        115                 120                 125

Lys Gly Leu Leu Asn Leu Arg Asn Leu Tyr Leu Gln Tyr Asn Gln Val
    130                 135                 140

Ser Phe Val Pro Arg Gly Val Phe Asn Asp Leu Val Ser Val Gln Tyr
145                 150                 155                 160

Leu Asn Leu Gln Arg Asn Arg Leu Thr Val Leu Gly Ser Gly Thr Phe
                165                 170                 175

Val Gly Met Val Ala Leu Arg Ile Leu Asp Leu Ser Asn Asn Asn Ile
            180                 185                 190

Leu Arg Ile Ser Glu Ser Gly Phe Gln His Leu Glu Asn Leu Ala Cys
        195                 200                 205

Leu Tyr Leu Gly Ser Asn Asn Leu Thr Lys Val Pro Ser Asn Ala Phe
    210                 215                 220

Glu Val Leu Lys Ser Leu Arg Arg Leu Ser Leu Ser His Asn Pro Ile
225                 230                 235                 240

Glu Ala Ile Gln Pro Phe Ala Phe Lys Gly Leu Ala Asn Leu Glu Tyr
                245                 250                 255

Leu Leu Leu Lys Asn Ser Arg Ile Arg Asn Val Thr Arg Asp Gly Phe
            260                 265                 270

Ser Gly Ile Asn Asn Leu Lys His Leu Ile Leu Ser His Asn Asp Leu
        275                 280                 285

Glu Asn Leu Asn Ser Asp Thr Phe Ser Leu Leu Lys Asn Leu Ile Tyr
    290                 295                 300

Leu Lys Leu Asp Arg Asn Arg Ile Ile Ser Ile Asp Asn Asp Thr Phe
305                 310                 315                 320

Glu Asn Met Gly Ala Ser Leu Lys Ile Leu Asn Leu Ser Phe Asn Asn
                325                 330                 335
```

-continued

```
Leu Thr Ala Leu His Pro Arg Val Leu Lys Pro Leu Ser Ser Leu Ile
                340                 345                 350

His Leu Gln Ala Asn Ser Asn Pro Trp Glu Cys Asn Cys Lys Leu Leu
            355                 360                 365

Gly Leu Arg Asp Trp Leu Ala Ser Ser Ala Ile Thr Leu Asn Ile Tyr
        370                 375                 380

Cys Gln Asn Pro Pro Ser Met Arg Gly Arg Ala Leu Arg Tyr Ile Asn
385                 390                 395                 400

Ile Thr Asn Cys Val Thr Ser Ser Ile Asn Val Ser Arg Ala Trp Ala
                405                 410                 415

Val Val Lys Ser Pro His Ile His Lys Thr Thr Ala Leu Met Met
            420                 425                 430

Ala Trp His Lys Val Thr Thr Asn Gly Ser Pro Leu Glu Asn Thr Glu
        435                 440                 445

Thr Glu Asn Ile Thr Phe Trp Glu Arg Ile Pro Thr Ser Pro Ala Gly
    450                 455                 460

Arg Phe Phe Gln Glu Asn Ala Phe Gly Asn Pro Leu Glu Thr Thr Ala
465                 470                 475                 480

Val Leu Pro Val Gln Ile Gln Leu Thr Thr Ser Val Thr Leu Asn Leu
                485                 490                 495

Glu Lys Asn Ser Ala Leu Pro Asn Asp Ala Ala Ser Met Ser Gly Lys
            500                 505                 510

Thr Ser Leu Ile Cys Thr Gln Glu Val Glu Lys Leu Asn Glu Ala Phe
        515                 520                 525

Asp Ile Leu Leu Ala Phe Phe Ile Leu Ala Cys Val Leu Ile Ile Phe
    530                 535                 540

Leu Ile Tyr Lys Val Val Gln Phe Lys Gln Lys Leu Lys Ala Ser Glu
545                 550                 555                 560

Asn Ser Arg Glu Asn Arg Leu Glu Tyr Tyr Ser Phe Tyr Gln Ser Ala
                565                 570                 575

Arg Tyr Asn Val Thr Ala Ser Ile Cys Asn Thr Ser Pro Asn Ser Leu
            580                 585                 590

Glu Ser Pro Gly Leu Glu Gln Ile Arg Leu His Lys Gln Ile Val Pro
        595                 600                 605

Glu Asn Glu Ala Gln Val Ile Leu Phe Glu His Ser Ala Leu
    610                 615                 620

<210> SEQ ID NO 24
<211> LENGTH: 31
<212> TYPE: PRT
<213> ORGANISM: Homo sapiens

<400> SEQUENCE: 24

Met Cys Gly Leu Gln Phe Ser Leu Pro Cys Leu Arg Leu Phe Leu Val
1               5                   10                  15

Val Thr Cys Tyr Leu Leu Leu Leu His Lys Glu Ile Leu Gly
            20                  25                  30

<210> SEQ ID NO 25
<211> LENGTH: 591
<212> TYPE: PRT
<213> ORGANISM: Homo sapiens

<400> SEQUENCE: 25

Cys Ser Ser Val Cys Gln Leu Cys Thr Gly Arg Gln Ile Asn Cys Arg
1               5                   10                  15
```

```
Asn Leu Gly Leu Ser Ser Ile Pro Lys Asn Phe Pro Glu Ser Thr Val
             20                  25                  30

Phe Leu Tyr Leu Thr Gly Asn Asn Ile Ser Tyr Ile Asn Glu Ser Glu
             35                  40                  45

Leu Thr Gly Leu His Ser Leu Val Ala Leu Tyr Leu Asp Asn Ser Asn
             50                  55                  60

Ile Leu Tyr Val Tyr Pro Lys Ala Phe Val Gln Leu Arg His Leu Tyr
 65                  70                  75                  80

Phe Leu Phe Leu Asn Asn Asn Phe Ile Lys Arg Leu Asp Pro Gly Ile
                 85                  90                  95

Phe Lys Gly Leu Leu Asn Leu Arg Asn Leu Tyr Leu Gln Tyr Asn Gln
                100                 105                 110

Val Ser Phe Val Pro Arg Gly Val Phe Asn Asp Leu Val Ser Val Gln
             115                 120                 125

Tyr Leu Asn Leu Gln Arg Asn Arg Leu Thr Val Leu Gly Ser Gly Thr
             130                 135                 140

Phe Val Gly Met Val Ala Leu Arg Ile Leu Asp Leu Ser Asn Asn Asn
145                 150                 155                 160

Ile Leu Arg Ile Ser Glu Ser Gly Phe Gln His Leu Glu Asn Leu Ala
                165                 170                 175

Cys Leu Tyr Leu Gly Ser Asn Asn Leu Thr Lys Val Pro Ser Asn Ala
             180                 185                 190

Phe Glu Val Leu Lys Ser Leu Arg Arg Leu Ser Leu Ser His Asn Pro
             195                 200                 205

Ile Glu Ala Ile Gln Pro Phe Ala Phe Lys Gly Leu Ala Asn Leu Glu
         210                 215                 220

Tyr Leu Leu Leu Lys Asn Ser Arg Ile Arg Asn Val Thr Arg Asp Gly
225                 230                 235                 240

Phe Ser Gly Ile Asn Asn Leu Lys His Leu Ile Leu Ser His Asn Asp
                245                 250                 255

Leu Glu Asn Leu Asn Ser Asp Thr Phe Ser Leu Leu Lys Asn Leu Ile
             260                 265                 270

Tyr Leu Lys Leu Asp Arg Asn Arg Ile Ile Ser Ile Asp Asn Asp Thr
             275                 280                 285

Phe Glu Asn Met Gly Ala Ser Leu Lys Ile Leu Asn Leu Ser Phe Asn
         290                 295                 300

Asn Leu Thr Ala Leu His Pro Arg Val Leu Lys Pro Leu Ser Ser Leu
305                 310                 315                 320

Ile His Leu Gln Ala Asn Ser Asn Pro Trp Glu Cys Asn Cys Lys Leu
                325                 330                 335

Leu Gly Leu Arg Asp Trp Leu Ala Ser Ala Ile Thr Leu Asn Ile
             340                 345                 350

Tyr Cys Gln Asn Pro Pro Ser Met Arg Gly Arg Ala Leu Arg Tyr Ile
             355                 360                 365

Asn Ile Thr Asn Cys Val Thr Ser Ser Ile Asn Val Ser Arg Ala Trp
         370                 375                 380

Ala Val Val Lys Ser Pro His Ile His His Lys Thr Thr Ala Leu Met
385                 390                 395                 400

Met Ala Trp His Lys Val Thr Thr Asn Gly Ser Pro Leu Glu Asn Thr
                405                 410                 415

Glu Thr Glu Asn Ile Thr Phe Trp Glu Arg Ile Pro Thr Ser Pro Ala
             420                 425                 430
```

```
Gly Arg Phe Phe Gln Glu Asn Ala Phe Gly Asn Pro Leu Glu Thr Thr
            435                 440                 445

Ala Val Leu Pro Val Gln Ile Gln Leu Thr Thr Ser Val Thr Leu Asn
    450                 455                 460

Leu Glu Lys Asn Ser Ala Leu Pro Asn Asp Ala Ala Ser Met Ser Gly
465                 470                 475                 480

Lys Thr Ser Leu Ile Cys Thr Gln Glu Val Glu Lys Leu Asn Glu Ala
                485                 490                 495

Phe Asp Ile Leu Leu Ala Phe Ile Leu Ala Cys Val Leu Ile Ile
                500                 505                 510

Phe Leu Ile Tyr Lys Val Val Gln Phe Lys Gln Lys Leu Lys Ala Ser
            515                 520                 525

Glu Asn Ser Arg Glu Asn Arg Leu Glu Tyr Tyr Ser Phe Tyr Gln Ser
    530                 535                 540

Ala Arg Tyr Asn Val Thr Ala Ser Ile Cys Asn Thr Ser Pro Asn Ser
545                 550                 555                 560

Leu Glu Ser Pro Gly Leu Glu Gln Ile Arg Leu His Lys Gln Ile Val
                565                 570                 575

Pro Glu Asn Glu Ala Gln Val Ile Leu Phe Glu His Ser Ala Leu
            580                 585                 590

<210> SEQ ID NO 26
<211> LENGTH: 498
<212> TYPE: PRT
<213> ORGANISM: Homo sapiens

<400> SEQUENCE: 26

Cys Ser Ser Val Cys Gln Leu Cys Thr Gly Arg Gln Ile Asn Cys Arg
1               5                   10                  15

Asn Leu Gly Leu Ser Ser Ile Pro Lys Asn Phe Pro Glu Ser Thr Val
            20                  25                  30

Phe Leu Tyr Leu Thr Gly Asn Asn Ile Ser Tyr Ile Asn Glu Ser Glu
        35                  40                  45

Leu Thr Gly Leu His Ser Leu Val Ala Leu Tyr Leu Asp Asn Ser Asn
    50                  55                  60

Ile Leu Tyr Val Tyr Pro Lys Ala Phe Gln Leu Arg His Leu Tyr
65                  70                  75                  80

Phe Leu Phe Leu Asn Asn Asn Phe Ile Lys Arg Leu Asp Pro Gly Ile
                85                  90                  95

Phe Lys Gly Leu Leu Asn Leu Arg Asn Leu Tyr Leu Gln Tyr Asn Gln
            100                 105                 110

Val Ser Phe Val Pro Arg Gly Val Phe Asn Asp Leu Val Ser Val Gln
        115                 120                 125

Tyr Leu Asn Leu Gln Arg Asn Arg Leu Thr Val Leu Gly Ser Gly Thr
    130                 135                 140

Phe Val Gly Met Val Ala Leu Arg Ile Leu Asp Leu Ser Asn Asn Asn
145                 150                 155                 160

Ile Leu Arg Ile Ser Glu Ser Gly Phe Gln His Leu Glu Asn Leu Ala
                165                 170                 175

Cys Leu Tyr Leu Gly Ser Asn Asn Leu Thr Lys Val Pro Ser Asn Ala
            180                 185                 190

Phe Glu Val Leu Lys Ser Leu Arg Arg Leu Ser Leu Ser His Asn Pro
        195                 200                 205

Ile Glu Ala Ile Gln Pro Phe Ala Phe Lys Gly Leu Ala Asn Leu Glu
    210                 215                 220
```

```
Tyr Leu Leu Leu Lys Asn Ser Arg Ile Arg Asn Val Thr Arg Asp Gly
225                 230                 235                 240

Phe Ser Gly Ile Asn Asn Leu Lys His Leu Ile Leu Ser His Asn Asp
            245                 250                 255

Leu Glu Asn Leu Asn Ser Asp Thr Phe Ser Leu Leu Lys Asn Leu Ile
            260                 265                 270

Tyr Leu Lys Leu Asp Arg Asn Arg Ile Ser Ile Asp Asn Asp Thr
            275                 280                 285

Phe Glu Asn Met Gly Ala Ser Leu Lys Ile Leu Asn Leu Ser Phe Asn
290                 295                 300

Asn Leu Thr Ala Leu His Pro Arg Val Leu Lys Pro Leu Ser Ser Leu
305                 310                 315                 320

Ile His Leu Gln Ala Asn Ser Asn Pro Trp Glu Cys Asn Cys Lys Leu
                325                 330                 335

Leu Gly Leu Arg Asp Trp Leu Ala Ser Ser Ala Ile Thr Leu Asn Ile
                340                 345                 350

Tyr Cys Gln Asn Pro Pro Ser Met Arg Gly Arg Ala Leu Arg Tyr Ile
                355                 360                 365

Asn Ile Thr Asn Cys Val Thr Ser Ser Ile Asn Val Ser Arg Ala Trp
370                 375                 380

Ala Val Val Lys Ser Pro His Ile His His Lys Thr Thr Ala Leu Met
385                 390                 395                 400

Met Ala Trp His Lys Val Thr Thr Asn Gly Ser Pro Leu Glu Asn Thr
                405                 410                 415

Glu Thr Glu Asn Ile Thr Phe Trp Glu Arg Ile Pro Thr Ser Pro Ala
                420                 425                 430

Gly Arg Phe Phe Gln Glu Asn Ala Phe Gly Asn Pro Leu Glu Thr Thr
                435                 440                 445

Ala Val Leu Pro Val Gln Ile Gln Leu Thr Thr Ser Val Thr Leu Asn
450                 455                 460

Leu Glu Lys Asn Ser Ala Leu Pro Asn Asp Ala Ala Ser Met Ser Gly
465                 470                 475                 480

Lys Thr Ser Leu Ile Cys Thr Gln Glu Val Glu Lys Leu Asn Glu Ala
                485                 490                 495

Phe Asp

<210> SEQ ID NO 27
<211> LENGTH: 18
<212> TYPE: PRT
<213> ORGANISM: Homo sapiens

<400> SEQUENCE: 27

Ile Leu Leu Ala Phe Phe Ile Leu Ala Cys Val Leu Ile Ile Phe Leu
1               5                   10                  15

Ile Tyr

<210> SEQ ID NO 28
<211> LENGTH: 75
<212> TYPE: PRT
<213> ORGANISM: Homo sapiens

<400> SEQUENCE: 28

Lys Val Val Gln Phe Lys Gln Lys Leu Lys Ala Ser Glu Asn Ser Arg
1               5                   10                  15

Glu Asn Arg Leu Glu Tyr Tyr Ser Phe Tyr Gln Ser Ala Arg Tyr Asn
```

-continued

```
                    20                  25                  30
Val Thr Ala Ser Ile Cys Asn Thr Ser Pro Asn Ser Leu Glu Ser Pro
             35                  40                  45

Gly Leu Glu Gln Ile Arg Leu His Lys Gln Ile Val Pro Glu Asn Glu
 50                  55                  60

Ala Gln Val Ile Leu Phe Glu His Ser Ala Leu
65                  70                  75

<210> SEQ ID NO 29
<211> LENGTH: 1529
<212> TYPE: PRT
<213> ORGANISM: Homo sapiens

<400> SEQUENCE: 29

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
             20                  25                  30

Ser Cys Ser Gly Ser Thr Val Asp Cys His Gly Leu Ala Leu Arg Ser
             35                  40                  45

Val Pro Arg Asn Ile Pro Arg Asn Thr Glu Arg Leu Asp Leu Asn Gly
 50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                 85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320
```

```
Ser Pro Tyr Lys Lys Leu Arg Arg Ile Asp Leu Ser Asn Asn Gln Ile
            325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
            355                 360                 365

Glu Gly Leu Phe Ser Leu Gln Leu Leu Leu Asn Ala Asn Lys Ile
            370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
            405                 410                 415

Ser Pro Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
            435                 440                 445

Pro Ile Glu Thr Ser Gly Ala Arg Cys Thr Ser Pro Arg Arg Leu Ala
450                 455                 460

Asn Lys Arg Ile Gly Gln Ile Lys Ser Lys Phe Arg Cys Ser Ala
465                 470                 475                 480

Lys Glu Gln Tyr Phe Ile Pro Gly Thr Glu Asp Tyr Arg Ser Lys Leu
            485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
            515                 520                 525

Glu His Ile Pro Gln Tyr Thr Ala Glu Leu Arg Leu Asn Asn Asn Glu
            530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
            565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
            595                 600                 605

Lys Thr Leu Met Leu Arg Ser Asn Arg Ile Thr Cys Val Gly Asn Asp
            610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
            645                 650                 655

Ser Thr Leu Asn Leu Leu Ala Asn Pro Phe Asn Cys Asn Cys Tyr Leu
            660                 665                 670

Ala Trp Leu Gly Glu Trp Leu Arg Lys Arg Ile Val Thr Gly Asn
            675                 680                 685

Pro Arg Cys Gln Lys Pro Tyr Phe Leu Lys Glu Ile Pro Ile Gln Asp
            690                 695                 700

Val Ala Ile Gln Asp Phe Thr Cys Asp Asp Gly Asn Asp Asp Asn Ser
705                 710                 715                 720

Cys Ser Pro Leu Ser Arg Cys Pro Thr Glu Cys Thr Cys Leu Asp Thr
            725                 730                 735

Val Val Arg Cys Ser Asn Lys Gly Leu Lys Val Leu Pro Lys Gly Ile
```

-continued

```
                740                 745                 750
Pro Arg Asp Val Thr Glu Leu Tyr Leu Asp Gly Asn Gln Phe Thr Leu
            755                 760                 765
Val Pro Lys Glu Leu Ser Asn Tyr Lys His Leu Thr Leu Ile Asp Leu
        770                 775                 780
Ser Asn Asn Arg Ile Ser Thr Leu Ser Asn Gln Ser Phe Ser Asn Met
785                 790                 795                 800
Thr Gln Leu Leu Thr Leu Ile Leu Ser Tyr Asn Arg Leu Arg Cys Ile
                805                 810                 815
Pro Pro Arg Thr Phe Asp Gly Leu Lys Ser Leu Arg Leu Leu Ser Leu
            820                 825                 830
His Gly Asn Asp Ile Ser Val Val Pro Glu Gly Ala Phe Asn Asp Leu
        835                 840                 845
Ser Ala Leu Ser His Leu Ala Ile Gly Ala Asn Pro Leu Tyr Cys Asp
    850                 855                 860
Cys Asn Met Gln Trp Leu Ser Asp Trp Val Lys Ser Glu Tyr Lys Glu
865                 870                 875                 880
Pro Gly Ile Ala Arg Cys Ala Gly Pro Gly Glu Met Ala Asp Lys Leu
                885                 890                 895
Leu Leu Thr Thr Pro Ser Lys Lys Phe Thr Cys Gln Gly Pro Val Asp
            900                 905                 910
Val Asn Ile Leu Ala Lys Cys Asn Pro Cys Leu Ser Asn Pro Cys Lys
        915                 920                 925
Asn Asp Gly Thr Cys Asn Ser Asp Pro Val Asp Phe Tyr Arg Cys Thr
    930                 935                 940
Cys Pro Tyr Gly Phe Lys Gly Gln Asp Cys Asp Val Pro Ile His Ala
945                 950                 955                 960
Cys Ile Ser Asn Pro Cys Lys His Gly Gly Thr Cys His Leu Lys Glu
                965                 970                 975
Gly Glu Glu Asp Gly Phe Trp Cys Ile Cys Ala Asp Gly Phe Glu Gly
            980                 985                 990
Glu Asn Cys Glu Val Asn Val Asp  Asp Cys Glu Asp Asn  Asp Cys Glu
        995                 1000                1005
Asn Asn  Ser Thr Cys Val Asp  Gly Ile Asn Asn Tyr  Thr Cys Leu
    1010                1015                1020
Cys Pro  Pro Glu Tyr Thr Gly  Glu Leu Cys Glu Glu  Lys Leu Asp
    1025                1030                1035
Phe Cys  Ala Gln Asp Leu Asn  Pro Cys Gln His Asp  Ser Lys Cys
    1040                1045                1050
Ile Leu  Thr Pro Lys Gly Phe  Lys Cys Asp Cys Thr  Pro Gly Tyr
    1055                1060                1065
Val Gly  Glu His Cys Asp Ile  Asp Phe Asp Asp Cys  Gln Asp Asn
    1070                1075                1080
Lys Cys  Lys Asn Gly Ala His  Cys Thr Asp Ala Val  Asn Gly Tyr
    1085                1090                1095
Thr Cys  Ile Cys Pro Glu Gly  Tyr Ser Gly Leu Phe  Cys Glu Phe
    1100                1105                1110
Ser Pro  Pro Met Val Leu Pro  Arg Thr Ser Pro Cys  Asp Asn Phe
    1115                1120                1125
Asp Cys  Gln Asn Gly Ala Gln  Cys Ile Val Arg Ile  Asn Glu Pro
    1130                1135                1140
Ile Cys  Gln Cys Leu Pro Gly  Tyr Gln Gly Glu Lys  Cys Glu Lys
    1145                1150                1155
```

-continued

Leu Val Ser Val Asn Phe Ile Asn Lys Glu Ser Tyr Leu Gln Ile
1160              1165              1170

Pro Ser Ala Lys Val Arg Pro Gln Thr Asn Ile Thr Leu Gln Ile
1175              1180              1185

Ala Thr Asp Glu Asp Ser Gly Ile Leu Leu Tyr Lys Gly Asp Lys
1190              1195              1200

Asp His Ile Ala Val Glu Leu Tyr Arg Gly Arg Val Arg Ala Ser
1205              1210              1215

Tyr Asp Thr Gly Ser His Pro Ala Ser Ala Ile Tyr Ser Val Glu
1220              1225              1230

Thr Ile Asn Asp Gly Asn Phe His Ile Val Glu Leu Leu Ala Leu
1235              1240              1245

Asp Gln Ser Leu Ser Leu Ser Val Asp Gly Gly Asn Pro Lys Ile
1250              1255              1260

Ile Thr Asn Leu Ser Lys Gln Ser Thr Leu Asn Phe Asp Ser Pro
1265              1270              1275

Leu Tyr Val Gly Gly Met Pro Gly Lys Ser Asn Val Ala Ser Leu
1280              1285              1290

Arg Gln Ala Pro Gly Gln Asn Gly Thr Ser Phe His Gly Cys Ile
1295              1300              1305

Arg Asn Leu Tyr Ile Asn Ser Glu Leu Gln Asp Phe Gln Lys Val
1310              1315              1320

Pro Met Gln Thr Gly Ile Leu Pro Gly Cys Glu Pro Cys His Lys
1325              1330              1335

Lys Val Cys Ala His Gly Thr Cys Gln Pro Ser Ser Gln Ala Gly
1340              1345              1350

Phe Thr Cys Glu Cys Gln Glu Gly Trp Met Gly Pro Leu Cys Asp
1355              1360              1365

Gln Arg Thr Asn Asp Pro Cys Leu Gly Asn Lys Cys Val His Gly
1370              1375              1380

Thr Cys Leu Pro Ile Asn Ala Phe Ser Tyr Ser Cys Lys Cys Leu
1385              1390              1395

Glu Gly His Gly Gly Val Leu Cys Asp Glu Glu Glu Asp Leu Phe
1400              1405              1410

Asn Pro Cys Gln Ala Ile Lys Cys Lys His Gly Lys Cys Arg Leu
1415              1420              1425

Ser Gly Leu Gly Gln Pro Tyr Cys Glu Cys Ser Ser Gly Tyr Thr
1430              1435              1440

Gly Asp Ser Cys Asp Arg Glu Ile Ser Cys Arg Gly Glu Arg Ile
1445              1450              1455

Arg Asp Tyr Tyr Gln Lys Gln Gln Gly Tyr Ala Ala Cys Gln Thr
1460              1465              1470

Thr Lys Lys Val Ser Arg Leu Glu Cys Arg Gly Gly Cys Ala Gly
1475              1480              1485

Gly Gln Cys Cys Gly Pro Leu Arg Ser Lys Arg Arg Lys Tyr Ser
1490              1495              1500

Phe Glu Cys Thr Asp Gly Ser Ser Phe Val Asp Glu Val Glu Lys
1505              1510              1515

Val Val Lys Cys Gly Cys Thr Arg Cys Val Ser
1520              1525

<210> SEQ ID NO 30
<211> LENGTH: 4900

<212> TYPE: DNA
<213> ORGANISM: Homo sapiens

<400> SEQUENCE: 30

```
cagagcaggg tggagagggc ggtgggaggc gtgtgcctga gtgggctcta ctgccttgtt      60
ccatattatt ttgtgcacat tttccctggc actctgggtt gctagccccg ccgggcactg     120
ggcctcagac actgcgcggt tccctcggag cagcaagcta agaaagccc ccagtgccgg      180
cgaggaagga ggcggcgggg aaagatgcgc ggcgttggct ggcagatgct gtccctgtcg     240
ctggggttag tgctggcgat cctgaacaag gtggcaccgc aggcgtgccc ggcgcagtgc     300
tcttgctcgg gcagcacagt ggactgtcac gggctggcgc tgcgcagcgt gcccaggaat     360
atccccgca acaccgagag actggattta aatggaaata acatcacaag aattacgaag      420
acagattttg ctggtcttag acatctaaga gttcttcagc ttatggagaa taagattagc     480
accattgaaa gaggagcatt ccaggatctt aagaactag agagactgcg tttaaacaga      540
aatcaccttc agctgttcc tgagttgctg tttcttggga ctgcgaagct atacaggctt     600
gatctcagtg aaaaccaaat tcaggcaatc ccaaggaaag cttccgtgg ggcagttgac      660
ataaaaaatt tgcaactgga ttacaaccag atcagctgta ttgaagatgg ggcattcagg    720
gctctccggg acctggaagt gctcactctc aacaataaca acattactag actttctgtg    780
gcaagtttca accatatgcc taaacttagg acttttcgac tgcattcaaa caacctgtat    840
tgtgactgcc acctggcctg gctctccgac tggcttcgcc aaaggcctcg ggttggtctg    900
tacactcagt gtatgggccc ctcccacctg agaggccata atgtagccga ggttcaaaaa    960
cgagaatttg tctgcagtgg tcaccagtca tttatggctc cttcttgtag tgttttgcac   1020
tgccctgccg cctgtacctg tagcaacaat atcgtagact gtcgtgggaa aggtctcact   1080
gagatcccca caaatcttcc agagaccatc acagaaatac gtttggaaca gaacacaatc   1140
aaagtcatcc ctcctggagc tttctcacca tataaaaagc ttagacgaat tgacctgagc   1200
aataatcaga tctctgaact tgcaccagat gctttccaag gactacgctc tctgaattca   1260
cttgtcctct atgaaataa aatcacagaa ctccccaaaa gtttatttga aggactgttt   1320
tccttacagc tcctattatt gaatgccaac aagataaact gccttcgggt agatgctttt   1380
caggatctcc acaacttgaa ccttctctcc ctatatgaca caagcttca gaccatcgcc    1440
aaggggacct tttcacctct tcgggccatt caaactatgc atttggccca gaacccctttt  1500
atttgtgact gccatctcaa gtggctagcg gattatctcc ataccaaccc gattgagacc   1560
agtggtgccc gttgcaccag cccccgccgc ctggcaaaca aaagaattgg acagatcaaa   1620
agcaagaat tccgttgttc agctaaagaa cagtatttca ttccaggtac agaagattat   1680
cgatcaaaat taagtggaga ctgctttgcg gatctggctt gccctgaaaa gtgtcgctgt   1740
gaaggaacca cagtagattg ctctaatcaa aagctcaaca aaatcccgga gcacattccc   1800
cagtacactg cagagttgcg tctcaataat aatgaattta ccgtgttgga agccacagga   1860
atctttaaga aacttcctca attacgtaaa ataaactta gcaacaataa gatcacagat    1920
attgaggagg gagcatttga aggagcatct ggtgtaaatg aaatacttct tacgagtaat   1980
cgtttggaaa atgtgcagca taagatgttc aagggattgg aaagcctcaa actttttgatg 2040
ttgagaagca atcgaataac ctgtgtgggg aatgacagtt tcataggact cagttctgtg   2100
cgtttgcttt ctttgtatga taatcaaatt actacagttg caccaggggc atttgatact   2160
ctccattctt tatctactct aaacctcttg gccaatcctt ttaactgtaa ctgctacctg    2220
```

-continued

```
gcttggttgg gagagtggct gagaagaag agaattgtca cgggaaatcc tagatgtcaa    2280
aaaccatact tcctgaaaga aatacccatc caggatgtgg ccattcagga cttcacttgt    2340
gatgacggaa atgatgacaa tagttgctcc ccactttctc gctgtcctac tgaatgtact    2400
tgcttggata cagtcgtccg atgtagcaac aagggtttga aggtcttgcc gaaaggtatt    2460
ccaagagatg tcacagagtt gtatctggat ggaaaccaat ttacactggt tcccaaggaa    2520
ctctccaact acaaacattt aacacttata gacttaagta caacagaat aagcacgctt    2580 tctaatcaga gcttcagcaa catgacccag ctcctcacct taattcttag ttacaaccgt    2640
ctgagatgta ttcctcctcg cacctttgat ggattaaagt ctcttcgatt actttctcta    2700
catggaaatg acatttctgt tgtgcctgaa ggtgctttca atgatctttc tgcattatca    2760
catctagcaa ttggagccaa ccctctttac tgtgattgta acatgcagtg ttatccgac    2820 tgggtgaagt cggaatataa ggagcctgga attgctcgtt gtgctggtcc tggagaaatg    2880
gcagataaac ttttactcac aactccctcc aaaaaattta cctgtcaagg tcctgtggat    2940
gtcaatattc tagctaagtg taaccctgc ctatcaaatc cgtgtaaaaa tgatggcaca    3000
tgtaatagtg atccagttga cttttaccga tgcacctgtc catatggttt caaggggcag    3060
gactgtgatg tcccaattca tgcctgcatc agtaacccat gtaaacatgg aggaacttgc    3120
cacttaaagg aaggagaaga agatggattc tggtgtattt tgtgctgatgg atttgaagga    3180 gaaaattgtg aagtcaacgt tgatgattgt gaagataatg actgtgaaaa taattctaca    3240
tgtgtcgatg gcattaataa ctacacatgc ctttgcccac tgagtatac aggtgagttg    3300 tgtgaggaga agctggactt ctgtgcccag gacctgaacc cctgccagca cgattcaaag    3360
tgcatcctaa ctccaagggg attcaaatgt gactgcacac agggtacgt aggtgaacac    3420 tgcgacatcg attttgacga ctgccaagac aacaagtgta aaaacggagc ccactgcaca    3480
gatgcagtga acggctatac gtgcatatgc cccgaaggtt acagtggctt gttctgtgag    3540
ttttctccac ccatggtcct ccctcgtacc agccctgtg ataattttga ttgtcagaat    3600
ggagctcagt gtatcgtcag aataaatgag ccaatatgtc agtgtttgcc tggctatcag    3660
ggagaaaagt gtgaaaaatt ggttagtgtg aattttataa acaaagagtc ttatcttcag    3720
attccttcag ccaaggttcg gcctcagacg aacataacac ttcagattgc cacagatgaa    3780
gacagcggaa tcctcctgta taagggtgac aaagaccata tcgcggtaga actctatcgg    3840
gggcgtgttc gtgccagcta tgacaccggc tctcatccag cttctgccat ttacagtgtg    3900
gagacaatca atgatggaaa cttccacatt gtggaactac ttgccttgga tcagagtctc    3960
tctttgtccg tggatggtgg gaaccccaaa atcatcacta acttgtcaaa gcagtccact    4020 ctgaatttg actctccact ctatgtagga ggcatgccag ggaagagtaa cgtggcatct    4080
ctgcgccagg ccctgggca gaacggaacc agcttccacg gctgcatccg gaacctttac    4140
atcaacagtg agctgcagga cttccagaag gtgccgatgc aaacaggcat tttgcctggc    4200
tgtgagccat gccacaagaa ggtgtgtgcc catggcacat gcagcccag cagccaggca    4260 ggcttcacct gcgagtgcca ggaaggatgg atggggcccc tctgtgacca acggaccaat    4320
gacccttgcc ttggaaataa atgcgtacat ggcacctgct tgcccatcaa tgcgttctcc    4380
tacagctgta gtgcttgga gggccatgga ggtgtcctct gtgatgaaga ggaggatctg    4440
tttaacccat gccaggcgat caagtgcaag cacgggaagt gcaggctttc aggtctgggg    4500 cagcccctact gtaatgcag cagtggatac acgggggaca gctgtgatcg agaaatctct    4560
tgtcgagggg aaaggataag agattattac caaaagcagc agggctatgc tgcttgccaa    4620
```

-continued

| acaaccaaga aggtgtcccg attagagtgc agaggtgggt gtgcaggagg gcagtgctgt | 4680 |
| ggaccgctga ggagcaagcg gcggaaatac tctttcgaat gcactgacgg ctcctccttt | 4740 |
| gtggacgagt tgagaaagt ggtgaagtgc ggctgtacga ggtgtgtgtc ctaaacacac | 4800 |
| tcccggcagc tctgtctttg gaaaaggttg tatacttctt gaccatgtgg gactaatgaa | 4860 |
| tgcttcatag tggaaatatt tgaaatatat tgtaaaatac | 4900 |

<210> SEQ ID NO 31
<211> LENGTH: 3510
<212> TYPE: DNA
<213> ORGANISM: Homo sapiens

<400> SEQUENCE: 31

| gcagctctgg gggagctcgg agctcccgat cacggcttct tgggggtagc tacggctggg | 60 |
| tgtgtagaac ggggccgggg ctggggctgg gtccccctagt ggagacccaa gtgcgagagg | 120 |
| caagaactct gcagcttcct gccttctggg tcagttcctt attcaagtct gcagccggct | 180 |
| cccagggaga tctcggtgga acttcagaaa cgctgggcag tctgcctttc aaccatgccc | 240 |
| ctgtccctgg gagccgagat gtgggggcct gaggcctggc tgctgctgct gctactgctg | 300 |
| gcatcattta caggccggtg ccccgcgggt gagctggaga cctcagacgt ggtaactgtg | 360 |
| gtgctgggcc aggacgcaaa actgccctgc ttctaccgag gggactccgg cgagcaagtg | 420 |
| gggcaagtgg catgggctcg ggtggacgcg ggcgaaggcg cccaggaact agcgctactg | 480 |
| cactccaaat acgggcttca tgtgagcccg gcttacgagg gccgcgtgga gcagccgccg | 540 |
| cccccacgca accccctgga cggctcagtg ctcctgcgca acgcagtgca ggcggatgag | 600 |
| ggcgagtacg agtgccgggt cagcaccttc cccgccggac gcttccaggc gcggctgcgg | 660 |
| ctccgagtgc tggtgcctcc cctgccctca ctgaatcctg gtccagcact agaagagggc | 720 |
| cagggcctga ccctggcagc ctcctgcaca gctgagggca gcccagcccc cagcgtgacc | 780 |
| tgggacacgg aggtcaaagg cacaacgtcc agccgttcct tcaagcactc ccgctctgct | 840 |
| gccgtcacct cagagttcca cttggtgcct agccgcagca tgaatgggca gccactgact | 900 |
| tgtgtggtgt cccatcctgg cctgctccag gaccaaagga tcacccacat cctccacgtg | 960 |
| tccttccttg ctgaggcctc tgtgaggggc cttgaagacc aaaatctgtg gcacattggc | 1020 |
| agagaaggag ctatgctcaa gtgcctgagt gaagggcagc cccctcccctc atacaactgg | 1080 |
| acacggctat atgggcctct gcccagtggg gtacgagtgg atggggacac tttgggcttt | 1140 |
| cccccactga ccactgagca cagcggcatc tacgtctgcc atgtcagcaa tgagttctcc | 1200 |
| tcaagggatt ctcaggtcac tgtggatgtt cttgacccc aggaagactc tgggaagcag | 1260 |
| gtggacctag tgtcagcctc ggtggtggtg gtgggtgtga tcgccgcact cttgttctgc | 1320 |
| cttctggtgg tggtggtggt gctcatgtcc cgataccatc ggcgcaaggc ccagcagatg | 1380 |
| acccagaaat atgaggagga gctgacccta accaggagaa actccatccg gaggctgcat | 1440 |
| tcccatcaca cggaccccag gagccagccg gaggagagtg tagggctgag agccgagggc | 1500 |
| caccctgata gtctcaagga caacagtagc tgctctgtga tgagtgaaga gcccgagggc | 1560 |
| cgcagttact ccacgctgac cacggtgagg gagatagaaa cacagactga actgctgtct | 1620 |
| ccaggctctg ggcgggccga ggaggaggaa gatcaggatg aaggcatcaa acaggccatg | 1680 |
| aaccattttg ttcaggagaa tgggaccccta cgggccaagc ccacgggcaa tggcatctac | 1740 |
| atcaatgggc ggggacacct ggtctgaccc aggcctgcct cccttcccta ggcctggctc | 1800 |

| | |
|---|---|
| cttctgttga catgggagat tttagctcat cttgggggcc tccttaaaca cccccatttc | 1860 |
| ttgcggaaga tgctccccat cccactgact gcttgacctt tacctccaac ccttctgttc | 1920 |
| atcgggaggg ctccaccaat tgagtctctc ccaccatgca tgcaggtcac tgtgtgtgtg | 1980 |
| catgtgtgcc tgtgtgagtg ttgactgact gtgtgtgtgt ggagggtgtga ctgtccgtgg | 2040 |
| agggtgact gtgtccgtgg tgtgtattat gctgtcatat cagagtcaag tgaactgtgg | 2100 |
| tgtatgtgcc acgggatttg agtggttgcg tgggcaacac tgtcagggtt tggcgtgtgt | 2160 |
| gtcatgtggc tgtgtgtgac ctctgcctga aaaagcaggt attttctcag accccagagc | 2220 |
| agtattaatg atgcagaggt tggaggagag aggtggagac tgtggctcag acccaggtgt | 2280 |
| gcgggcatag ctggagctgg aatctgcctc cggtgtgagg gaacctgtct cctaccactt | 2340 |
| cggagccatg gggcaagtg tgaagcagcc agtccctggg tcagccagag gcttgaactg | 2400 |
| ttacagaagc cctctgccct ctggtggcct ctgggcctgc tgcatgtaca tattttctgt | 2460 |
| aaatatacat gcgccgggag cttcttgcag gaatactgct ccgaatcact tttaattttt | 2520 |
| ttcttttttt tttcttgccc tttccattag ttgtattttt tatttatttt tattttatt | 2580 |
| ttttttaga gatggagtct cactatgttg ctcaggctgg ccttgaactc ctgggctcaa | 2640 |
| gcaatcctcc tgcctcagcc tccctagtag ctgggacttt aagtgtacac cactgtgcct | 2700 |
| gctttgaatc ctttacgaag agaaaaaaaa aattaaagaa agcctttaga tttatccaat | 2760 |
| gtttactact gggattgctt aaagtgaggc ccctccaaca ccaggggtt aattcctgtg | 2820 |
| attgtgaaag gggctacttc caaggcatct tcatgcaggc agcccttgg gagggcacct | 2880 |
| gagagctggt agagtctgaa attagggatg tgagcctcgt ggttactgag taaggtaaaa | 2940 |
| ttgcatccac cattgtttgt gataccttag ggaattgctt ggacctggtg acaagggctc | 3000 |
| ctgttcaata gtggtgttgg ggagagagag agcagtgatt atagaccgag agagtaggag | 3060 |
| ttgaggtgag gtgaaggagg tgctgggggt gagaatgtcg cctttccccc tgggttttgg | 3120 |
| atcactaatt caaggctctt ctggatgttt ctctggggttg gggctggagt tcaatgaggt | 3180 |
| ttatttttag ctggcccacc cagatacact cagccagaat acctagattt agtacccaaa | 3240 |
| ctcttcttag tctgaaatct gctggatttc tggcctaagg gagaggctcc catccttcgt | 3300 |
| tccccagcca gcctaggact tcgaatgtgg agcctgaaga tctaagatcc taacatgtac | 3360 |
| attttatgta aatatgtgca tatttgtaca taaaatgata ttctgttttt aaataaacag | 3420 |
| acaaaacttg aaaaaaaaaa aaaaaaaaaa aaaaaaaaa aaaaaaaaa aaaaaaaaaa | 3480 |
| aaaaaaaaaa aaaaaaaaa aaaaaaaaa | 3510 |

<210> SEQ ID NO 32
<211> LENGTH: 1530
<212> TYPE: DNA
<213> ORGANISM: Homo sapiens

<400> SEQUENCE: 32

| | |
|---|---|
| atgccctgt ccctgggagc cgagatgtgg gggcctgagg cctggctgct gctgctgcta | 60 |
| ctgctggcat catttacagg ccggtgcccc gcgggtgagc tggagacctc agacgtggta | 120 |
| actgtggtgc tgggccagga cgcaaaactg ccctgcttct accgagggga ctccggcgag | 180 |
| caagtgggc aagtggcatg ggctcgggtg acgcgggcg aaggcgccca ggaactagcg | 240 |
| ctactgcact ccaaatacgg gcttcatgtg agcccggctt acgagggccg cgtggagcag | 300 |
| ccgccgcccc cacgcaaccc cctgacggc tcagtgctcc tgcgcaacgc agtgcaggcg | 360 |
| gatgagggcg agtacgagtg ccgggtcagc acccttcccc ccgggcagctt ccaggcgcgg | 420 |

-continued

```
ctgcggctcc gagtgctggt gcctcccctg ccctcactga atcctggtcc agcactagaa    480
gagggccagg gcctgaccct ggcagcctcc tgcacagctg agggcagccc agccccagc     540
gtgacctggg acacggaggt caaaggcaca acgtccagcc gttccttcaa gcactcccgc    600
tctgctgccg tcacctcaga gttccacttg gtgcctagcc gcagcatgaa tgggcagcca    660
ctgacttgtg tggtgtccca tcctggcctg ctccaggacc aaaggatcac ccacatcctc    720
cacgtgtcct tccttgctga ggcctctgtg agggccttg aagaccaaaa tctgtggcac     780
attggcagag aaggagctat gctcaagtgc ctgagtgaag gcagccccc tccctcatac     840
aactggacac ggctggatgg gcctctgccc agtggggtac gagtggatgg ggacactttg    900
ggctttcccc cactgaccac tgagcacagc ggcatctacg tctgccatgt cagcaatgag    960
ttctcctcaa gggattctca ggtcactgtg gatgttcttg accccagga agactctggg    1020
aagcaggtgg acctagtgtc agcctcggtg gtggtggtgg gtgtgatcgc cgcactcttg    1080
ttctgccttc tggtggtggt ggtggtgctc atgtcccgat accatcggcg caaggcccag    1140
cagatgaccc agaaatatga ggaggagctg accctgacca gggagaactc catccggagg    1200
ctgcattccc atcacacgga ccccaggagc cagccggagg agagtgtagg gctgagagcc    1260
gagggccacc ctgatagtct caaggacaac agtagctgct ctgtgatgag tgaagagccc    1320
gagggccgca gttactccac gctgaccacg gtgagggaga tagaaacaca gactgaactg    1380
ctgtctccag gctctgggcg ggccgaggag gaggaagatc aggatgaagg catcaaacag    1440
gccatgaacc attttgttca ggagaatggg accctacggg ccaagcccac gggcaatggc    1500
atctacatca atgggcgggg acacctggtc                                     1530
```

<210> SEQ ID NO 33
<211> LENGTH: 510
<212> TYPE: PRT
<213> ORGANISM: Homo sapiens

<400> SEQUENCE: 33

```
Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
                20                  25                  30

Glu Leu Glu Thr Ser Asp Val Thr Val Val Leu Gly Gln Asp Ala
            35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
        115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175
```

```
Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
            195                 200                 205

His Leu Val Pro Ser Arg Ser Met Asn Gly Gln Pro Leu Thr Cys Val
            210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Ser Tyr Asn Trp Thr Arg Leu Asp Gly Pro
            275                 280                 285

Leu Pro Ser Gly Val Arg Val Asp Gly Asp Thr Leu Gly Phe Pro Pro
            290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val
            355                 360                 365

Val Leu Met Ser Arg Tyr His Arg Arg Lys Ala Gln Gln Met Thr Gln
            370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
            420                 425                 430

Cys Ser Val Met Ser Glu Glu Pro Glu Gly Arg Ser Tyr Ser Thr Leu
            435                 440                 445

Thr Thr Val Arg Glu Ile Glu Thr Gln Thr Glu Leu Leu Ser Pro Gly
            450                 455                 460

Ser Gly Arg Ala Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
                485                 490                 495

Thr Gly Asn Gly Ile Tyr Ile Asn Gly Arg Gly His Leu Val
            500                 505                 510

<210> SEQ ID NO 34
<211> LENGTH: 31
<212> TYPE: PRT
<213> ORGANISM: Homo sapiens

<400> SEQUENCE: 34

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala
            20                  25                  30
```

```
<210> SEQ ID NO 35
<211> LENGTH: 479
<212> TYPE: PRT
<213> ORGANISM: Homo sapiens

<400> SEQUENCE: 35

Gly Glu Leu Glu Thr Ser Asp Val Val Thr Val Leu Gly Gln Asp
 1               5                  10                  15

Ala Lys Leu Pro Cys Phe Tyr Arg Gly Asp Ser Gly Glu Gln Val Gly
                20                  25                  30

Gln Val Ala Trp Ala Arg Val Asp Ala Gly Glu Gly Ala Gln Glu Leu
            35                  40                  45

Ala Leu Leu His Ser Lys Tyr Gly Leu His Val Ser Pro Ala Tyr Glu
        50                  55                  60

Gly Arg Val Glu Gln Pro Pro Pro Arg Asn Pro Leu Asp Gly Ser
65                  70                  75                  80

Val Leu Leu Arg Asn Ala Val Gln Ala Asp Glu Gly Glu Tyr Glu Cys
                85                  90                  95

Arg Val Ser Thr Phe Pro Ala Gly Ser Phe Gln Ala Arg Leu Arg Leu
               100                 105                 110

Arg Val Leu Val Pro Pro Leu Pro Ser Leu Asn Pro Gly Pro Ala Leu
           115                 120                 125

Glu Glu Gly Gln Gly Leu Thr Leu Ala Ala Ser Cys Thr Ala Glu Gly
       130                 135                 140

Ser Pro Ala Pro Ser Val Thr Trp Asp Thr Glu Val Lys Gly Thr Thr
145                 150                 155                 160

Ser Ser Arg Ser Phe Lys His Ser Arg Ser Ala Ala Val Thr Ser Glu
                165                 170                 175

Phe His Leu Val Pro Ser Arg Ser Met Asn Gly Gln Pro Leu Thr Cys
            180                 185                 190

Val Val Ser His Pro Gly Leu Leu Gln Asp Gln Arg Ile Thr His Ile
        195                 200                 205

Leu His Val Ser Phe Leu Ala Glu Ala Ser Val Arg Gly Leu Glu Asp
    210                 215                 220

Gln Asn Leu Trp His Ile Gly Arg Glu Gly Ala Met Leu Lys Cys Leu
225                 230                 235                 240

Ser Glu Gly Gln Pro Pro Ser Tyr Asn Trp Thr Arg Leu Asp Gly
                245                 250                 255

Pro Leu Pro Ser Gly Val Arg Val Asp Gly Asp Thr Leu Gly Phe Pro
            260                 265                 270

Pro Leu Thr Thr Glu His Ser Gly Ile Tyr Val Cys His Val Ser Asn
        275                 280                 285

Glu Phe Ser Ser Arg Asp Ser Gln Val Thr Val Asp Val Leu Asp Pro
    290                 295                 300

Gln Glu Asp Ser Gly Lys Gln Val Asp Leu Val Ser Ala Ser Val Val
305                 310                 315                 320

Val Val Gly Val Ile Ala Ala Leu Leu Phe Cys Leu Leu Val Val Val
                325                 330                 335

Val Val Leu Met Ser Arg Tyr His Arg Arg Lys Ala Gln Gln Met Thr
            340                 345                 350

Gln Lys Tyr Glu Glu Glu Leu Thr Leu Thr Arg Glu Asn Ser Ile Arg
        355                 360                 365

Arg Leu His Ser His His Thr Asp Pro Arg Ser Gln Pro Glu Glu Ser
    370                 375                 380
```

```
Val Gly Leu Arg Ala Glu Gly His Pro Asp Ser Leu Lys Asp Asn Ser
385                 390                 395                 400

Ser Cys Ser Val Met Ser Glu Pro Glu Gly Arg Ser Tyr Ser Thr
            405                 410                 415

Leu Thr Thr Val Arg Glu Ile Glu Thr Gln Thr Glu Leu Leu Ser Pro
            420                 425                 430

Gly Ser Gly Arg Ala Glu Glu Glu Asp Gln Asp Glu Gly Ile Lys
        435                 440                 445

Gln Ala Met Asn His Phe Val Gln Glu Asn Gly Thr Leu Arg Ala Lys
    450                 455                 460

Pro Thr Gly Asn Gly Ile Tyr Ile Asn Gly Arg Gly His Leu Val
465                 470                 475

<210> SEQ ID NO 36
<211> LENGTH: 314
<212> TYPE: PRT
<213> ORGANISM: Homo sapiens

<400> SEQUENCE: 36

Gly Glu Leu Glu Thr Ser Asp Val Val Thr Val Leu Gly Gln Asp
1               5                   10                  15

Ala Lys Leu Pro Cys Phe Tyr Arg Gly Asp Ser Gly Glu Gln Val Gly
                20                  25                  30

Gln Val Ala Trp Ala Arg Val Asp Ala Gly Glu Gly Ala Gln Glu Leu
        35                  40                  45

Ala Leu Leu His Ser Lys Tyr Gly Leu His Val Ser Pro Ala Tyr Glu
    50                  55                  60

Gly Arg Val Glu Gln Pro Pro Pro Arg Asn Pro Leu Asp Gly Ser
65                  70                  75                  80

Val Leu Leu Arg Asn Ala Val Gln Ala Asp Glu Gly Glu Tyr Glu Cys
                85                  90                  95

Arg Val Ser Thr Phe Pro Ala Gly Ser Phe Gln Ala Arg Leu Arg Leu
                100                 105                 110

Arg Val Leu Val Pro Pro Leu Pro Ser Leu Asn Pro Gly Pro Ala Leu
            115                 120                 125

Glu Glu Gly Gln Gly Leu Thr Leu Ala Ala Ser Cys Thr Ala Glu Gly
130                 135                 140

Ser Pro Ala Pro Ser Val Thr Trp Asp Thr Glu Val Lys Gly Thr Thr
145                 150                 155                 160

Ser Ser Arg Ser Phe Lys His Ser Arg Ser Ala Ala Val Thr Ser Glu
                165                 170                 175

Phe His Leu Val Pro Ser Arg Ser Met Asn Gly Gln Pro Leu Thr Cys
            180                 185                 190

Val Val Ser His Pro Gly Leu Leu Gln Asp Gln Arg Ile Thr His Ile
        195                 200                 205

Leu His Val Ser Phe Leu Ala Glu Ala Ser Val Arg Gly Leu Glu Asp
    210                 215                 220

Gln Asn Leu Trp His Ile Gly Arg Glu Gly Ala Met Leu Lys Cys Leu
225                 230                 235                 240

Ser Glu Gly Gln Pro Pro Ser Tyr Asn Trp Thr Arg Leu Asp Gly
                245                 250                 255

Pro Leu Pro Ser Gly Val Arg Val Asp Gly Asp Thr Leu Gly Phe Pro
            260                 265                 270

Pro Leu Thr Thr Glu His Ser Gly Ile Tyr Val Cys His Val Ser Asn
            275                 280                 285
```

```
Glu Phe Ser Ser Arg Asp Ser Gln Val Thr Val Asp Val Leu Asp Pro
    290                 295                 300

Gln Glu Asp Ser Gly Lys Gln Val Asp Leu
305                 310
```

<210> SEQ ID NO 37
<211> LENGTH: 25
<212> TYPE: PRT
<213> ORGANISM: Homo sapiens

<400> SEQUENCE: 37

```
Val Ser Ala Ser Val Val Val Gly Val Ile Ala Ala Leu Leu Phe
1               5                   10                  15

Cys Leu Leu Val Val Val Val Leu
                20              25
```

<210> SEQ ID NO 38
<211> LENGTH: 140
<212> TYPE: PRT
<213> ORGANISM: Homo sapiens

<400> SEQUENCE: 38

```
Met Ser Arg Tyr His Arg Arg Lys Ala Gln Gln Met Thr Gln Lys Tyr
1               5                   10                  15

Glu Glu Glu Leu Thr Leu Thr Arg Glu Asn Ser Ile Arg Arg Leu His
                20                  25                  30

Ser His His Thr Asp Pro Arg Ser Gln Pro Glu Glu Ser Val Gly Leu
            35                  40                  45

Arg Ala Glu Gly His Pro Asp Ser Leu Lys Asp Asn Ser Ser Cys Ser
        50                  55                  60

Val Met Ser Glu Glu Pro Glu Gly Arg Ser Tyr Ser Thr Leu Thr Thr
65                  70                  75                  80

Val Arg Glu Ile Glu Thr Gln Thr Glu Leu Leu Ser Pro Gly Ser Gly
                85                  90                  95

Arg Ala Glu Glu Glu Asp Gln Asp Glu Gly Ile Lys Gln Ala Met
            100                 105                 110

Asn His Phe Val Gln Glu Asn Gly Thr Leu Arg Ala Lys Pro Thr Gly
        115                 120                 125

Asn Gly Ile Tyr Ile Asn Gly Arg Gly His Leu Val
    130                 135                 140
```

<210> SEQ ID NO 39

<400> SEQUENCE: 39

000                                                              3

<210> SEQ ID NO 40

<400> SEQUENCE: 40

000                                                              3

<210> SEQ ID NO 41
<211> LENGTH: 2510
<212> TYPE: DNA
<213> ORGANISM: Homo sapiens

<400> SEQUENCE: 41
caaaggcaca acgtccagcc gttccttcaa gcactcccgc tctgctgccg tcacctcaga    60

-continued

```
gttccacttg gtgcctagcc gcagcatgaa tgggcagcca ctgacttgtg tggtgtccca      120
tcctggcctg ctccaggacc aaaggatcac ccacatcctc cacgtgtcct tccttgctga      180
ggcctctgtg aggggccttg aagaccaaaa tctgtggcac attggcagag aaggagctat      240
gctcaagtgc ctgagtgaag ggcagccccc tccctcatac aactggacac ggctggatgg      300
gcctctgccc agtggggtac gagtggatgg ggacactttg gctttcccc cactgaccac       360 tgagcacagc ggcatctacg tctgccatgt cagcaatgag ttctcctcaa gggattctca      420
ggtcactgtg gatgttcttg cagaccccca ggaagactct gggaagcagg tggacctagt      480
gtcagcctcg gtggtggtgg tgggtgtgat cgccgcactc ttgttctgcc ttctggtggt      540
ggtggtggtg ctcatgtccc gataccatcg gcgcaaggcc cagcagatga cccagaaata      600
tgaggaggag ctgaccctga ccagggagaa ctccatccgg aggctgcatt cccatcacac      660
ggaccccagg agccagagtg aagagcccga gggccgcagt tactccacgc tgaccacggt      720
gagggagata gaaacacaga ctgaactgct gtctccaggc tctgggcggg ccgaggagga      780
ggaagatcag gatgaaggca tcaaacaggc catgaaccat tttgttcagg agaatgggac      840
cctacgggcc aagcccacgg gcaatggcat ctacatcaat gggcggggac acctggtctg      900
acccaggcct gcctcccttc cctaggcctg gctccttctg ttgacatggg agattttagc      960
tcatcttggg ggcctcctta aacaccccca tttcttgcgg aagatgctcc ccatcccact     1020
gactgcttga cctttacctc caacccttct gttcatcggg agggctccac caattgagtc     1080
tctcccacca tgcatgcagg tcactgtgtg tgtgcatgtg tgcctgtgtg agtgttgact     1140
gactgtgtgt gtgtggaggg gtgactgtcc gtggagggt gactgtgtcc gtggtgtgta      1200
ttatgctgtc atatcagagt caagtgaact gtggtgtatg tgccacggga tttgagtggt     1260
tgcgtgggca acactgtcag ggtttggcgt gtgtgtcatg tggctgtgtg tgacctctgc     1320
ctgaaaaagc aggtattttc tcagaccccca gagcagtatt aatgatgcag aggttggagg     1380
agagaggtgg agactgtggc tcagacccag gtgtgcgggc atagctggag ctggaatctg     1440
cctccggtgt gagggaacct gtctcctacc acttcggagc catgggggca agtgtgaagc     1500
agccagtccc tgggtcagcc agaggcttga actgttacag aagccctctg ccctctggtg     1560
gcctctgggc ctgctgcatg tacatatttt ctgtaaatat acatgcgccg ggagcttctt     1620
gcaggaatac tgctccgaat cacttttaat ttttttcttt tttttttctt gcccttttcca    1680 ttagttgtat ttttttattta ttttttatttt tatttttttt tagagatgga gtctcactat    1740
gttgctcagg ctggccttga actcctgggc tcaagcaatc ctcctgcctc agcctcccta     1800
gtagctggga ctttaagtgt acaccactgt gcctgctttg aatcctttac gaagagaaaa     1860
aaaaaattaa agaaagcctt tagatttatc caatgtttac tactgggatt gcttaaagtg     1920
aggcccctcc aacaccaggg ggttaattcc tgtgattgtg aaaggggcta cttccaaggc     1980
atcttcatgc aggcagcccc ttgggagggc acctgagagc tggtagagtc tgaaattagg     2040
gatgtgagcc tggtgacaag ggctcctgtt caatagtggt gttggggaga gagagagcag     2100
tgattataga ccgagagagt aggagttgag gtgaggtgaa ggaggtgctg ggggtgagaa     2160
tgtcgccttt cccctggt tttggatcac taattcaagg ctcttctgga tgtttctctg       2220 ggttgggct ggagttcaat gaggtttatt tttagctggc ccacccagat acactcagcc      2280 agaatacctta gatttagtac ccaaactctt cttagtctga aatctgctgg atttctggcc    2340
taagggagag gctcccatcc ttcgttcccc agccagccta ggacttcgaa tgtggagcct     2400
```

```
gaagatctaa gatcctaaca tgtacatttt atgtaaatat gtgcatattt gtacataaaa    2460
tgatattctg ttttaaata aacagacaaa acttgaaaaa aaaaaaaaa                 2510
```

<210> SEQ ID NO 42
<211> LENGTH: 897
<212> TYPE: DNA
<213> ORGANISM: Homo sapiens
<400> SEQUENCE: 42

```
aaaggcacaa cgtccagccg ttccttcaag cactcccgct ctgctgccgt cacctcagag     60
ttccacttgg tgcctagccg cagcatgaat gggcagccac tgacttgtgt ggtgtcccat    120
cctggcctgc tccaggacca aaggatcacc cacatcctcc acgtgtcctt ccttgctgag    180
gcctctgtga ggggccttga agaccaaaat ctgtggcaca ttggcagaga aggagctatg    240
ctcaagtgcc tgagtgaagg gcagccccct ccctcataca actggacacg gctggatggg    300
cctctgccca gtggggtacg agtggatggg gacactttgg gctttccccc actgaccact    360
gagcacagcg gcatctacgt ctgccatgtc agcaatgagt tctcctcaag ggattctcag    420
gtcactgtgg atgttcttgc agaccccccag gaagactctg ggaagcaggt ggacctagtg    480
tcagcctcgg tggtggtggt gggtgtgatc gccgcactct tgttctgcct tctggtggtg    540
gtggtggtgc tcatgtcccg ataccatcgg cgcaaggccc agcagatgac ccagaaaatt    600
gaggaggagc tgaccctgac cagggagaac tccatccgga ggctgcattc ccatcacacg    660
gaccccagga gccagagtga agagcccgag ggccgcagtt actccacgct gaccacggtg    720
agggagatag aaacacagac tgaactgctg tctccaggct ctgggcgggc cgaggaggag    780
gaagatcagg atgaaggcat caaacaggcc atgaaccatt ttgttcagga gaatgggacc    840
ctacgggcca agcccacggg caatggcatc tacatcaatg ggcggggaca cctggtc       897
```

<210> SEQ ID NO 43
<211> LENGTH: 299
<212> TYPE: PRT
<213> ORGANISM: Homo sapiens
<400> SEQUENCE: 43

```
Lys Gly Thr Thr Ser Arg Ser Phe Lys His Ser Arg Ser Ala Ala
1               5                   10                  15

Val Thr Ser Glu Phe His Leu Val Pro Ser Arg Ser Met Asn Gly Gln
            20                  25                  30

Pro Leu Thr Cys Val Val Ser His Pro Gly Leu Leu Gln Asp Gln Arg
        35                  40                  45

Ile Thr His Ile Leu His Val Ser Phe Leu Ala Glu Ala Ser Val Arg
    50                  55                  60

Gly Leu Glu Asp Gln Asn Leu Trp His Ile Gly Arg Glu Gly Ala Met
65                  70                  75                  80

Leu Lys Cys Leu Ser Glu Gly Gln Pro Pro Ser Tyr Asn Trp Thr
                85                  90                  95

Arg Leu Asp Gly Pro Leu Pro Ser Gly Val Arg Val Asp Gly Asp Thr
            100                 105                 110

Leu Gly Phe Pro Pro Leu Thr Thr Glu His Ser Gly Ile Tyr Val Cys
        115                 120                 125

His Val Ser Asn Glu Phe Ser Ser Arg Asp Ser Gln Val Thr Val Asp
    130                 135                 140

Val Leu Ala Asp Pro Gln Glu Asp Ser Gly Lys Gln Val Asp Leu Val
145                 150                 155                 160
```

```
Ser Ala Ser Val Val Val Gly Val Ile Ala Ala Leu Leu Phe Cys
            165                 170                 175
Leu Leu Val Val Val Val Leu Met Ser Arg Tyr His Arg Arg Lys
            180                 185                 190
Ala Gln Gln Met Thr Gln Lys Tyr Glu Glu Leu Thr Leu Thr Arg
            195                 200                 205
Glu Asn Ser Ile Arg Arg Leu His Ser His Thr Asp Pro Arg Ser
            210                 215                 220
Gln Ser Glu Glu Pro Glu Gly Arg Ser Tyr Ser Thr Leu Thr Thr Val
225                 230                 235                 240
Arg Glu Ile Glu Thr Gln Thr Glu Leu Leu Ser Pro Gly Ser Gly Arg
                    245                 250                 255
Ala Glu Glu Glu Asp Gln Asp Glu Gly Ile Lys Gln Ala Met Asn
                    260                 265                 270
His Phe Val Gln Glu Asn Gly Thr Leu Arg Ala Lys Pro Thr Gly Asn
                    275                 280                 285
Gly Ile Tyr Ile Asn Gly Arg Gly His Leu Val
        290                 295
```

<210> SEQ ID NO 44

<400> SEQUENCE: 44

000                                                                          3

<210> SEQ ID NO 45

<400> SEQUENCE: 45

000                                                                          3

<210> SEQ ID NO 46

<400> SEQUENCE: 46

000                                                                          3

<210> SEQ ID NO 47

<400> SEQUENCE: 47

000                                                                          3

<210> SEQ ID NO 48

<400> SEQUENCE: 48

000                                                                          3

<210> SEQ ID NO 49

<400> SEQUENCE: 49

000                                                                          3

<210> SEQ ID NO 50

<400> SEQUENCE: 50

000                                                                          3

<210> SEQ ID NO 51

<211> LENGTH: 3114
<212> TYPE: DNA
<213> ORGANISM: Homo sapiens

<400> SEQUENCE: 51

```
cttaatgttg aagtctctt agtcctatga gagtgtgtag cagtttgtcc ctgagctcta      60
gcttctttaa atgaagctga gtctctgggc aacatcttta gggagagagg tacaaaaggt     120
tcctggacct tctcaacaca gggagcctgc ataatgatgc aagagcagca acctcaaagt    180
acagagaaaa gaggctggtt gtccctgaga ctctggtctg tggctgggat tccattgca      240
ctcctcagtg cttgcttcat tgtgagctgt gtagtaactt accattttac atatggtgaa    300
actggcaaaa ggctgtctga actacactca tatcattcaa gtctcacctg cttcagtgaa    360
gggacaaagg tgccagcctg gggatgttgc ccagcttctt ggaagtcatt tggttccagt    420
tgctacttca tttccagtga agagaaggtt tggtctaaga gtgagcagaa ctgtgttgag    480
atgggagcac atttggttgt gttcaacaca gaagcagagc agaatttcat tgtccagcag    540
ctgaatgagt cattttctta ttttctgggg ctttcagacc cacaaggtaa taataattgg    600
caatggatta taagacacc ttatgagaaa aatgtcagat tttggcacct aggtgagccc      660
aatcattctg cagagcaatg tgcttcaata gtcttctgga aacctacagg atggggctgg    720
aatgatgtta tctgtgaaac tagaaggaat tcaatatgtg agatgaataa gatttaccta    780
tgagtagaag cttaattgga aagaagagaa gaattactga cgtaattttt tccctgacgt    840
ctttaaaatt gaaccctatc atgaaatgat aatttcttcc tgaatttaca cataatcctt    900
atgttataga ggttcacaga aatggaaaga tacctgtttc cctttaatca atcttctcgt    960
ttcctctttt ccattaatga tagaatgcac cctttcctctc tttgttccat tcttttcactt   1020
gttattcatt tttttctttc ttcacacttc attacacaaa tattattgt ttcagagact     1080
gtactatttt gtttgttaga agatttataa ggcagtatct tttgaaaatt atgactttcc    1140
ttcctcaata taccataaag aaatcttttt ggtcaagatg gtagttggaa ctacaatcat    1200
ctgaaggcct gacaagagtt gaaagacatg ttttctagat ggctcactca catggctggc    1260
aacttggtgt tggctattaa tgtaacctgg aaataaattt tattctgcag ttagggattt    1320
ggcatttttat atatgttgat tcaatcaagt ttggcaagca gggtgttcga tactgctata  1380
tcctgtattc ttggtttatt tgttttattt ctgagaaata tgtgttaaga tctctcgctg    1440
attgggaatt tgtctatttc tcatttaaat tttgtcaaat ctttctttgc ttgcaagcat    1500
ttcttgttac ccaaatctaa cctattcctg aaaatatgat ggttagcaaa gtttgagata    1560
actagagcct gtaatccatc attttaaatg gcaatgataa tgacagttta tttttatgtt    1620
atataaaaac ctcaacaaat tttccaaaca attaccaaaa tggtcattaa tctgtatcca    1680
caaaggattt ctgcattaca tactttaaaa caaattacct aattatttag tgcatattaa    1740
acttattggt gggcatgact atatgcaaca gttgcatgat atatgataca aattatgtta    1800
ttcttttcca ttgcactgaa ataccataaa tataagaag atcccatca tccaaattga     1860
gcctatattg attgatactc agaagaatct ggcagtagga gcctataaag ggataagcaa    1920
ttgggaaagg attgggaagt tggtagtact gaacatcttc tcacctggac tcatgagcaa   1980
cttgaatagt tgtaactgtg atgcatatgt agattctaac acattttcc ccttgaata      2040
gaaatttggc acaacaattt tttaaattaa tttagcaaat atttggatat taaagcttct   2100
tatagaaaga gataccgta tatttaagcc atgatgaggt atatacaatg ttataattat     2160
tacttgtaca tggcaaatta attttttttat cattgtggag tcactttctt taaatttagt   2220
```

-continued

```
aatgcctttg gctttaattt ttctcctgat attaaaatag atacagtaac tttcattatg    2280
ttagtgctgt aaaattttt  tttccatctt ctattttga  ccatttttat tccacatgtg    2340
ctcttaataa gtagcatata gttaaatttt aaaaaatcca atatggcaat caccttttag    2400
gttaaaaatt taatccattt acatttgtga caattcgaca tatatatggt tctaaatcta    2460
tcatcttact aggtggtttc catttcctct gctccaaaat attttttta  cagcttataa    2520 cacaactttt attagaaaag ttatacataa cacagcatca actattttca agaacccaat    2580
aagcaacaaa aaccagacta acaaaatgtg taacaagaaa ctaatgacct ttctaaaatc    2640
aaacattcaa ttatctacaa tgtctattta caaacaggga aaactccatg gtttacaggc    2700
atgtcatatt gaaataaag  ctgcaatagc ttttatatca attatcgctc tcaagaaaat    2760
gaatcattaa gacagtaatt aggagttcac aaatttaaaa catttcacgt aattttaaat    2820
tattgtcttc aataatttta aattattgaa gtctgagttt caaaagtgat tttttcccac    2880
aaaggtgcca acacttaagc tagagctttc agtgttaact ttgccctaaa agttaagaca    2940
tattctgaga atcataatag tcacatgatt tctgatgcta tctgctctgt taataacaaa    3000
gatttcacac atgaatacct atgtaacaaa tctccatgtt ctacacatat accccagaac    3060
ttaaagtata ataataataa aacatagcaa agcctttaaa aaaaaaaaaa aaaa          3114
```

<210> SEQ ID NO 52
<211> LENGTH: 627
<212> TYPE: DNA
<213> ORGANISM: Homo sapiens

<400> SEQUENCE: 52

```
atgatgcaag agcagcaacc tcaaagtaca gagaaaagag gctggttgtc cctgagactc      60
tggtctgtgg ctgggatttc cattgcactc ctcagtgctt gcttcattgt gagctgtgta     120
gtaacttacc attttacata tggtgaaact ggcaaaaggc tgtctgaact acactcatat     180
cattcaagtc tcacctgctt cagtgaaggg acaaaggtgc cagcctgggg atgttgccca     240
gcttcttgga agtcatttgg ttccagttgc tacttcattt ccagtgaaga gaaggtttgg     300
tctaagagtg agcagaactg tgttgagatg ggagcacatt tggttgtgtt caacacagaa     360
gcagagcaga atttcattgt ccagcagctg aatgagtcat tttcttattt tctggggctt     420
tcagacccac aagtaataa  taattggcaa tggattgata agacaccta  tgagaaaaat     480 gtcagatttt ggcacctagg tgagcccaat cattctgcag agcaatgtgc ttcaatagtc     540
ttctggaaac ctacaggatg gggctggaat gatgttatct gtgaaactag aaggaattca     600
atatgtgaga tgaataagat ttaccta                                         627
```

<210> SEQ ID NO 53
<211> LENGTH: 209
<212> TYPE: PRT
<213> ORGANISM: Homo sapiens

<400> SEQUENCE: 53

```
Met Met Gln Glu Gln Gln Pro Gln Ser Thr Glu Lys Arg Gly Trp Leu
 1               5                  10                  15

Ser Leu Arg Leu Trp Ser Val Ala Gly Ile Ser Ile Ala Leu Leu Ser
            20                  25                  30

Ala Cys Phe Ile Val Ser Cys Val Val Thr Tyr His Phe Thr Tyr Gly
        35                  40                  45

Glu Thr Gly Lys Arg Leu Ser Glu Leu His Ser Tyr His Ser Ser Leu
```

```
                 50                  55                  60
Thr Cys Phe Ser Glu Gly Thr Lys Val Pro Ala Trp Gly Cys Cys Pro
 65                  70                  75                  80

Ala Ser Trp Lys Ser Phe Gly Ser Ser Cys Tyr Phe Ile Ser Ser Glu
                 85                  90                  95

Glu Lys Val Trp Ser Lys Ser Glu Gln Asn Cys Val Glu Met Gly Ala
                100                 105                 110

His Leu Val Val Phe Asn Thr Glu Ala Glu Gln Asn Phe Ile Val Gln
                115                 120                 125

Gln Leu Asn Glu Ser Phe Ser Tyr Phe Leu Gly Leu Ser Asp Pro Gln
                130                 135                 140

Gly Asn Asn Asn Trp Gln Trp Ile Asp Lys Thr Pro Tyr Glu Lys Asn
145                 150                 155                 160

Val Arg Phe Trp His Leu Gly Glu Pro Asn His Ser Ala Glu Gln Cys
                165                 170                 175

Ala Ser Ile Val Phe Trp Lys Pro Thr Gly Trp Gly Trp Asn Asp Val
                180                 185                 190

Ile Cys Glu Thr Arg Arg Asn Ser Ile Cys Glu Met Asn Lys Ile Tyr
                195                 200                 205

Leu

<210> SEQ ID NO 54
<211> LENGTH: 48
<212> TYPE: PRT
<213> ORGANISM: Homo sapiens

<400> SEQUENCE: 54

Met Met Gln Glu Gln Gln Pro Gln Ser Thr Glu Lys Arg Gly Trp Leu
 1               5                  10                  15

Ser Leu Arg Leu Trp Ser Val Ala Gly Ile Ser Ile Ala Leu Leu Ser
                20                  25                  30

Ala Cys Phe Ile Val Ser Cys Val Val Thr Tyr His Phe Thr Tyr Gly
                35                  40                  45

<210> SEQ ID NO 55
<211> LENGTH: 161
<212> TYPE: PRT
<213> ORGANISM: Homo sapiens

<400> SEQUENCE: 55

Glu Thr Gly Lys Arg Leu Ser Glu Leu His Ser Tyr His Ser Ser Leu
 1               5                  10                  15

Thr Cys Phe Ser Glu Gly Thr Lys Val Pro Ala Trp Gly Cys Cys Pro
                20                  25                  30

Ala Ser Trp Lys Ser Phe Gly Ser Ser Cys Tyr Phe Ile Ser Ser Glu
                35                  40                  45

Glu Lys Val Trp Ser Lys Ser Glu Gln Asn Cys Val Glu Met Gly Ala
                50                  55                  60

His Leu Val Val Phe Asn Thr Glu Ala Glu Gln Asn Phe Ile Val Gln
 65                  70                  75                  80

Gln Leu Asn Glu Ser Phe Ser Tyr Phe Leu Gly Leu Ser Asp Pro Gln
                85                  90                  95

Gly Asn Asn Asn Trp Gln Trp Ile Asp Lys Thr Pro Tyr Glu Lys Asn
                100                 105                 110

Val Arg Phe Trp His Leu Gly Glu Pro Asn His Ser Ala Glu Gln Cys
                115                 120                 125
```

```
Ala Ser Ile Val Phe Trp Lys Pro Thr Gly Trp Gly Trp Asn Asp Val
            130                 135                 140

Ile Cys Glu Thr Arg Arg Asn Ser Ile Cys Glu Met Asn Lys Ile Tyr
145                 150                 155                 160

Leu
```

<210> SEQ ID NO 56

<400> SEQUENCE: 56

000                                                                     3

<210> SEQ ID NO 57

<400> SEQUENCE: 57

000                                                                     3

<210> SEQ ID NO 58

<400> SEQUENCE: 58

000                                                                     3

<210> SEQ ID NO 59

<400> SEQUENCE: 59

000                                                                     3

<210> SEQ ID NO 60
<211> LENGTH: 209
<212> TYPE: PRT
<213> ORGANISM: Mus sp.

<400> SEQUENCE: 60

```
Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Ser Thr Cys
            20                  25                  30

Phe Ile Ala Ser Cys Val Val Thr Tyr Gln Phe Ile Met Asp Gln Pro
            35                  40                  45

Ser Arg Arg Leu Tyr Glu Leu His Thr Tyr His Ser Ser Leu Thr Cys
    50                  55                  60

Phe Ser Glu Gly Thr Met Val Ser Glu Lys Met Trp Gly Cys Cys Pro
65                  70                  75                  80

Asn His Trp Lys Ser Phe Gly Ser Ser Cys Tyr Leu Ile Ser Thr Lys
                85                  90                  95

Glu Asn Phe Trp Ser Thr Ser Glu Gln Asn Cys Val Gln Met Gly Ala
            100                 105                 110

His Leu Val Val Ile Asn Thr Glu Ala Glu Gln Asn Phe Ile Thr Gln
            115                 120                 125

Gln Leu Asn Glu Ser Leu Ser Tyr Phe Leu Gly Leu Ser Asp Pro Gln
        130                 135                 140

Gly Asn Gly Lys Trp Gln Trp Ile Asp Asp Thr Pro Phe Ser Gln Asn
145                 150                 155                 160

Val Arg Phe Trp His Pro His Glu Pro Asn Leu Pro Glu Glu Arg Cys
                165                 170                 175

Val Ser Ile Val Tyr Trp Asn Pro Ser Lys Trp Gly Trp Asn Asp Val
```

```
              180                 185                 190
         Phe Cys Asp Ser Lys His Asn Ser Ile Cys Glu Met Lys Lys Ile Tyr
             195                 200                 205
         Leu

<210> SEQ ID NO 61
<211> LENGTH: 821
<212> TYPE: DNA
<213> ORGANISM: Mus sp.
<220> FEATURE:
<221> NAME/KEY: misc_feature
<222> LOCATION: (788)..(788)
<223> OTHER INFORMATION: unsure

<400> SEQUENCE: 61
gaactccccg gtgtcgaccc cgcgtcccga ttggcccgct ctgtggcatt taactcaagt      60
gtgtgtggaa gttgattctg aactctggcc tctttgacag aagccaggtc cctgagtcgt     120
attttggaga cagatgcaag aaaccccctga ccttctgaac atacacctca acaatggtgc    180
aggaaagaca atcccaaggg aagggagtct gctggaccct gagactctgg tcagctgctg    240
tgatttccat gttactcttg agtacctgtt tcattgcgag ctgtgtggtg acttaccaat    300
ttattatgga ccagcccagt agaagactat atgaacttca cacataccat tccagtctca    360
cctgcttcag tgaagggact atggtgtcag aaaaaatgtg gggatgctgc ccaaatcact    420
ggaagtcatt tggctccagc tgctacctca tttctaccaa ggagaacttc tggagcacca    480
gtgagcagaa ctgtgttcag atgggggctc atctggtggt gatcaatact gaagcggagc    540
agaatttcat cacccagcag ctgaatgagt cactttctta cttcctgggt ctttcggatc    600
ccaaggtaat ggcaaatggc aatggatcga tgatactcct tcagtcaaa atgtcaggtt     660 ctggcacccc catgaaccca atcttccaga gagcggtgt gtttcaatag tttactggaa     720
tccttcgaaa tggggctggg aatgatgttt tctgtgatga taaacacaat tcaatatgtg    780
aaatgaanaa gattacctat gaatgcctgt tattcttaat a                         821
```

<210> SEQ ID NO 62
<211> LENGTH: 534
<212> TYPE: DNA
<213> ORGANISM: Mus sp.

<400> SEQUENCE: 62

```
atggtgcagg aaagacaatc ccaagggaag ggagtctgct ggaccctgag actctggtca      60
gctgctgtga tttccatgtt actcttgagt acctgtttca ttgcgagctg tgtggtgact     120
taccaattta ttatggacca gcccagtaga agactatatg aacttcacac ataccattcc    180
agtctcacct gcttcagtga agggactatg gtgtcagaaa aaatgggggg atgctgccca    240
atcactggaa gtcatttggc tccagctgc tacctcattt ctaccaagga gaacttctgg     300
agcaccagtg agcagaactg tgttcagatg ggggctcatc tggtggtgat caatactgaa    360
gcggagcaga atttcatcac ccagcagctg aatgagtcac tttcttactt cctgggtctt    420
tcggatccca aggtaatggc aaatggcaat ggatcgatga tactcctttc agtcaaaatg    480
tcaggttctg gcaccccat gaacccaatc ttccagaaga gcggtgtgtt tcaa            534
```

<210> SEQ ID NO 63
<211> LENGTH: 178
<212> TYPE: PRT
<213> ORGANISM: Mus sp.

```
<400> SEQUENCE: 63

Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Ser Thr Cys
                20                  25                  30

Phe Ile Ala Ser Cys Val Val Thr Tyr Gln Phe Ile Met Asp Gln Pro
            35                  40                  45

Ser Arg Arg Leu Tyr Glu Leu His Thr Tyr His Ser Ser Leu Thr Cys
50                  55                  60

Phe Ser Glu Gly Thr Met Val Ser Glu Lys Met Trp Gly Cys Cys Pro
65                  70                  75                  80

Asn His Trp Lys Ser Phe Gly Ser Ser Cys Tyr Leu Ile Ser Thr Lys
                85                  90                  95

Glu Asn Phe Trp Ser Thr Ser Glu Gln Asn Cys Val Gln Met Gly Ala
            100                 105                 110

His Leu Val Val Ile Asn Thr Glu Ala Glu Gln Asn Phe Ile Thr Gln
        115                 120                 125

Gln Leu Asn Glu Ser Leu Ser Tyr Phe Leu Gly Leu Ser Asp Pro Lys
130                 135                 140

Val Met Ala Asn Gly Asn Gly Ser Met Ile Leu Leu Ser Val Lys Met
145                 150                 155                 160

Ser Gly Ser Gly Thr Pro Met Asn Pro Ile Phe Gln Lys Ser Gly Val
                165                 170                 175

Phe Gln

<210> SEQ ID NO 64
<211> LENGTH: 48
<212> TYPE: PRT
<213> ORGANISM: Mus sp.

<400> SEQUENCE: 64

Met Val Gln Glu Arg Gln Ser Gln Gly Lys Gly Val Cys Trp Thr Leu
1               5                   10                  15

Arg Leu Trp Ser Ala Ala Val Ile Ser Met Leu Leu Ser Thr Cys
                20                  25                  30

Phe Ile Ala Ser Cys Val Val Thr Tyr Gln Phe Ile Met Asp Gln Pro
            35                  40                  45

<210> SEQ ID NO 65
<211> LENGTH: 130
<212> TYPE: PRT
<213> ORGANISM: Mus sp.

<400> SEQUENCE: 65

Ser Arg Arg Leu Tyr Glu Leu His Thr Tyr His Ser Ser Leu Thr Cys
1               5                   10                  15

Phe Ser Glu Gly Thr Met Val Ser Glu Lys Met Trp Gly Cys Cys Pro
            20                  25                  30

Asn His Trp Lys Ser Phe Gly Ser Ser Cys Tyr Leu Ile Ser Thr Lys
        35                  40                  45

Glu Asn Phe Trp Ser Thr Ser Glu Gln Asn Cys Val Gln Met Gly Ala
    50                  55                  60

His Leu Val Val Ile Asn Thr Glu Ala Glu Gln Asn Phe Ile Thr Gln
65                  70                  75                  80

Gln Leu Asn Glu Ser Leu Ser Tyr Phe Leu Gly Leu Ser Asp Pro Lys
                85                  90                  95
```

```
Val Met Ala Asn Gly Asn Gly Ser Met Ile Leu Leu Ser Val Lys Met
            100                 105                 110
Ser Gly Ser Gly Thr Pro Met Asn Pro Ile Phe Gln Lys Ser Gly Val
        115                 120                 125
Phe Gln
    130

<210> SEQ ID NO 66

<400> SEQUENCE: 66

000                                                                       3

<210> SEQ ID NO 67

<400> SEQUENCE: 67

000                                                                       3

<210> SEQ ID NO 68

<400> SEQUENCE: 68

000                                                                       3

<210> SEQ ID NO 69

<400> SEQUENCE: 69

000                                                                       3

<210> SEQ ID NO 70

<400> SEQUENCE: 70

000                                                                       3

<210> SEQ ID NO 71
<211> LENGTH: 1252
<212> TYPE: DNA
<213> ORGANISM: Mus sp.

<400> SEQUENCE: 71
cgaccccgcg tccgctgact tctgggtttg cagcattggc ccgctctgtg gcatttaact    60
caagtgtgtg tggaagttga ttctgaactc tggcctcttt gacagaagcc aggtccctga   120
gtcgtatttt ggagacagat gcaagaaacc cctgaccttc tgaacataca cctcaacaat   180
ggtgcaggaa agacaatccc aagggaaggg agtctgctgg accctgagac tctggtcagc   240
tgctgtgatt ccatgttac  tcttgagtac ctgtttcatt gcgagctgtg tggtgactta   300
ccaatttatt atggaccagc ccagtagaag actatatgaa cttcacacat accattccag   360
tctcacctgc ttcagtgaag ggactatggt gtcagaaaaa atgtggggat gctgcccaaa   420
tcactggaag tcatttggct ccagctgcta cctcatttct accaaggaga acttctggag   480
caccagtgag cagaactgtg ttcagatggg ggctcatctg gtggtgatca atactgaagc   540
ggagcagaat tcatcaccc  agcagctgaa tgagtcactt tcttacttcc tgggtctttc   600
ggatccacaa ggtaatggca atggcaatg  gatcgatgat actcctttca gtcaaaatgt   660
caggttctgg caccccatg  aacccaatct tccagaagag cggtgtgttt caatagttta   720
ctggaatcct tcgaaatggg gctggaatga tgttttctgt gatagtaaac acaattcaat   780
```

```
atgtgaaatg aagaagattt acctatgagt gcctgttatt cattaatatc tttaaagttc      840
agacctacca agaagccata acttcttggc ctgtacatct gacagaggcc gttcttttcc      900
tagccactat tctttactca aacagaatga gcccttctc cttctgatgg ttagagtttt       960
gtcaacttga cacaaactag agtcacctgg ggagtaggat cttcagctaa ggaattgcct     1020
ctgtcagctt gaccagtcag catgtctggg ggcattttct tgattaatga ttgttgtaag     1080
agggtccagg tggtaagcaa aggtgttaaa cccatgaaga gcaagccagg gagcatcatc     1140
catccatctc tgccctcagg tttctgcccc agggtcttgc cctggtttct ttctatgaac     1200
tgctgttact tgaaagtata agatgaataa acaatttcat ccaaaaaaaa aa             1252
```

<210> SEQ ID NO 72
<211> LENGTH: 627
<212> TYPE: DNA
<213> ORGANISM: Mus sp.

<400> SEQUENCE: 72

```
atggtgcagg aaagacaatc ccaagggaag ggagtctgct ggaccctgag actctggtca       60
gctgctgtga tttccatgtt actcttgagt acctgtttca ttgcgagctg tgtggtgact      120
taccaattta ttatggacca gcccagtaga agactatatg aacttcacac ataccattcc      180
agtctcacct gcttcagtga aggactatg gtgtcagaaa aaatgtgggg atgctgccca       240
atcactgga agtcatttgg ctccagctgc tacctcattt ctaccaagga gaacttctgg       300
agcaccagtg agcagaactg tgttcagatg ggggctcatc tggtggtgat caatactgaa      360
gcggagcaga atttcatcac ccagcagctg aatgagtcac tttcttactt cctgggtctt      420
tcggatccac aagtaatgg caaatggcaa tggatcgatg atactccttt cagtcaaaat      480
gtcaggttct ggcaccccca tgaacccaat cttccagaag agcggtgtgt ttcaatagtt      540
tactggaatc cttcgaaatg gggctggaat gatgttttct gtgatagtaa acacaattca      600
atatgtgaaa tgaagaagat ttaccta                                         627
```

<210> SEQ ID NO 73
<211> LENGTH: 586
<212> TYPE: PRT
<213> ORGANISM: Mus sp.

<400> SEQUENCE: 73

Met Glu Thr Val Ala Leu Gly Leu Asn Gly Leu Ala Arg Gly Gly Leu
1               5                   10                  15

Asn Ser Glu Arg Gly Leu Asn Gly Leu Tyr Leu Tyr Ser Gly Leu Tyr
                20                  25                  30

Val Ala Leu Cys Tyr Ser Thr Arg Pro Thr His Arg Leu Glu Ala Arg
            35                  40                  45

Gly Leu Glu Thr Arg Pro Ser Glu Arg Ala Leu Ala Ala Leu Ala Val
        50                  55                  60

Ala Leu Ile Leu Glu Ser Glu Arg Met Glu Thr Leu Glu Leu Glu Leu
65                  70                  75                  80

Glu Ser Glu Arg Thr His Arg Cys Tyr Ser Pro His Glu Ile Leu Glu
                85                  90                  95

Ala Leu Ala Ser Glu Arg Cys Tyr Ser Val Ala Leu Val Ala Leu Thr
            100                 105                 110

His Arg Thr Tyr Arg Gly Leu Asn Pro His Glu Ile Leu Glu Met Glu
        115                 120                 125

Thr Ala Ser Pro Gly Leu Asn Pro Arg Ser Glu Arg Ala Arg Gly Ala

-continued

```
                130                 135                 140
Arg Gly Leu Glu Thr Tyr Arg Gly Leu Leu Glu His Ile Ser Thr His
145                 150                 155                 160
Arg Thr Tyr Arg His Ile Ser Ser Glu Arg Ser Glu Arg Leu Glu Thr
                165                 170                 175
His Arg Cys Tyr Ser Pro His Glu Ser Glu Arg Gly Leu Gly Leu Tyr
                180                 185                 190
Thr His Arg Met Glu Thr Val Ala Leu Ser Glu Arg Gly Leu Leu Tyr
                195                 200                 205
Ser Met Glu Thr Thr Arg Pro Gly Leu Tyr Cys Tyr Ser Cys Tyr Ser
210                 215                 220
Pro Arg Ala Ser Asn His Ile Ser Thr Arg Pro Leu Tyr Ser Ser Glu
225                 230                 235                 240
Arg Pro His Glu Gly Leu Tyr Ser Glu Arg Ser Glu Arg Cys Tyr Ser
                245                 250                 255
Thr Tyr Arg Leu Glu Ile Leu Glu Ser Glu Arg Thr His Arg Leu Tyr
                260                 265                 270
Ser Gly Leu Ala Ser Asn Pro His Glu Thr Arg Pro Ser Glu Arg Thr
            275                 280                 285
His Arg Ser Glu Arg Gly Leu Gly Leu Asn Ala Ser Asn Cys Tyr Ser
            290                 295                 300
Val Ala Leu Gly Leu Asn Met Glu Thr Gly Leu Tyr Ala Leu Ala His
305                 310                 315                 320
Ile Ser Leu Glu Val Ala Leu Val Ala Leu Ile Leu Glu Ala Ser Asn
                325                 330                 335
Thr His Arg Gly Leu Ala Leu Ala Gly Leu Gly Leu Asn Ala Ser Asn
                340                 345                 350
Pro His Glu Ile Leu Glu Thr His Arg Gly Leu Asn Gly Leu Asn Leu
            355                 360                 365
Glu Ala Ser Asn Gly Leu Ser Glu Arg Leu Glu Ser Glu Arg Thr Tyr
            370                 375                 380
Arg Pro His Glu Leu Glu Gly Leu Tyr Leu Glu Ser Glu Arg Ala Ser
385                 390                 395                 400
Pro Pro Arg Gly Leu Asn Gly Leu Tyr Ala Ser Asn Gly Leu Tyr Leu
                405                 410                 415
Tyr Ser Thr Arg Pro Gly Leu Asn Thr Arg Pro Ile Leu Glu Ala Ser
                420                 425                 430
Pro Ala Ser Pro Thr His Arg Pro Arg Pro His Glu Ser Glu Arg Gly
            435                 440                 445
Leu Asn Ala Ser Asn Val Ala Leu Ala Arg Gly Pro His Glu Thr Arg
450                 455                 460
Pro His Ile Ser Pro Arg His Ile Ser Gly Leu Pro Arg Ala Ser Asn
465                 470                 475                 480
Leu Glu Pro Arg Gly Leu Gly Leu Ala Arg Gly Cys Tyr Ser Val Ala
                485                 490                 495
Leu Ser Glu Arg Ile Leu Glu Val Ala Leu Thr Tyr Arg Trp Ala Ser
                500                 505                 510
Asn Pro Arg Ser Glu Arg Leu Tyr Ser Thr Arg Pro Gly Leu Tyr Thr
                515                 520                 525
Arg Pro Ala Ser Asn Ala Ser Pro Val Ala Leu Phe Cys Tyr Ser Ala
                530                 535                 540
Ser Pro Ser Glu Arg Leu Tyr Ser His Ile Ser Ala Ser Asn Ser Glu
545                 550                 555                 560
```

```
            Arg Ile Leu Glu Cys Tyr Ser Gly Leu Met Glu Thr Leu Tyr Ser Leu
                            565                 570                 575

Tyr Ser Ile Leu Glu Thr Tyr Arg Leu Glu
                            580                 585

<210> SEQ ID NO 74

<400> SEQUENCE: 74

000                                                                       3

<210> SEQ ID NO 75

<400> SEQUENCE: 75

000                                                                       3

<210> SEQ ID NO 76

<400> SEQUENCE: 76

000                                                                       3

<210> SEQ ID NO 77

<400> SEQUENCE: 77

000                                                                       3

<210> SEQ ID NO 78

<400> SEQUENCE: 78

000                                                                       3

<210> SEQ ID NO 79

<400> SEQUENCE: 79

000                                                                       3

<210> SEQ ID NO 80

<400> SEQUENCE: 80

000                                                                       3

<210> SEQ ID NO 81
<211> LENGTH: 1202
<212> TYPE: DNA
<213> ORGANISM: Homo sapiens

<400> SEQUENCE: 81
gtcgacccac gcgtccggaa accattccac aatcaccctc ctgaggaact cttagcactg      60
cataaagtgt tctgagtttg taatcagata ttgtcacact ggttccttca aacagacatg     120
acaaggagct ggctttgggc taggctgctc cttgcctatg attggggaag gttaaacccc     180
tacagggctt atgtatgtgg aaactgttgg aacactgatt aaatgggatg gacttcactt     240
aacactcttg gatttccaat attatgtttg agtaaaagaa ctgctatcca caaacaccat     300
taatccttta gggaggcaga aaaggccaga atgcaaagcc atcttttcat tacactaggg     360
tctgtctttt tacttctctg ggcctttatc tggggagggc atgttccccc cacttggaac     420
agtgagcctg gccaggacag taacctgtgg gcttgtgatg acattatttc taatagggaa     480
```

```
tgggaaagga tgttagcttc tcaggtttta aagtgtcctg aggagaaga gaaaggacga      540 catgagaagg agacaatgaa gaagatgggt gaggggggaga tagtgtaaga ccctgagaat     600
ggcatagggt aaaactggga cagagatact gtgggagaac gatagctgca gagggacaga     660
gggaggaagg aaggagaaga gagggagata aaaacagttt ggagaaactc tcacaataca     720
ttcataagaa gacaaagaac ccaataaaaa tgggcaacag ataccacaga agatgatata     780
ttgagtggcc aataaataca taaaaatatg ctcaacatct ataattacca gggaaatgca     840
aattaaaagc actgtgagat accactacac actgatgaga atggctaaaa tcaaaaaaga     900
ccaaccagca ctttgggagg ccgaggtggg cggatcatga ggtcaggagt ttgagactag     960
cctgaccaac atggtgaaac cctgtctcta ctaaacatac aaaaattagc tgggggtggt    1020
ggcatgcgcc tgtaattcca gctactcagg aggctgaggc aggagaatcg cttgaaccca    1080
ggaggcagag attacagtga gccgagatca tgcccttgca ctctagcctg ggtgacagag    1140
cgagactctg tcttaaaaaa aaaaaaaaaa aaaaaaaaaa aaaaaaaaa aagggcggcc    1200 gc                                                                   1202

<210> SEQ ID NO 82
<211> LENGTH: 255
<212> TYPE: DNA
<213> ORGANISM: Homo sapiens

<400> SEQUENCE: 82
atgcaaagcc atcttttcat tacactaggg tctgtctttt tacttctctg ggcctttatc       60
tggggagggc atgtttcccc cacttggaac agtgagcctg ccaggacag taacctgtgg      120 gcttgtgatg acattatttc taatagggaa tgggaaagga tgttagcttc tcaggtttta     180
aagtgtcctg aggagaaga gaaaggacga catgagaagg agacaatgaa gaagatgggt      240
gaggggagaa tagtg                                                       255

<210> SEQ ID NO 83
<211> LENGTH: 85
<212> TYPE: PRT
<213> ORGANISM: Homo sapiens

<400> SEQUENCE: 83

Met Gln Ser His Leu Phe Ile Thr Leu Gly Ser Val Phe Leu Leu Leu
1               5                   10                  15

Trp Ala Phe Ile Trp Gly Gly His Val Ser Pro Thr Trp Asn Ser Glu
            20                  25                  30

Pro Gly Gln Asp Ser Asn Leu Trp Ala Cys Asp Asp Ile Ile Ser Asn
        35                  40                  45

Arg Glu Trp Glu Arg Met Leu Ala Ser Gln Val Leu Lys Cys Pro Gly
    50                  55                  60

Gly Glu Glu Lys Gly Arg His Glu Lys Glu Thr Met Lys Lys Met Gly
65                  70                  75                  80

Glu Gly Glu Ile Val
                85

<210> SEQ ID NO 84
<211> LENGTH: 23
<212> TYPE: PRT
<213> ORGANISM: Homo sapiens

<400> SEQUENCE: 84
```

-continued

```
Met Gln Ser His Leu Phe Ile Thr Leu Gly Ser Val Phe Leu Leu Leu
1               5                   10                  15

Trp Ala Phe Ile Trp Gly Gly
            20

<210> SEQ ID NO 85
<211> LENGTH: 62
<212> TYPE: PRT
<213> ORGANISM: Homo sapiens

<400> SEQUENCE: 85

His Val Ser Pro Thr Trp Asn Ser Glu Pro Gly Gln Asp Ser Asn Leu
1               5                   10                  15

Trp Ala Cys Asp Asp Ile Ile Ser Asn Arg Glu Trp Glu Arg Met Leu
            20                  25                  30

Ala Ser Gln Val Leu Lys Cys Pro Gly Gly Glu Glu Lys Gly Arg His
            35                  40                  45

Glu Lys Glu Thr Met Lys Lys Met Gly Glu Gly Glu Ile Val
    50                  55                  60
```

NUCLEIC ACIDS ENCODING TANGO405 AND FUNCTIONAL FRAGMENTS AND USES THEREOF

CROSS-REFERENCE TO RELATED APPLICATIONS

This application is a continuation-in-part of U.S. patent application Ser. No. 09/578,063, filed on May 24, 2000, now U.S. Pat. No. 6,764,677, which is a continuation-in-part of U.S. patent application Ser. No. 09/333,159, filed on Jun. 14, 1999, now U.S. Pat. No. 7,033,780.

This application is also a continuation-in-part of U.S. patent application Ser. No. 09/596,194, filed on Jun. 16, 2000, now abandoned, which is a continuation-in-part of U.S. patent application Ser. No. 09/342,364, filed on Jun. 29, 1999, now abandoned.

This application is also a continuation-in-part of U.S. patent application Ser. No. 09/608,452, filed on Jun. 30, 2000, now abandoned, which is a continuation-in-part of U.S. patent application Ser. No. 09/393,996, filed on Sep. 10, 1999, now abandoned.

This application is also a continuation-in-part of U.S. patent application Ser. No. 09/345,680, filed on Jun. 30, 1999, now abandoned.

The contents of each of the applications cross-referenced in this section are incorporated into this disclosure by reference.

STATEMENT REGARDING FEDERAL RESEARCH SUPPORT

Not Applicable

REFERENCE TO MICROFICHE APPENDIX

Not Applicable

BACKGROUND OF THE INVENTION

The molecular bases underlying many human and animal physiological states (e.g., diseased and homeostatic states of various tissues) remain unknown. Nonetheless, it is well understood that these states result from interactions among the proteins and nucleic acids present in the cells of the relevant tissues. In the past, the complexity of biological systems overwhelmed the ability of practitioners to understand the molecular interactions giving rise to normal and abnormal physiological states. More recently, though, the techniques of molecular biology, transgenic and null mutant animal production, computational biology, and pharmacogenomics have enabled practitioners to discern the role and importance of individual genes and proteins in particular physiological states.

Knowledge of the sequences and other properties of genes (particularly including the portions of genes encoding proteins) and the proteins encoded thereby enables the practitioner to design and screen agents which will affect, prospectively or retrospectively, the physiological state of an animal tissue in a favorable way. Such knowledge also enables the practitioner, by detecting the levels of gene expression and protein production, to diagnose the current physiological state of a tissue or animal and to predict such physiological states in the future. This knowledge furthermore enables the practitioner to identify and design molecules which bind with the polynucleotides and proteins, in vitro, in vivo, or both.

Many secreted proteins, for example, cytokines and cytokine receptors, play a vital role in the regulation of cell growth, cell differentiation, and a variety of specific cellular responses. A number of medically useful proteins, including erythropoietin, granulocyte-macrophage colony stimulating factor, human growth hormone, and various interleukins, are secreted proteins. Thus, an important goal in the design and development of new therapies is the identification and characterization of secreted and transmembrane proteins and the genes which encode them.

Many secreted proteins are receptors which bind a ligand and transduce an intracellular signal, leading to a variety of cellular responses. The identification and characterization of such a receptor enables one to identify both the ligands which bind to the receptor and the intracellular molecules and signal transduction pathways associated with the receptor, permitting one to identify or design modulators of receptor activity, e.g., receptor agonists or antagonists and modulators of signal transduction.

SUMMARY OF THE INVENTION

The present invention is based, at least in part, on the discovery of human cDNA molecules which encode proteins which are herein designated TANGO 273, TANGO 325, TANGO 364, TANGO 405, and M019 (M019 is synonymous with TANGO 533). These proteins, fragments thereof, derivatives thereof, and variants thereof are collectively referred to herein as the polypeptides of the invention or the proteins of the invention. Nucleic acid molecules encoding polypeptides of the invention are collectively referred to as nucleic acids of the invention.

The nucleic acids and polypeptides of the present invention are useful as modulating agents for regulating a variety of cellular processes. Accordingly, in one aspect, the present invention provides isolated nucleic acid molecules encoding a polypeptide of the invention or a biologically active portion thereof. The present invention also provides nucleic acid molecules which are suitable as primers or hybridization probes for the detection of nucleic acids encoding a polypeptide of the invention.

The invention also includes fragments of any of the nucleic acids described herein wherein the fragment retains a biological or structural function by which the full-length nucleic acid is characterized (e.g., an activity, an encoded protein, or a binding capacity). The invention furthermore includes fragments of any of the nucleic acids described herein wherein the fragment has a nucleotide sequence sufficiently (e.g., 50%, 60%, 70%, 80%, 85%, 90%, 95%, 98%, or 99% or greater) identical to the nucleotide sequence of the corresponding full-length nucleic acid that it retains a biological or structural function by which the full-length nucleic acid is characterized (e.g., an activity, an encoded protein, or a binding capacity).

The invention also includes fragments of any of the polypeptides described herein wherein the fragment retains a biological or structural function by which the full-length polypeptide is characterized (e.g., an activity or a binding capacity). The invention furthermore includes fragments of any of the polypeptides described herein wherein the fragment has an amino acid sequence sufficiently (e.g., 50%, 60%, 70%, 80%, 85%, 90%, 95%, 98%, or 99% or greater) identical to the amino acid sequence of the corresponding full-length polypeptide that it retains a biological or structural function by which the full-length polypeptide is characterized (e.g., an activity or a binding capacity).

The invention also features nucleic acid molecules which are at least 40% (or 50%, 60%, 70%, 80%, 90%, 95%, or 98%) identical to the nucleotide sequence of any of SEQ ID NOs: 1, 2, 11, 12, 21, 22, 31, 32, 41, 42, 51, 52, 61, 62, 71, 72, 81, and 82, the human TANGO 273 nucleotide sequence of the cDNA insert of a clone deposited on Apr. 2, 1999 with the American Type Culture Collection® (ATCC®) as accession no. 207185, the murine TANGO 273 nucleotide sequence of the cDNA insert of a clone deposited on Apr. 2, 1999 with ATCC® as accession no. 207221, the human TANGO 325 nucleotide sequence of the cDNA insert of a clone deposited on May 28, 1999 with ATCC® as accession no. PTA-147, the human TANGO 364 nucleotide sequence of the cDNA insert of a clone deposited on Jul. 23, 1999 with ATCC® as accession no. PTA-425, the human TANGO 405 nucleotide sequence of the cDNA insert of a clone deposited on Jul. 23, 1999 with ATCC® as accession no. PTA-424, or a complement thereof. These deposited nucleotide sequences are hereafter individually and collectively referred to as "the nucleotide sequence of any of the clones deposited as ATCC® Accession numbers 207185, 207221, PTA-147, PTA-425, and PTA-424."

The invention features nucleic acid molecules which include a fragment of at least 15 (25, 40, 60, 80, 100, 150, 200, 250, 300, 350, 400, 450, 500, 600, 700, 800, 900, 1000, 1200, 1400, 1600, 1800, 2000, 2200, 2400, 2600, 2800, 3000, or 3500 or more) consecutive nucleotide residues of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or a complement thereof.

The invention also features nucleic acid molecules which include a nucleotide sequence encoding a protein having an amino acid sequence that is at least 50% (or 60%, 70%, 80%, 90%, 95%, or 98%) identical to the amino acid sequence of any of SEQ ID NOs: 3–8, 13–18, 23–28, 33–38, 43, 53–55, 63–65, 73, and 83–85, or the amino acid sequence encoded by the nucleotide sequence of any of the clones deposited as ATCC® Accession numbers 207185, 207221, PTA-147, PTA-425, and PTA-424, or a complement thereof.

In certain embodiments, the nucleic acid molecules have the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424.

Also within the invention are nucleic acid molecules which encode a fragment of a polypeptide having the amino acid sequence of any of SEQ ID NOs: 3–8, 13–18, 23–28, 33–38, 43, 53–55, 63–65, 73, and 83–85, the fragment including at least 10 (12, 15, 20, 25, 30, 40, 50, 75, 100, 125, 150, 200, 250, 300, 400, 500, 750, 1000 or more) consecutive amino acid residues of any of SEQ ID NOs: 3–8, 13–18, 23–28, 33–38, 43, 53–55, 63–65, 73, and 83–85.

The invention includes nucleic acid molecules which encode a naturally occurring allelic variant of a polypeptide comprising the amino acid sequence of any of SEQ ID NOs: 3–8, 13–18, 23–28, 33–38, 43, 53–55, 63–65, 73, and 83–85, wherein the nucleic acid molecule hybridizes under stringent conditions to a nucleic acid molecule having a nucleic acid sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or a complement thereof.

Also within the invention are isolated polypeptides or proteins having an amino acid sequence that is at least about 50%, preferably 60%, 75%, 90%, 95%, or 98% identical to the amino acid sequence of any of SEQ ID NOs: 3–8, 13–18, 23–28, 33–38, 43, 53–55, 63–65, 73, and 83–85.

Also within the invention are isolated polypeptides or proteins which are encoded by a nucleic acid molecule having a nucleotide sequence that is at least about 40%, preferably 50%, 60%, 75%, 85%, or 95% identical to the nucleic acid sequence encoding any of SEQ ID NOs: 3–8, 13–18, 23–28, 33–38, 43, 53–55, 63–65, 73, and 83–85, and isolated polypeptides or proteins which are encoded by a nucleic acid molecule consisting of the nucleotide sequence which hybridizes under stringent hybridization conditions to a nucleic acid molecule having the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424.

Also within the invention are polypeptides which are naturally occurring allelic variants of a polypeptide that includes the amino acid sequence of any of SEQ ID NOs: 3–8, 13–18, 23–28, 33–38, 43, 53–55, 63–65, 73, and 83–85, wherein the polypeptide is encoded by a nucleic acid molecule which hybridizes under stringent conditions to a nucleic acid molecule having the nucleotide sequence of any of SEQ ID NOs: 1, 2, 11, 12, 21, 22, 31, 32, 41, 42, 51, 52, 61, 62, 71, 72, 81, 82,and the nucleotide sequence of any of the clones deposited as ATCC® Accession numbers 207185, 207221, PTA-147, PTA-425, and PTA-424, or a complement thereof.

The invention also features nucleic acid molecules that hybridize under stringent conditions to a nucleic acid molecule having the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or a complement thereof. In other embodiments, the nucleic acid molecules are at least 15 (25, 40, 60, 80, 100, 150, 200, 250, 300, 350, 400, 450, 500, 600, 700, 800, 900, 1000, 1200, 1400, 1600, 1800, 2000, 2200, 2400, 2600, 2800, 3000, or 3500 or more) nucleotides in length and hybridize under stringent conditions to a nucleic acid molecule having the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or a complement thereof. In some embodiments, the isolated nucleic acid molecules encode a cytoplasmic, transmembrane, extracellular, or other domain of a polypeptide of the invention. In other embodiments, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides isolated host cells, e.g., mammalian or non-mammalian cells, containing such a vector or a nucleic acid of the invention. The invention also provides methods for producing a polypeptide of the invention by culturing, in a suitable medium, a host cell of the invention containing a recombinant expression vector encoding a polypeptide of the invention such that the polypeptide of the invention is produced.

Another aspect of this invention features isolated or recombinant proteins and polypeptides of the invention.

Preferred proteins and polypeptides possess at least one biological activity possessed by the corresponding naturally-occurring human polypeptide. An activity, a biological activity, and a functional activity of a polypeptide of the invention refers to an activity exerted by a protein or polypeptide of the invention on a responsive cell as determined in vivo, or in vitro, according to standard techniques. Such activities can be a direct activity, such as an association with or an enzymatic activity exerted on a second protein or an indirect activity, such as a cellular processes mediated by interaction of the protein with a second protein.

TANGO 273 protein mediates one or more physiological responses of cells to bacterial infection, e.g., by mediating one or more of detection of bacteria in a tissue in which it is expressed, movement of cells with relation to sites of bacterial infection, production of biological molecules which inhibit bacterial infection, and production of biological molecules which alleviate cellular or other physiological damage wrought by bacterial infection. TANGO 273, a transmembrane protein, is also involved in transmembrane signal transduction, and therefore mediates transmission of signals between the extracellular and intracellular environments of cells. TANGO 273 mediates regulation of cell growth and proliferation, endocytosis, activation of respiratory burst, and other physiological processes triggered by transmission of a signal via a protein with which TANGO 273 interacts. The compositions and methods of the invention can therefore be used to prevent, diagnose, and treat disorders involving one or more physiological activities mediated by TANGO 273 protein.

As an additional example, TANGO 325 polypeptides, nucleic acids, and modulators thereof modulate growth, proliferation, survival, differentiation, and activity of human tissues such as vascular endothelium, including aortic endothelium, other heart tissues, placenta, liver, kidney, and pancreas tissues. Thus, TANGO 325 polypeptides, nucleic acids, and modulators thereof can therefore be used to prevent, diagnose, and treat disorders involving one or more physiological activities mediated by TANGO 325 protein in tissues in which it is expressed. Such activities include, for example, modulation of cardiac contractility and vasomotor tone, modulation of leukocyte extravasation, sensing physiological signals by the endocrine system, modulating growth, development, maintenance, and regeneration of neurons, and the like.

TANGO 364, compounds which modulate its activity, expression, or both, and compounds (e.g., antibodies) which bind with TANGO 364 (collectively "TANGO 364-related molecules") exhibit the ability to affect one or more of growth, proliferation, survival, differentiation, activity, morphology, and movement/migration of, for example, human fetal and adult skin cells and tissue. Furthermore, TANGO 364 is involved in modulating cell-to-cell adhesion, tissue and extracellular matrix invasivity of cells, infectivity of cells by pathogens (e.g., bacteria and viruses), endocrine signaling processes, tissue developmental and organizational processes, and the like. Thus, TANGO 364-related molecules can be used to prognosticate, prevent, diagnose, or treat one or more disorders associated with these physiological processes.

TANGO 405, compounds which modulate its activity, expression, or both, and compounds (e.g., antibodies) which bind with TANGO 405 (collectively "TANGO 405-related molecules") modulate one or more of growth, proliferation, survival, differentiation, activity, morphology, and movement/migration of human lymphocytes and bone marrow cells and tissues. As described herein, TANGO 405 is involved in activation of leukocytes, including modulating one or more of growth, proliferation, survival, differentiation, activity, morphology, movement/migration, and other cellular processes by which leukocytes are characterized. TANGO 405 is involved in disorders associated with aberrant activation of leukocytes, including both auto-immune disorders and disorders related to inappropriate activity or activation of leukocytes and disorders related to uncontrolled proliferation of leukocytes.

M019 protein, compounds which modulate its activity, expression, or both, and compounds (e.g., antibodies) which bind with M019 (collectively "M019-related molecules") exhibit the ability to affect growth, proliferation, survival, differentiation, and activity of adipose tissue cells.

In one embodiment, a polypeptide of the invention has an amino acid sequence sufficiently identical to a polypeptide of the invention or to an identified domain thereof. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common domain and/or common functional activity. For example, amino acid or nucleotide sequences which contain a common domain having about 65% identity, preferably 75% identity, more preferably 85%, 95%, or 98% identity are defined herein as sufficiently identical.

In one embodiment, the isolated polypeptide of the invention lacks both a transmembrane and a cytoplasmic domain. In another embodiment, the polypeptide lacks both a transmembrane domain and a cytoplasmic domain and is soluble under physiological conditions.

The polypeptides of the present invention, or biologically active portions thereof, can be operably linked with a heterologous amino acid sequence to form fusion proteins. The invention further features antibody substances that specifically bind a polypeptide of the invention, such as monoclonal or polyclonal antibodies, antibody fragments, and single-chain antibodies. In addition, the polypeptides of the invention or biologically active portions thereof can be incorporated into pharmaceutical compositions, which optionally include pharmaceutically acceptable carriers. These antibody substances can be made, for example, by providing the polypeptide of the invention to an immunocompetent vertebrate and thereafter harvesting blood or serum from the vertebrate.

In another aspect, the present invention provides methods for detecting the presence of the activity or expression of a polypeptide of the invention in a biological sample by contacting the biological sample with an agent capable of detecting an indicator of activity such that the presence of activity is detected in the biological sample.

In another aspect, the invention provides methods for modulating activity of a polypeptide of the invention comprising contacting a cell with an agent that modulates (inhibits or enhances) the activity or expression of a polypeptide of the invention such that activity or expression in the cell is modulated. In one embodiment, the agent is an antibody that specifically binds with a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense with respect to the coding strand of an mRNA encoding a polypeptide of the invention.

The present invention also provides methods of treating a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule. In yet another embodiment, the modulator is an antibody.

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of a polypeptide of the invention wherein a wild-type form of the gene encodes a polypeptide having the activity of the polypeptide of the invention.

In another aspect, the invention provides a method for identifying a compound that binds with or modulates the activity of a polypeptide of the invention. In general, such methods entail measuring a biological activity of the polypeptide in the presence and absence of a test compound and identifying those compounds which bind with or alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIG. 1 comprises FIGS. 1A through 1C. An alignment of the amino acid sequences of human ("Hum."; SEQ ID NO: 3) and murine ("Mur."; SEQ ID NO: 13) TANGO 273 protein is shown in FIG. 1A, wherein identical amino acid residues are indicated by ":" and similar amino acid residues are indicated by ".".

FIG. 2 comprises FIGS. 2A through 2H-18. In FIGS. 2H-1 to 2H-18, an alignment of the nucleotide sequences of the cDNA encoding human TANGO 325 protein ("325"; SEQ ID NO: 23) and the nucleotide sequence of the cDNA encoding Slit-1 protein ("Slit"; SEQ ID NO: 30) is shown. This alignment was made using the ALIGN software {Myers and Miller (1989) CABIOS, ver. 2.0}; pam120.mat scoring matrix; gap opening penalty=12, gap extension penalty=4).

FIG. 3 comprises FIGS. 3A through 3C. FIGS. 3B and 3C are an alignment of the amino acid sequence of SEQ ID NOs: 33 and 43.

FIG. 4 comprises FIGS. 4A through 4H. FIG. 4G is an alignment of the amino acid sequences of murine TANGO 405 protein ("mT405"; SEQ ID NO: 63) and murine dectin-2 ("Dectin"; SEQ ID NO: 60). FIG. 4H is an alignment of the amino acid sequences of human TANGO 405 protein ("hT405"; SEQ ID NO: 53) and murine dectin-2 ("Dectin"; SEQ ID NO: 60).

DETAILED DESCRIPTION OF THE INVENTION

Figure 1B:
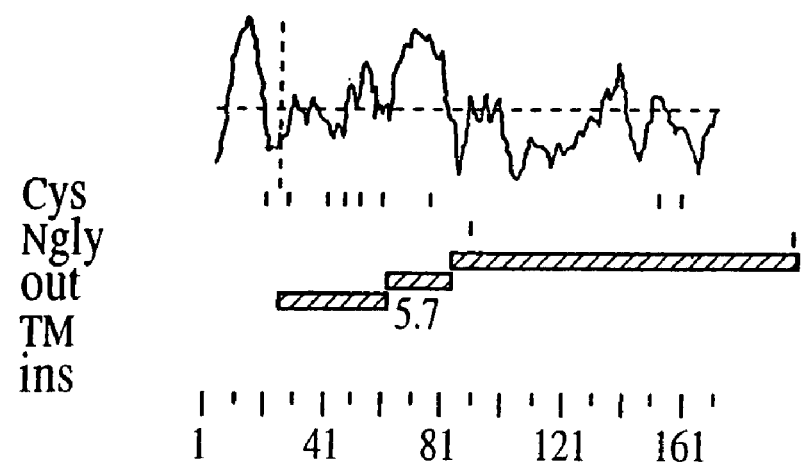
FIG. 1B is a hydrophobicity plot of human TANGO 273 protein.

The present invention is based, at least in part, on the discovery of a variety of cDNA molecules which encode proteins which are herein designated TANGO 273, TANGO 325, TANGO 364, TANGO 405, and M019. These proteins exhibit a variety of physiological activities, and are included in a single application for the sake of convenience. It is understood that the allowability or non-allowability of claims directed to one of these proteins has no bearing on the allowability of claims directed to the others. The characteristics of each of these proteins and the cDNAs encoding them are described separately in the ensuing sections. In addition to the full length mature and immature proteins described in the following sections, the invention includes fragments, derivatives, and variants of these proteins, as described herein. These proteins, fragments, derivatives, and variants are collectively referred to herein as polypeptides of the invention or proteins of the invention.

TANGO 273

A cDNA clone (designated jthoc028g06) encoding at least a portion of human TANGO 273 protein was isolated from a lipopolysaccharide- (LPS-)stimulated human osteoblast cDNA library. The corresponding murine cDNA clone (designated jtmoa001c04) was isolated from an LPS-stimulated murine osteoblast cDNA library. The human and murine TANGO 273 proteins are predicted by structural analysis to be transmembrane proteins.

The full length of the cDNA encoding human TANGO 273 protein (SEQ ID NO: 1) is 2964 nucleotide residues. The ORF of this cDNA, nucleotide residues 135 to 650 of SEQ ID NO: 1 (i.e., SEQ ID NO: 2), encodes a 172-amino acid transmembrane protein (SEQ ID NO: 3).

The invention thus includes purified human TANGO 273 protein, both in the form of the immature 172 amino acid residue protein (SEQ ID NO: 3) and in the form of the mature 150 amino acid residue protein (SEQ ID NO: 5). The invention also includes purified murine TANGO 273 protein, both in the form of the immature 172 amino acid residue protein (SEQ ID NO: 13) and in the form of the mature 150 amino acid residue protein (SEQ ID NO: 15). Mature human or murine TANGO 273 proteins can be synthesized without the signal sequence polypeptide at the amino terminus thereof, or they can be synthesized by generating immature TANGO 273 protein and cleaving the signal sequence therefrom.

The invention also includes nucleic acid molecules which encode a polypeptide of the invention. Such nucleic acids include, for example, a DNA molecule having the nucleotide sequence listed in SEQ ID NO: 1 or some portion thereof or SEQ ID NO: 12 or some portion thereof, such as the portion which encodes mature TANGO 273 protein, immature TANGO 273 protein, or a domain of TANGO 273 protein. These nucleic acids are collectively referred to as nucleic acids of the invention.

TANGO 273 proteins and nucleic acid molecules encoding them comprise a family of molecules having certain conserved structural and functional features. This family includes, by way of example, the human and murine TANGO 273 proteins.

A common domain of TANGO 273 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 273 protein contains a signal sequence corresponding to amino acid residues 1 to 22 of SEQ ID NO: 3 (SEQ ID NO: 4) or to amino acid residues 1 to 22 of SEQ ID NO: 13. The signal sequence is cleaved during processing of the mature protein.

TANGO 273 proteins can also include an extracellular domain. The human TANGO 273 protein extracellular domain is located from about amino acid residue 23 to about amino acid residue 60 of SEQ ID NO: 3, and the murine TANGO 273 protein extracellular domain is located from about amino acid residue 23 to about amino acid residue 60 of SEQ ID NO: 13.

The present invention also includes TANGO 273 proteins having a transmembrane domain. As used herein, a "transmembrane domain" refers to an amino acid sequence having at least about 15 to 50 amino acid residues in length and which contains at least about 65–70% hydrophobic amino acid residues such as alanine, leucine, phenylalanine, protein, tyrosine, tryptophan, or valine. In a preferred embodiment, a transmembrane domain has at least about 60–80%, more preferably 65–75%, and more preferably at least about 70% hydrophobic residues. Thus, in one embodiment, a human TANGO 273 protein of the invention contains a transmembrane domain corresponding to about amino acid residues 61 to 81 of SEQ ID NO: 3 (SEQ ID NO: 7). In another embodiment, a murine TANGO 273 protein of the invention contains a transmembrane domain corresponding to about amino acid residues 61 to 81 of SEQ ID NO: 13.

In addition, TANGO 273 proteins include a cytoplasmic domain. The human TANGO 273 cytoplasmic domain is located from about amino acid residue 82 to amino acid residue 172 of SEQ ID NO: 3 (SEQ ID NO: 8), and the murine TANGO 273 cytoplasmic domain is located from about amino acid residue 82 to amino acid residue 172 of SEQ ID NO: 13.

TANGO 273 proteins typically comprise a variety of potential post-translational modification sites (often within an extracellular domain), such as those described herein in Tables I and II, as predicted by computerized sequence analysis of human and murine TANGO 273 proteins using amino acid sequence comparison software (comparing the amino acid sequence of TANGO 273 with the information in the PROSITE database {rel. 12.2; February, 1995} and the Hidden Markov Models database {Rel. PFAM 3.3}). As used herein, the term "post-translational modification site" refers to a protein domain that includes about 3 to 10 amino acid residues, more preferably about 3 to 6 amino acid residues wherein the domain has an amino acid sequence which comprises a consensus sequence which is recognized and modified by a protein-modifying enzyme. Examples of protein-modifying enzymes include amino acid glycosylases, cAMP- and cGMP-dependent protein kinases, protein kinase C, casein kinase II, and myristoylases. In certain embodiments, a protein of the invention has at least 1, 2, 3, 4, 5, or all 6 of the post-translational modification sites listed in Table I. In other embodiments, the protein of the invention has at least 1, 2, 3, 4, 5, 6, or all 7 of the post-translational modification sites listed in Table II.

TABLE I

| Type of Potential Modification Site or Domain | Amino Acid Residues of SEQ ID NO: 3 | Amino Acid Sequence |
|---|---|---|
| N-glycosylation site | 97 to 100 | NVSY |
| Casein kinase II phosphorylation site | 41 to 44 | SYED |
| N-myristoylation site | 31 to 36 | GLYPTY |
|  | 47 to 52 | GSRCCV |
|  | 70 to 75 | GVLFCC |
|  | 131 to 136 | GNSMAM |
| Src Homology 3 (SH3) domain binding site | 86 to 90 | YPPPL |
|  | 103 to 107 | QPPNP |
|  | 113 to 117 | QPGPP |
|  | 121 to 125 | DPGGP |
|  | 140 to 145 | VPPNSP |
|  | 151 to 155 | CPPPP |
|  | 160 to 164 | TPPPP |

TABLE II

| Type of Potential Modification Site or Domain | Amino Acid Residues of SEQ ID NO: 13 | Amino Acid Sequence |
|---|---|---|
| N-glycosylation site | 97 to 100 | NVSY |
| Casein kinase II phosphorylation site | 41 to 44 | SYED |
| N-myristoylation site | 31 to 36 | GLYPTY |
|  | 47 to 52 | GSRCCV |
|  | 70 to 75 | GVLFCC |
|  | 131 to 136 | GNTMAM |
| Src Homology 3 (SH3) domain binding site | 86 to 90 | YPPPL |
|  | 103 to 107 | QPPNP |
|  | 115 to 119 | GPPYY |
|  | 121 to 125 | DPGGP |
|  | 141 to 145 | QPNSP |
|  | 151 to 155 | YPPPP |
|  | 160 to 164 | TPPPP |
| Amidation site | 1 to 4 | MGRR |

The amino acid sequence of TANGO 273 protein includes about seven potential proline-rich Src homology 3 (SH3) domain binding sites nearer the cytoplasmic portion of the protein. SH3 domains mediate specific assembly of protein complexes, presumably by interacting with proline-rich protein domains (Morton and Campbell (1994) Curr. Biol. 4:615–617). SH3 domains also mediate interactions between proteins involved in transmembrane signal transduction. Coupling of proteins mediated by SH3 domains has been implicated in a variety of physiological systems, including those involving regulation of cell growth and proliferation, endocytosis, and activation of respiratory burst.

SH3 domains have been described in the art (e.g., Mayer et al. (1988) Nature 332:272–275; Musacchio et al. (1992)

FEBS Lett. 307:55–61; Pawson and Schlessinger (1993) Curr. Biol. 3:434–442; Mayer and Baltimore (1993) Trends Cell Biol. 3:8–13; Pawson (1993) Nature 373:573–580), and occur in a variety of cytoplasmic proteins, including several (e.g., protein tyrosine kinases) involved in transmembrane signal transduction. Among the proteins in which one or more SH3 domains occur are protein tyrosine kinases such as those of the Src, Abl, Bkt, Csk and ZAP70 families, mammalian phosphatidylinositol-specific phospholipases C-gamma-1 and -2, mammalian phosphatidylinositol 3-kinase regulatory p85 subunit, mammalian Ras GTPase-activating protein (GAP), proteins which mediate binding of guanine nucleotide exchange factors and growth factor receptors (e.g., vertebrate GRB2, Caenorhabditis elegans sem-5, and Drosophila DRK proteins), mammalian Vav oncoprotein, guanidine nucleotide releasing factors of the CDC 25 family (e.g., yeast CDC25, yeast SCD25, and fission yeast ste6 proteins), MAGUK proteins (e.g., mammalian tight junction protein ZO-1, vertebrate erythrocyte membrane protein p55, C. elegans protein lin-2, rat protein CASK, and mammalian synaptic proteins SAP90/PSD-95, CHAPSYN-110/PSD-93, SAP97/DLG1, and SAP102), proteins which interact with vertebrate receptor protein tyrosine kinases (e.g., mammalian cytoplasmic protein Nck and oncoprotein Crk), chicken Src substrate p80/85 protein (cortactin), human hemopoietic lineage cell specific protein Hs1, mammalian dihydrouridine-sensitive L-type calcium channel beta subunit, human myasthenic syndrome antigen B (MSYB), mammalian neutrophil cytosolic activators of NADPH oxidase (e.g., p47 {NCF-1}, p67 {NCF-2}, and C. elegans protein B0303.7) myosin heavy chains (MYO3) from amoebae, from slime molds, and from yeast, vertebrate and Drosophila spectrin and fodrin alpha chain proteins, human amphiphysin, yeast actin-binding proteins ABP1 and SLA3, yeast protein BEM1, fission yeast protein scd2 (ral3), yeast BEM1-binding proteins BOI2 (BEB1) and BOB1 (BOI1), yeast fusion protein FUS1, yeast protein RSV167, yeast protein SSU81, yeast hypothetical proteins YAR014c, YFR024c, YHL002w, YHR016c, YJL020C, and YHR114w, hypothetical fission yeast protein SpAC12C2.05c, and C. elegans hypothetical protein F42H10.3. Of these proteins, multiple SH3 domains occur in vertebrate GRB2 protein, C. elegans sem-5 protein, Drosophila DRK protein, oncoprotein Crk, mammalian neutrophil cytosolic activators of NADPH oxidase p47 and p67, yeast protein BEM1, fission yeast protein scd2, yeast hypothetical protein YHR114w, mammalian cytoplasmic protein Nck, C. elegans neutrophil cytosolic activator of NADPH oxidase B0303.7, and yeast actin-binding protein SLA1. Of these proteins, three or more SH3 domains occur in mammalian cytoplasmic protein Nck, C. elegans neutrophil cytosolic activator of NADPH oxidase B0303.7, and yeast actin-binding protein SLA1. The presence of SH3 domain binding sites in TANGO 273 indicates that TANGO 273 interacts with one or more of these and other SH3 domain-containing proteins and is thus involved in physiological processes in which one or more of these or other SH3 domain-containing proteins are involved.

The signal peptide prediction program SIGNALP (Nielsen et al. (1997) Protein Engineering 10:1–6) predicted that human TANGO 273 protein includes a 22 amino acid signal peptide (amino acid residues 1 to 22 of SEQ ID NO: 3; SEQ ID NO: 4) preceding the mature TANGO 273 protein (amino acid residues 23 to 172 of SEQ ID NO: 3; SEQ ID NO: 5). Human TANGO 273 protein includes an extracellular domain (amino acid residues 23 to 60 of SEQ ID NO: 3; SEQ ID NO: 6); a transmembrane domain (amino acid residues 61 to 81 of SEQ ID NO: 3 ; SEQ ID NO: 7); and a cytoplasmic domain (amino acid residues 82 to 172 of SEQ ID NO: 3; SEQ ID NO: 8).

FIG. 1B depicts a hydrophobicity plot of human TANGO 273 protein. Relatively hydrophobic regions are above the dashed horizontal line, and relatively hydrophilic regions are below the dashed horizontal line. The hydrophobic region which corresponds to amino acid residues 1 to 22 of SEQ ID NO: 3 is the signal sequence of human TANGO 273 (SEQ ID NO: 4). The hydrophobic region which corresponds to amino acid residues 61 to 81 of SEQ ID NO: 3 is the transmembrane domain of human TANGO 273 (SEQ ID NO: 7). As described elsewhere herein, relatively hydrophilic regions are generally located at or near the surface of a protein, and are more frequently effective immunogenic epitopes than are relatively hydrophobic regions. For example, the region of human TANGO 273 protein from about amino acid residue 100 to about amino acid residue 120 appears to be located at or near the surface of the protein, while the region from about amino acid residue 130 to about amino acid residue 140 appears not to be located at or near the surface.

Chromosomal mapping was performed by computerized comparison of TANGO 273 cDNA sequences against a chromosomal mapping database in order to identify the approximate location of the gene encoding human TANGO 273 protein. This analysis indicated that the gene is located on chromosome 7 between markers D7S2467 and D7S2552.

The predicted molecular weight of human TANGO 273 protein without modification and prior to cleavage of the signal sequence is about 19.2 kilodaltons. The predicted molecular weight of the mature human TANGO 273 protein without modification and after cleavage of the signal sequence is about 16.8 kilodaltons.

Northern analysis experiments indicated that mRNA corresponding to the cDNA encoding TANGO 273 is expressed in the tissues listed in Table III, wherein "++" indicates moderate expression and "+" indicates lower expression.

TABLE III

| Animal | Tissue | Relative Level of Expression |
|---|---|---|
| Human | heart | ++ |
| | brain | ++ |
| | skeletal muscle | ++ |
| | pancreas | ++ |
| | placenta | + |
| | lung | + |
| | liver | + |
| | kidney | + |

The full length of the cDNA encoding murine TANGO 273 protein (SEQ ID NO: 11) is 2915 nucleotide residues. The ORF of this cDNA, nucleotide residues 137 to 650 of SEQ ID NO: 11 (i.e., SEQ ID NO: 12), encodes a 172-amino acid transmembrane protein (SEQ ID NO: 13).

The signal peptide prediction program SIGNALP (Nielsen et al. (1997) Protein Engineering 10:1–6) predicted that murine TANGO 273 protein includes a 22 amino acid signal peptide (amino acid residues 1 to 22 of SEQ ID NO: 13) preceding the mature TANGO 273 protein (amino acid residues 23 to 172 of SEQ ID NO: 13; SEQ ID NO: 15). Murine TANGO 273 protein includes an extracellular domain (amino acid residues 23 to 60 of SEQ ID NO: 13); a transmembrane domain (amino acid residues 61 to 81 of SEQ ID NO: 13); and a cytoplasmic domain (amino acid residues 82 to 172 of SEQ ID NO: 13).

Figure 1C:
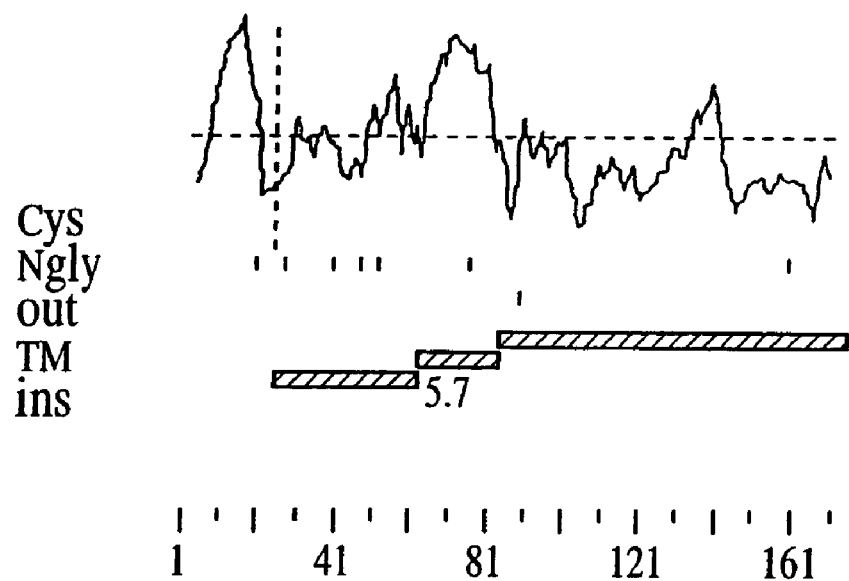
FIG. 1C is a hydrophobicity plot of murine TANGO 273 protein.

FIG. 1C depicts a hydrophobicity plot of murine TANGO 273 protein. Relatively hydrophobic regions are above the dashed horizontal line, and relatively hydrophilic regions are below the dashed horizontal line. The hydrophobic region which corresponds to amino acid residues 1 to 22 of SEQ ID NO: 13 is the signal sequence of murine TANGO 273. As described elsewhere herein, relatively hydrophilic regions are generally located at or near the surface of a protein, and are more frequently effective immunogenic epitopes than are relatively hydrophobic regions. For example, the region of murine TANGO 273 protein from about amino acid residue 100 to about amino acid residue 120 appears to be located at or near the surface of the protein, while the region from about amino acid residue 130 to about amino acid residue 140 appears not to be located at or near the surface.

The predicted molecular weight of murine TANGO 273 protein without modification and prior to cleavage of the signal sequence is about 19.4 kilodaltons. The predicted molecular weight of the mature murine TANGO 273 protein without modification and after cleavage of the signal sequence is about 17.1 kilodaltons.

In situ analysis of murine TANGO 273 mRNA indicated that TANGO 273 is expressed in central nervous system (CNS) tissues during embryogenesis and into adulthood. Expression of TANGO 273 is widely observed in murine CNS tissues, including brain, spinal cord, eye, and olfactory epithelium at all embryonic ages examined (i.e., at embryonic days 13.5, 14.5, 15.5, 16.5, and 18.5 and at post-natal day 1.5).

Human and murine TANGO 273 cDNA sequences exhibit significant nucleotide sequence identity with an expressed sequence tag (EST) isolated from a library of ESTs corresponding to proteins secreted from prostate tissue, as described in PCT publication number WO 99/06550, published Feb. 11, 1999.

Human and murine TANGO 273 proteins exhibit considerable sequence similarity, as indicated herein in FIG. 1A. FIG. 1A depicts an alignment of human and murine TANGO 273 protein amino acid sequences (SEQ ID NOs: 3 and 13, respectively). In this alignment (pam120.mat scoring matrix, gap penalties −12/−4), the proteins are 89.5% identical. Alignment of the ORF encoding human TANGO 273 protein and the ORF encoding murine TANGO 273 protein using the same software and parameters indicated that the nucleotide sequences are 84.1% identical.

Uses of TANGO 273 Nucleic Acids,

Polypeptides, and Modulators thereof cDNAs encoding the human and murine TANGO 273 proteins were each isolated from LPS-stimulated osteoblast cDNA libraries. These proteins are involved in bone-related metabolism, homeostasis, and development disorders. Thus, proteins and nucleic acids of the invention which are identical to, similar to, or derived from human and murine TANGO 273 proteins and nucleic acids encoding them are useful for preventing, diagnosing, and treating, among others, bone-related disorders such as osteoporosis, cancer, skeletal development disorders, bone fragility, and the like.

Expression of TANGO 273 in heart, brain, skeletal muscle, and pancreas, placenta, lung, liver, and kidney tissues is an indication that TANGO 273 proteins, nucleic acids encoding them, and agents that modulate activity or expression of either of these can be used to modulate growth, proliferation, survival, differentiation, adhesion, and activity of cells of these tissues, or to prognosticate, diagnose, and treat one or more disorders which affect these tissues.

The fact that TANGO 273 is expressed at high levels in neurological tissues is an indication that TANGO 273 proteins, nucleic acids, and modulators thereof can be used to modulate proliferation, differentiation, or function of neurological cells in these tissues (e.g., neuronal cells). Thus, TANGO 273 proteins, nucleic acids, and modulators thereof can be used to prognosticate, diagnose, and treat one or more neurological disorders. Examples of such disorders include CNS disorders, CNS-related disorders, focal brain disorders, global-diffuse cerebral disorders, and other neurological and cerebrovascular disorders.

CNS disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders (e.g., insomnia, hypersomnia, parasomnia, and sleep apnea); neuropsychiatric disorders (e.g., schizophrenia, schizoaffective disorder, attention deficit disorder, dysthymic disorder, major depressive disorder, mania, and obsessive-compulsive disorder); psychoactive substance use disorders; anxiety; panic disorder; and bipolar affective disorders (e.g., severe bipolar affective disorder and bipolar affective disorder with hypomania and major depression).

CNS-related disorders include disorders associated with developmental, cognitive, and autonomic neural and neurological processes, such as pain, appetite, long term memory, and short term memory.

Examples of focal brain disorders include aphasia, apraxia, agnosia, and amnesias (e.g., posttraumatic amnesia, transient global amnesia, and psychogenic amnesia). Global-diffuse cerebral disorders with which TANGO 273 can be associated include coma, stupor, obtundation, and disorders of the reticular formation.

Other neurological disorders with which TANGO 273 can be associated include ischemic syndromes (e.g., stroke), hypertensive encephalopathy, hemorrhagic disorders, and disorders involving aberrant function of the blood-brain barrier (e.g., CNS infections such as meningitis and encephalitis, aseptic meningitis, metastasis of non-CNS tumor cells into the CNS, various pain disorders such as migraine, blindness and other vision problems, and CNS-related adverse drug reactions such as head pain, sleepiness, and confusion). TANGO 273 proteins, nucleic acids encoding them, and agents that modulate activity or expression of either of these can be used to prognosticate, diagnose, and treat one or more of these disorders.

Developmental regulation of TANGO 273 expression in fetal neurological tissues, as described herein, is an indication that TANGO 273 proteins, nucleic acids, and modulators thereof can be used to prognosticate, diagnose, and treat one or more disorders which involve aberrant fetal neurological development. Examples of such disorders include blindness, deafness, fetal death, mental retardation, dysraphia, anencephaly, malformation of cerebral hemispheres, encephalocele, porencephaly, hydranencephaly, hydrocephalus, and spina bifida.

The fact that TANGO 273 is expressed in tissues which were exposed to LPS indicates that TANGO 273 mediates one or more physiological responses of cells to bacterial infection. Thus, TANGO 273 is involved in one or more of detection of bacteria in a tissue in which it is expressed, movement of cells with relation to sites of bacterial infection, production of biological molecules which inhibit bacterial infection, and production of biological molecules which alleviate cellular or other physiological damage wrought by bacterial infection.

Presence in TANGO 273 protein of multiple SH3 domain binding sites indicates that TANGO 273 protein interacts with one or more SH3 domain-containing proteins. Thus, TANGO 273 protein mediates binding of proteins (i.e., binding of proteins to TANGO 273 and to one another to form protein complexes) in cells in which it is expressed. TANGO 273 is also involved in transduction of signals between the exterior environment of cells (i.e., including from other cells) and the interior of cells in which it is expressed. TANGO 273 mediates regulation of cell growth and proliferation, endocytosis, activation of respiratory burst, and other physiological processes triggered by transmission of a signal via a protein with which TANGO 273 interacts.

Sequence similarity of TANGO 273 cDNA with an EST expressed in prostate tissue indicates that TANGO 273 can be expressed in prostate tissue, and can thus be involved in disorders of the prostate. Thus, TANGO 273 proteins, nucleic acids encoding them, and agents that modulate activity or expression of either of these can be used to treat prostate disorders. Examples of prostate disorders which can be treated in this manner include inflammatory prostatic diseases (e.g., acute and chronic prostatitis and granulomatous prostatitis), prostatic hyperplasia (e.g., benign prostatic hypertrophy or hyperplasia), and prostate tumors (e.g., carcinomas).

In another example, TANGO 273 polypeptides, nucleic acids, or modulators thereof, can be used to treat cardiovascular disorders. Examples of cardiac disorders which can be treated in this manner include ischemic heart diseases (e.g., angina pectoris, myocardial infarction and its aftermath, coronary artery disease, cardiac arrest, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), cardiac arrhythmia, cardiac insufficiency, endocarditis, pericardial disease, muscular dystrophy, and myocardial disease (e.g., myocarditis, congestive cardiomyopathy, restrictive cardiomyopathy, and hypertrophic cardiomyopathy). Examples of vascular disorders which can be treated in this manner include arteriosclerosis, atherosclerosis, hypertension, aberrant or non-desired angiogenesis, stenosis and restenosis, and smooth muscle proliferation in response to traumatic injury.

In another example, TANGO 273 polypeptides, nucleic acids, or modulators thereof, can be used to treat disorders of the brain. Examples of brain disorders in which TANGO 273 can have role include both CNS disorders, CNS-related disorders, focal brain disorders, global-diffuse cerebral disorders, and other neurological and cerebrovascular disorders. CNS disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders (e.g., insomnia, hypersonmia, parasomnia, and sleep apnea), neuropsychiatric disorders (e.g., schizophrenia, schizoaffective disorder, attention deficit disorder, dysthymic disorder, major depressive disorder, mania, and obsessive-compulsive disorder), psychoactive substance use disorders, anxiety, panic disorder, and bipolar affective disorder (e.g., severe bipolar affective disorder and bipolar affective disorder with hypomania and major depression). CNS-related disorders include disorders associated with developmental, cognitive, and autonomic neural and neurological processes, such as pain, appetite, long term memory, and short term memory. Examples of focal brain disorders include aphasia, apraxia, agnosia, and amnesias (e.g., posttraumatic amnesia, transient global amnesia, and psychogenic amnesia). Global-diffuse cerebral disorders with which TANGO 273 is associated include coma, stupor, obtundation, and disorders of the reticular formation. Cerebrovascular disorders include ischemic syndromes (e.g., stroke), hypertensive encephalopathy, hemorrhagic disorders, and disorders involving aberrant function of the blood-brain barrier (e.g., CNS infections such as meningitis and encephalitis, aseptic meningitis, metastasis of non-CNS tumor cells into the CNS, various pain disorders such as migraine, and CNS-related adverse drug reactions such as head pain, sleepiness, and confusion).

In another example, TANGO 273 polypeptides, nucleic acids, or modulators thereof, can be used to treat disorders of skeletal muscle, such as muscular dystrophy (e.g., Duchenne muscular dystrophy, Becker muscular dystrophy, Emery-Dreifuss muscular dystrophy, limb-girdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies such as dermatomyositis and polymyositis, myotonia congenita, paramyotonia congenita, central core disease, nemaline myopathy, myotubular myopathy, and periodic paralysis), and metabolic diseases of muscle (e.g., phosphorylase deficiency, acid maltase deficiency, phosphofructokinase deficiency, debrancher enzyme deficiency, mitochondrial myopathy, carnitine deficiency, carnitine palmityl transferase deficiency, phosphoglycerate kinase deficiency, phosphoglycerate mutase deficiency, lactate dehydrogenase deficiency, and myoadenylate deaminase deficiency).

In another example, TANGO 273 polypeptides, nucleic acids, or modulators thereof, can be used to treat pancreatic disorders, such as pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), or islet cell tumors (e.g., insulinomas, adenomas, Zollinger-Ellison syndrome, glucagonomas, and somatostatinoma).

In another example, TANGO 273 polypeptides, nucleic acids, or modulators thereof, can be used to treat placental disorders, such as toxemia of pregnancy (e.g., preeclampsia and eclampsia), placentitis, or spontaneous abortion.

In another example, TANGO 273 polypeptides, nucleic acids, or modulators thereof, can be used to treat pulmonary disorders, such as atelectasis, cystic fibrosis, rheumatoid lung disease, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchioalveolar carcinoma, bronchial carcinoid, hamartoma, and mesenchymal tumors).

In another example, TANGO 273 polypeptides, nucleic acids, or modulators thereof, can be used to treat hepatic (liver) disorders, such as jaundice, hepatic failure, hereditary hyperbilirubinemias (e.g., Gilbert's syndrome, Crigler-Naijar syndromes, and Dubin-Johnson and Rotor's syndromes), hepatic circulatory disorders (e.g., hepatic vein thrombosis and portal vein obstruction and thrombosis) hepatitis (e.g., chronic active hepatitis, acute viral hepatitis, and toxic and drug-induced hepatitis) cirrhosis (e.g., alcoholic cirrhosis, biliary cirrhosis, and hemochromatosis), or malignant tumors (e.g., primary carcinoma, hepatoblastoma, and angiosarcoma).

In another example, TANGO 273 polypeptides, nucleic acids, or modulators thereof, can be used to treat renal (kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

TANGO 325

A cDNA clone (designated jthdc071a12) encoding at least a portion of human TANGO 325 protein was isolated from a human aortic endothelial cell cDNA library. The human TANGO 325 protein is predicted by structural analysis to be a transmembrane protein.

The full length of the cDNA encoding human TANGO 325 protein (SEQ ID NO: 21) is 2169 nucleotide residues. The ORF of this cDNA, nucleotide residues 135 to 2000 of SEQ ID NO: 21 (i.e., SEQ ID NO: 22), encodes a 622-amino acid transmembrane protein (SEQ ID NO: 23).

The invention thus includes purified human TANGO 325 protein, both in the form of the immature 622 amino acid residue protein (SEQ ID NO: 23) and in the form of the mature, approximately 591 amino acid residue protein (SEQ ID NO: 25). Mature human TANGO 325 protein can be synthesized without the signal sequence polypeptide at the amino terminus thereof, or it can be synthesized by generating immature TANGO 325 protein and cleaving the signal sequence therefrom.

The invention also includes nucleic acid molecules which encode a TANGO 325 polypeptide of the invention. Such nucleic acids include, for example, a DNA molecule having the nucleotide sequence listed in SEQ ID NO: 21 or some portion thereof, such as the portion which encodes mature TANGO 325 protein, immature TANGO 325 protein, or a domain of TANGO 325 protein. These nucleic acids are collectively referred to as TANGO 325 nucleic acids of the invention.

TANGO 325 proteins and nucleic acid molecules encoding them comprise a family of molecules having certain conserved structural and functional features.

A common domain present in TANGO 325 proteins is a signal sequence. In one embodiment, a TANGO 325 protein contains a signal sequence corresponding to about amino acid residues 1 to 31 of SEQ ID NO: 23 (SEQ ID NO: 24). The signal sequence is cleaved during processing of the mature protein.

TANGO 325 proteins can include an extracellular domain. The human TANGO 325 protein extracellular domain is located from about amino acid residue 32 to about amino acid residue 529 of SEQ ID NO: 23 (SEQ ID NO: 26).

In addition, TANGO 325 include a transmembrane domain. In one embodiment, a TANGO 325 protein of the invention contains a transmembrane domain corresponding to about amino acid residues 530 to 547 of SEQ ID NO: 23 (SEQ ID NO: 27).

The present invention includes TANGO 325 proteins having a cytoplasmic domain, particularly including proteins having a carboxyl-terminal cytoplasmic domain. The human TANGO 325 cytoplasmic domain is located from about amino acid residue 548 to amino acid residue 622 of SEQ ID NO: 23 (SEQ ID NO: 28).

TANGO 325 proteins typically comprise a variety of potential post-translational modification sites (often within an extracellular domain), such as those described herein in Table IV, as predicted by computerized sequence analysis of TANGO 325 proteins using amino acid sequence comparison software (comparing the amino acid sequence of TANGO 325 with the information in the PROSITE database {rel. 12.2; February, 1995} and the Hidden Markov Models database {Rel. PFAM 3.3}). In certain embodiments, a protein of the invention has at least 1, 2, 4, 6, 10, 15, or 20 or more of the post-translational modification sites listed in Table IV.

TABLE IV

| Type of Potential Modification Site or Domain | Amino Acid Residues of SEQ ID NO: 23 | Amino Acid Sequence |
| --- | --- | --- |
| N-glycosylation site | 71 to 74 | NISY |
| | 76 to 79 | NESE |
| | 215 to 218 | NLTK |
| | 266 to 269 | NVTR |
| | 317 to 320 | NDTF |
| | 331 to 334 | NLSF |
| | 336 to 339 | NLTA |
| | 400 to 403 | NITN |
| | 410 to 413 | NVSR |
| | 451 to 454 | NITF |
| | 579 to 582 | NVTA |
| cAMP- or cGMP-dependent protein kinase phosphorylation site | 231 to 234 | RRLS |
| Protein kinase C phosphorylation site | 40 to 42 | TGR |
| | 229 to 231 | SLR |
| | 326 to 328 | SLK |
| | 390 to 392 | SMR |
| | 510 to 512 | SGK |
| | 575 to 577 | SAR |
| Casein kinase II phosphorylation site | 284 to 287 | SHND |
| | 442 to 445 | SPLE |
| | 447 to 450 | TETE |
| | 453 to 456 | TFWE |
| N-myristoylation site | 3 to 8 | GLQFSL |
| | 69 to 74 | GNNISY |

TABLE IV-continued

| Type of Potential Modification Site or Domain | Amino Acid Residues of SEQ ID NO: 23 | Amino Acid Sequence |
|---|---|---|
| | 126 to 131 | GIFKGL |
| | 174 to 179 | GTFVGM |
| ATP/GTP-binding site motif A (P-loop) | 506 to 513 | AASMSGKT |
| Leucine rich repeat amino terminal domain (LLRNT) | 32 to 60 | See FIG. 2 |
| Leucine rich repeat (LRR) domain | 61 to 84 | See FIG. 2 |
| | 85 to 108 | See FIG. 2 |
| | 109 to 132 | See FIG. 2 |
| | 133 to 156 | See FIG. 2 |
| | 157 to 180 | See FIG. 2 |
| | 181 to 204 | See FIG. 2 |
| | 205 to 228 | See FIG. 2 |
| | 229 to 252 | See FIG. 2 |
| | 253 to 276 | See FIG. 2 |
| | 277 to 300 | See FIG. 2 |
| | 301 to 324 | See FIG. 2 |
| | 326 to 349 | See FIG. 2 |
| Leucine rich repeat carboxyl terminal domain (LRRCT) | 359 to 405 | See FIG. 2 |

Among the domains that occur in TANGO 325 protein are leucine rich repeat (LRR) domains, including amino terminal and carboxyl terminal LRR domains, and a P-loop domain. In one embodiment, the protein of the invention has at least one domain that is at least 55%, preferably at least about 65%, more preferably at least about 75%, yet more preferably at least about 85%, and most preferably at least about 95% identical to one of these domains. In another embodiment, the protein has at least one amino terminal LRR domain, at least one carboxyl terminal LRR domain, and a plurality of LRR domains interposed therebetween. In yet another embodiment, the protein has at least one P-loop domain, and a plurality (e.g., 2, 3, 4, or more) of the LRR domains described herein in Table IV.

One or more LRR domains is present in a variety of proteins involved in protein-protein interactions. Such proteins include, for example, proteins involved in signal transduction, cell-to-cell adhesion, cell-to-extracellular matrix adhesion, cell development, DNA repair, RNA processing, and cellular molecular recognition processes. Specialized LRR domains, designated LRR amino terminal (LRRNT) domains and LRR carboxyl terminal (LRRCT) domains often occur near the amino and carboxyl, respectively, ends of a series of LRR domains. TANGO 325 protein has fourteen clustered LRR domains, including (from the amino terminus toward the carboxyl terminus of TANGO 325) an LRRNT domain, twelve LRR domains, and an LRRCT domain. TANGO 325 is thus involved in one or more physiological processes in which these other LRR domain-containing proteins are involved, namely binding of cells with extracellular proteins such as soluble extracellular proteins and cell surface proteins of other cells.

The fact that TANGO 325 has an ATP/GTP-binding domain (i.e., a P-loop domain) within the extracellular domain of the protein indicates that this protein is involved in transmembrane signaling events. Considered in combination with the protein-binding LRR domains present in the extracellular domain of TANGO 325 protein, the presence of the ATP/GTP-binding domain indicates that TANGO 325 protein is capable of sensing extracellular proteins, including ATP-binding proteins and GTP-binding proteins, and extracellular nucleotides (e.g., ATP, ADP, and AMP). Thus, TANGO 325 protein is involved in translating information (e.g., environmental conditions or signaling molecules provided to the environment by other cells) from the extracellular environment of the cell in which it is expressed to one or more intracellular biochemical systems.

TANGO 325 exhibits amino acid sequence and nucleic acid sequence homology with human Slit-1 protein. An alignment of the amino acid sequences of TANGO 325 and human Slit-1 protein is shown in FIGS. 2B to 2G. In this alignment (made using the ALIGN software {Myers and Miller (1989) CABIOS, ver. 2.0}; pam120.mat scoring matrix; gap opening penalty=12, gap extension penalty=4), the proteins are 35.4% identical (i.e., 35.4% of the residues of TANGO 325 correspond to identical residues in Slit-1). An alignment of the nucleotide sequences of the ORFs encoding TANGO 325 and human Slit-1 protein is shown in FIGS. 2H-1 through 2H-18. The two ORFs are 65.7% identical, as assessed using the same software and parameters.

The signal peptide prediction program SIGNALP (Nielsen et al. (1997) Protein Engineering 10:1–6) predicted that human TANGO 325 protein includes an approximately 31 (i.e., 29, 30, 31, 32, or 33) amino acid residue signal peptide (amino acid residues 1 to 31 of SEQ ID NO: 23; SEQ ID NO: 24) preceding the mature TANGO 325 protein (i.e., approximately amino acid residues 42 to 622 of SEQ ID NO: 23; SEQ ID NO: 25). In one embodiment, human TANGO 325 protein includes an extracellular domain (amino acid residues 32 to 529 of SEQ ID NO: 23; SEQ ID NO: 26); a transmembrane domain (amino acid residues 530 to 547 of SEQ ID NO: 23; SEQ ID NO: 27); and a cytoplasmic domain (amino acid residues 548 to 622 of SEQ ID NO: 23; SEQ ID NO: 28). In an alternative embodiment, human TANGO 325 protein includes a cytoplasmic domain (amino acid residues 32 to 529 of SEQ ID NO: 23; SEQ ID NO: 26); a transmembrane domain (amino acid residues 530 to 547 of SEQ ID NO: 23; SEQ ID NO: 27); and an extracellular domain (amino acid residues 548 to 622 of SEQ ID NO: 23; SEQ ID NO: 28).

Figure 2A:
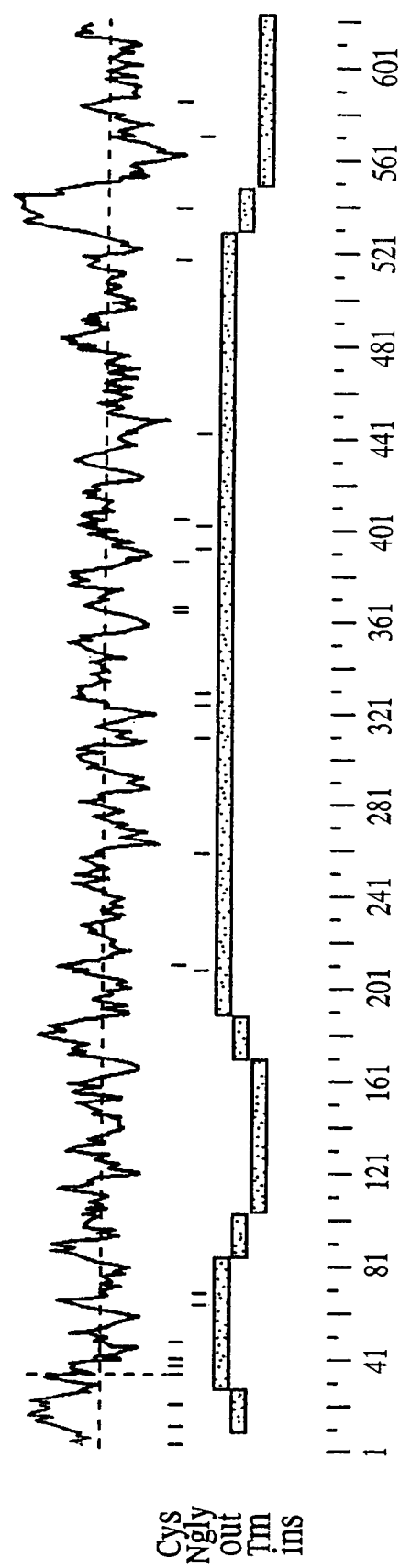
FIG. 2A is a hydrophobicity plot of TANGO 325 protein. An alignment of the amino acid sequences of TANGO 325 ("325"; SEQ ID NO: 23) and Slit-1 protein ("Slit"; SEQ ID NO: 29) protein is shown in FIGS. 2B–2G.

FIG. 2A depicts a hydrophobicity plot of human TANGO 325 protein. Relatively hydrophobic regions are above the dashed horizontal line, and relatively hydrophilic regions are below the dashed horizontal line. The hydrophobic region which corresponds to amino acid residues 1 to 31 of SEQ ID NO: 23 is the signal sequence of human TANGO 325 (SEQ ID NO: 24). The hydrophobic region which corresponds to amino acid residues 530 to 547 of SEQ ID NO: 23 is the transmembrane domain of human TANGO 325 (SEQ ID NO: 27). As described elsewhere herein, relatively hydrophilic regions are generally located at or near the surface of a protein, and are more frequently effective immunogenic epitopes than are relatively hydrophobic regions. For example, the region of human TANGO 325 protein from about amino acid residue 550 to about amino acid residue 565 appears to be located at or near the surface of the protein, while the region from about amino acid residue 168 to about amino acid residue 185 appears not to be located at or near the surface.

The predicted molecular weight of human TANGO 325 protein without modification and prior to cleavage of the signal sequence is about 70.3 kilodaltons. The predicted molecular weight of the mature human TANGO 325 protein without modification and after cleavage of the signal sequence is about 66.8 kilodaltons.

Northern analysis experiments indicated that mRNA corresponding to the cDNA encoding TANGO 325 is expressed in the tissues listed in Table V, wherein "+" indicates expression and "−" indicates that expression could not be detected in the corresponding tissue.

TABLE V

| Animal | Tissue | Relative Level of Expression |
|---|---|---|
| Human | placenta | + |
|  | liver | + |
|  | kidney | + |
|  | pancreas | + |
|  | heart | + |
|  | brain | − |
|  | skeletal muscle | − |
|  | lung | − |

Uses of TANGO 325 Nucleic Acids, Polypeptides, and Modulators thereof

TANGO 325 proteins are involved in disorders which affect both tissues in which they are normally expressed and tissues in which they are normally not expressed. Based on the observation that TANGO 325 is expressed in human aortic endothelial tissue and in placenta, liver, kidney, pancreas, and heart tissues, TANGO 325 protein is involved in one or more biological processes which occur in these tissues. In particular, TANGO 325 is involved in modulating growth, proliferation, survival, differentiation, and activity of endothelial cells including, but not limited to, vascular and cardiac (including valvular) endothelial cells of the animal in which it is normally expressed. TANGO 325 also modulates growth, proliferation, survival, differentiation, and activity of placenta, liver, kidney, and pancreas cells. Thus, TANGO 325 has a role in disorders which affect these cells and their growth, proliferation, survival, differentiation, and activity. TANGO 325 polypeptides, nucleic acids, or modulators thereof can be used to prognosticate, diagnose, inhibit, prevent, or alleviate one or more of these disorders.

In one example, TANGO 325 polypeptides, nucleic acids, and modulators thereof can be used to treat placental disorders, such as the placental disorders described elsewhere in this disclosure. TANGO 325 polypeptides, nucleic acids, or modulators thereof can be used to prognosticate, diagnose, inhibit, prevent, or alleviate one or more of these disorders.

In another example, TANGO 325 polypeptides, nucleic acids, and modulators thereof, can be used to treat hepatic (i.e., liver) disorders, such as the hepatic disorders described elsewhere in this disclosure. TANGO 325 polypeptides, nucleic acids, or modulators thereof can be used to prognosticate, diagnose, inhibit, prevent, or alleviate one or more of these disorders.

In another example, TANGO 325 polypeptides, nucleic acids, or modulators thereof, can be used to treat renal (i.e., kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), and tumors (e.g., renal cell carcinoma and nephroblastoma). TANGO 325 polypeptides, nucleic acids, or modulators thereof can be used to prognosticate, diagnose, inhibit, prevent, or alleviate one or more of these disorders.

Pancreatic disorders in which TANGO 325 can be involved include the pancreatic disorders described elsewhere in this disclosure. TANGO 325 polypeptides, nucleic acids, or modulators thereof can be used to prognosticate, diagnose, inhibit, prevent, or alleviate one or more of these disorders.

Because TANGO 325 exhibits expression in the heart, TANGO 325 nucleic acids, proteins, and modulators thereof can be used to treat cardiovascular disorders. Examples of heart disorders with which TANGO 325 can be involved include the cardiovascular disorders described elsewhere in this disclosure. TANGO 325 polypeptides, nucleic acids, or modulators thereof can be used to prognosticate, diagnose, inhibit, prevent, or alleviate one or more of these disorders.

It is known that serum nucleotide levels (e.g., ATP) affect cardiac contractility and vasomotor tone. Presence in TANGO 325 of an ATP/GTP binding domain in the extracellular portion thereof implicates this transmembrane protein in sensing of serum nucleotide levels and transmission of the sensed level by mechanisms not yet fully understood to myocytes underlying the epithelium. Thus, TANGO 325 is involved in disorders such as cardiovascular insufficiency, hypertension, hypotension, shock, and the like.

Leukocytes are known to bind with vascular endothelial surfaces in a reversible manner prior to penetrating the vascular endothelium in route to an underlying tissue. Although a few proteins have previously been implicated in the leukocyte-endothelium binding process, the identities of all of the proteins involved remain unknown. The presence of numerous LRR domains on the exterior portion of TANGO 325 protein implicates this protein in reversible binding of leukocytes to vascular endothelium. Thus, TANGO 325 is involved in physiological processes and disorders which involve leukocyte-endothelium binding. Such processes and disorders include, by way of example, cellular aspects of immune responses, autoimmune responses and disorders, and migration of leukocytes to lymph nodes.

The aortic endothelium, as well as other vascular endothelia, are known to be involved in detection of signals (e.g., metabolites, proteins, and the like) in the blood stream. Mammalian Slit-1 protein is known to be involved in the human endocrine system (Itoh et al. (1998) Brain Res. Mol. Brain Res. 62:175–186). Amino acid and nucleic acid sequence similarity of TANGO 325 with human Slit-1 protein, as described herein, indicates that TANGO 325 is involved in sensing physiological signals by the endocrine system. Thus, TANGO 325 is involved in one or more human endocrine disorders such as pituitary disorders (e.g., diabetes insipidus), thyroid disorders (e.g., hyperthyroidism, hypothyroidism, diabetes, goiter, and growth and developmental disorders), adrenal disorders (e.g., Addison's disease, Cushing's syndrome, hyperaldosteronism, and pheochromocytoma), and the like.

Human Slit-1 protein is also known to be involved in guidance of neuronal growth. The sequence similarity of TANGO 325 with Slit-1, as described herein, implicates TANGO 325 in growth, development, maintenance, and regeneration of neurons. TANGO 325 can thus be used to prevent, diagnose, and treat a variety of neurological disorders.

TANGO 364 cDNA clones (designated jthke076a05 and jthkf069g11) encoding at least a portion of human TANGO 364 protein were isolated from a human fetal skin cDNA library by computerized sequence analysis of library ORFs which encode a signal sequence (SPOT analysis). Human TANGO 364 protein is predicted by structural analysis to be a transmembrane protein.

The full length of the cDNA encoding human TANGO 364 protein (SEQ ID NO: 31) is 3510 nucleotide residues. The ORF of this cDNA, nucleotide residues 235 to 1764 of SEQ ID NO: 31 (i.e., SEQ ID NO: 32), encodes a 510-amino acid residue protein (SEQ ID NO: 33), corresponding to a 479-residue transmembrane protein. TANGO 364 cDNA can exist in an alternatively-spliced form. In this alternative form, TANGO 364 cDNA is 2510 nucleotide residues in length (SEQ ID NO: 41). The ORF of this cDNA, nucleotide residues 2 to 898 of SEQ ID NO: 41 (i.e., SEQ ID NO: 42), encodes a 299-amino acid residue protein (SEQ ID NO: 43) which has the same sequence as the portions of full length TANGO 364 protein indicated in the alignment (made using the ALIGN software; pam120.mat scoring matrix; gap penalties −12/−4) listed in FIGS. 3B and 3C. In the discussion which follows, the full length and alternatively-spliced forms of TANGO 364 molecules are referred to individually and collectively as TANGO 364 molecules of the corresponding type (e.g., cDNA and protein).

The invention thus includes purified human TANGO 364 protein, both in the form of the immature 510 amino acid residue protein (SEQ ID NO: 33) and in the form of the mature 479 amino acid residue protein (SEQ ID NO: 35). Mature human TANGO 364 proteins can be synthesized without the signal sequence polypeptide at the amino terminus thereof, or it can be synthesized by generating immature TANGO 364 protein and cleaving the signal sequence therefrom.

The invention also includes nucleic acid molecules which encode a polypeptide of the invention. Such nucleic acids include, for example, a DNA molecule having the nucleotide sequence listed in SEQ ID NO: 31 or some portion thereof, such as the portion which encodes mature human TANGO 364 protein, immature human TANGO 364 protein, or a domain of human TANGO 364 protein. These nucleic acids are collectively referred to as nucleic acids of the invention.

TANGO 364 proteins and nucleic acid molecules encoding them comprise a family of molecules having certain conserved structural and functional features.

A common domain present in TANGO 364 proteins is a signal sequence. In one embodiment, a TANGO 364 protein contains a signal sequence corresponding to the portion of the protein from amino acid residue 1 to about amino acid residue 31 of SEQ ID NO: 33 (SEQ ID NO: 34). It is recognized that the carboxyl terminal boundary of the signal sequence can be located one or two residues from the residue identified above (i.e., at residue 29, 30, 31, 32, or 33 of SEQ ID NO: 33). The signal sequence is cleaved during processing of the mature protein.

TANGO 364 proteins can include an extracellular domain. The human TANGO 364 protein extracellular domain is located from about amino acid residue 32 to amino acid residue 345 of SEQ ID NO: 33 (i.e., the extracellular domain has the sequence SEQ ID NO: 36).

In addition, TANGO 364 can include a transmembrane domain. In one embodiment, a TANGO 364 protein of the invention contains a transmembrane domain corresponding to about amino acid residues 346 to 370 of SEQ ID NO: 33 (i.e., the transmembrane domain has the sequence SEQ ID NO: 37).

The present invention includes TANGO 364 proteins having a cytoplasmic domain, particularly including proteins having a carboxyl-terminal cytoplasmic domain. As used herein, a "cytoplasmic domain" refers to a portion of a protein which is localized to the cytoplasmic side of a lipid bilayer of a cell when a nucleic acid encoding the protein is expressed in the cell. The human TANGO 364 cytoplasmic domain is located from about amino acid residue 371 to amino acid residue 510 of SEQ ID NO: 33 (i.e., the cytoplasmic domain has the sequence SEQ ID NO: 38).

In an alternative embodiment, TANGO 364 proteins have a cytoplasmic domain located from about amino acid residue 32 to amino acid residue 345 of SEQ ID NO: 33 (i.e., the extracellular domain has the sequence SEQ ID NO: 36); a transmembrane domain corresponding to about amino acid residues 346 to 370 of SEQ ID NO: 33 (i.e., the transmembrane domain has the sequence SEQ ID NO: 37); and an extracellular domain located from about amino acid residue 371 to amino acid residue 510 of SEQ ID NO: 33 (i.e., the extracellular domain has the sequence SEQ ID NO: 38).

TANGO 364 proteins typically comprise a variety of potential post-translational modification sites (often within an extracellular domain), such as those described herein in Table VI, as predicted by computerized sequence analysis of TANGO 364 proteins using amino acid sequence comparison software (comparing the amino acid sequence of TANGO 364 with the information in the PROSITE database {rel. 12.2; February, 1995} and the Hidden Markov Models database {Rel. PFAM 3.3}).

TABLE VI

| Type of Potential Modification Site or Domain | Amino Acid Residues of SEQ ID NO: 33 | Amino Acid Sequence |
| --- | --- | --- |
| N-glycosylation site | 281 to 284 | NWTR |
| | 430 to 433 | NSSC |
| | 489 to 492 | NGTL |
| Protein kinase C phosphorylation site | 26 to 28 | TGR |
| | 192 to 194 | SSR |
| | 195 to 197 | SFK |
| | 249 to 251 | SVR |
| | 322 to 324 | SSR |
| | 339 to 341 | SGK |
| | 383 to 385 | TQK |
| | 397 to 399 | SIR |
| | 426 to 428 | SLK |
| | 450 to 452 | TVR |
| | 465 to 467 | SGR |
| | 491 to 493 | TLR |
| Casein kinase II phosphorylation site | 283 to 286 | TRLD |
| | 322 to 325 | SSRD |
| | 410 to 413 | SQPE |
| | 426 to 429 | SLKD |
| | 450 to 453 | TVRE |
| | 456 to 459 | TQTE |
| N-myristoylation site | 135 to 140 | GSFQAR |
| | 162 to 167 | GQGLTL |
| | 189 to 194 | GTTSSR |
| | 218 to 223 | GQPLTC |
| | 311 to 316 | GIYVCH |
| | 354 to 359 | GVIAAL |
| | 464 to 469 | GSGRAE |
| | 477 to 482 | GIKQAM |
| | 490 to 495 | GTLRAK |
| | 500 to 505 | GIYING |

TABLE VI-continued

| Type of Potential Modification Site or Domain | Amino Acid Residues of SEQ ID NO: 33 | Amino Acid Sequence |
|---|---|---|
| Cell attachment sequence | 55 to 57 | RGD |
| Immunoglobulin-/major histocompatibility protein-like (Ig-/MHC-like) domain | 45 to 129<br>162 to 225<br>263 to 317 | See FIG. 3 |

In various embodiments, the protein of the invention has at least 1, 2, 4, 6, 10, 15, or 20 or more of the post-translational modification sites described herein in Table VI.

Examples of additional domains present in human TANGO 364 protein include the RGD cell attachment sequence and Ig-/MHC-like domains. In one embodiment, the protein of the invention has at least one domain that is at least 55%, preferably at least about 65%, more preferably at least about 75%, yet more preferably at least about 85%, and most preferably at least about 95% identical to one of the Ig-/MHC-like domains described herein in Table VI. Preferably, the protein of the invention has at least one Ig-/MHC-like domain and one RGD cell attachment sequence.

Ig-/MHC-like domains are conserved among immunoglobulin (Ig) constant (CL) regions and one of the three extracellular domains of major histocompatibility proteins (MHC). Ig-/MHC-like domains are involved in protein-to-protein and protein-to-ligand binding.

The signal peptide prediction program SIGNALP (Nielsen et al. (1997) Protein Engineering 10:1–6) predicted that human TANGO 364 protein includes an approximately 31 amino acid signal peptide (amino acid residues 1 to about 31 of SEQ ID NO: 33; SEQ ID NO: 34) preceding the mature TANGO 364 protein (amino acid residues 32 to 510 of SEQ ID NO: 33; SEQ ID NO: 35). Human TANGO 364 protein includes an extracellular domain (amino acid residues 32 to 345 of SEQ ID NO: 33; SEQ ID NO: 36), a transmembrane domain (amino acid residues 346 to 370 of SEQ ID NO: 33; SEQ ID NO: 37), and a cytoplasmic domain (amino acid residues 371 to 510 of SEQ ID NO: 33; SEQ ID NO: 38).

Figure 3A:
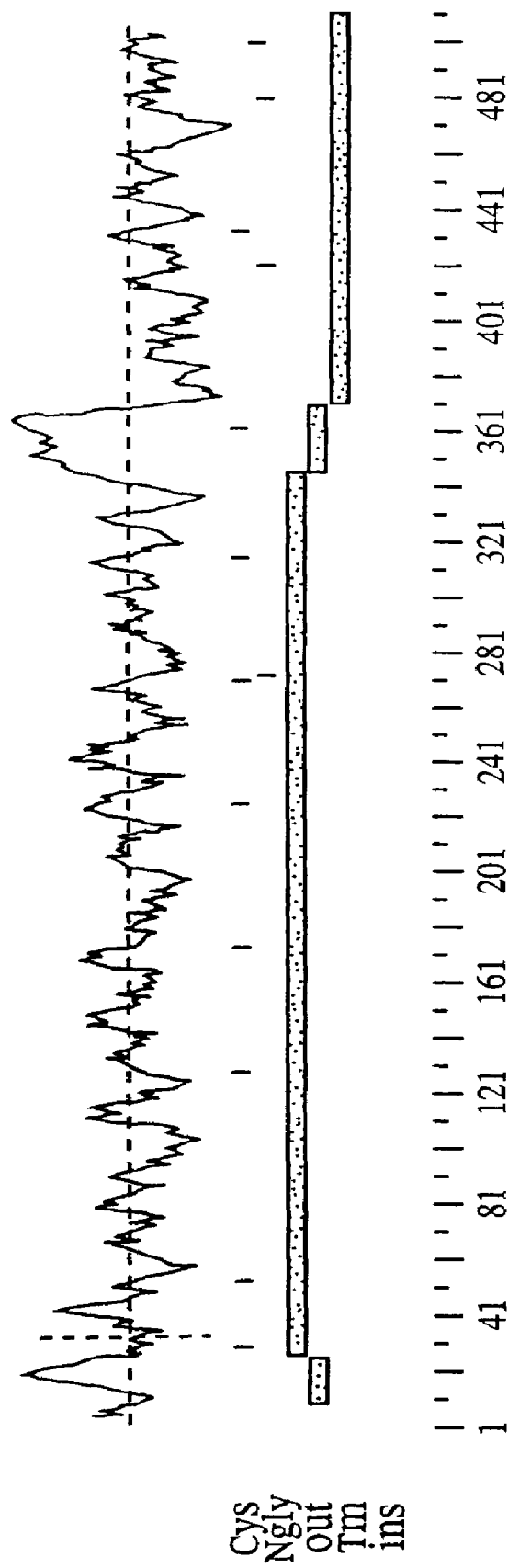
FIG. 3A is a hydrophobicity plot of human TANGO 364 protein.

FIG. 3A depicts a hydrophobicity plot of human TANGO 364 protein. Relatively hydrophobic regions are above the dashed horizontal line, and relatively hydrophilic regions are below the dashed horizontal line. The hydrophobic region which corresponds to amino acid residues 1 to about 31 of SEQ ID NO: 33 is the signal sequence of human TANGO 364 (SEQ ID NO: 34), and the hydrophobic region which corresponds to amino acid residues 346 to 370 of SEQ ID NO: 33 is the transmembrane region of TANGO 364 (SEQ ID NO: 37). As described elsewhere herein, relatively hydrophilic regions are generally located at or near the surface of a protein, and are more frequently effective immunogenic epitopes than are relatively hydrophobic regions. For example, the region of human TANGO 364 protein from about amino acid residue 371 to about amino acid residue 410 appears to be located at or near the surface of the protein, while the region from about amino acid residue 235 to about amino acid residue 245 appears not to be located at or near the surface.

The predicted molecular weight of human TANGO 364 protein without modification and prior to cleavage of the signal sequence is about 55.5 kilodaltons. The predicted molecular weight of the mature human TANGO 364 protein without modification and after cleavage of the signal sequence is about 52.1 kilodaltons.

TANGO 364 exhibits limited sequence similarity to numerous cell surface proteins, including proteins which serve as cell surface antigens, proteoglycans, and virus receptors.

Uses of TANGO 364 Nucleic Acids, Polypeptides, and Modulators thereof

TANGO 364 proteins are involved in disorders which affect both tissues in which they are normally expressed and tissues in which they are normally not expressed. Based on the observations that cDNA corresponding to TANGO 364 occurs in a human fetal skin cDNA library, it is evident that TANGO 364 protein is involved in one or more biological processes which occur in skin tissues. In particular, TANGO 364 is involved in modulating one or more of growth, proliferation, survival, differentiation, activity, morphology, and movement/migration of skin cells. Thus, TANGO 364 has a role in disorders which affect skin cells and one or more of their growth, proliferation, survival, differentiation, activity, morphology, and movement/migration, as well as the biological function of skin.

There are several indications that TANGO 364 is a cell surface protein which is involved in binding a ligand to the cell which expresses the protein. For instance, presence in TANGO 364 of an amino terminal extracellular domain that includes three Ig-/MHC-like domains exemplifies the cell-surface ligand-binding capability of TANGO 364. In addition, the amino acid sequence similarity which TANGO 364 exhibits with respect to several other cell surface ligand-binding proteins reinforces this view. Presence in TANGO 364 of an Ig-/MHC-like domain indicates that the corresponding region of TANGO 364 is structurally similar to this conserved extracellular region, and that TANGO 364 is involved in binding one or more of a ligand and a protein (including, for example, a serum protein and a cell-surface protein of another cell). Thus, molecules (e.g., antibodies and short peptides) which are able to interact specifically with an Ig-/MHC-like domain of a TANGO 364 protein can inhibit binding of TANGO 364 with its normal ligand, thereby disrupting one or more physiological processes associated with such binding. Furthermore, polypeptides (including, for example, full-length TANGO 364 protein and polypeptides of at least about 25 to 50 amino acid residues) which comprise all or part of an Ig-/MHC-like domain of TANGO 364 can bind with one or more of the normal ligands of TANGO 364, thereby replicating the normal physiological effect of binding between TANGO 364 and the ligand or inhibiting binding of endogenous TANGO 364 with the ligand. Therefore, TANGO 364 protein, polypeptides having at least one Ig-/MHC-like domain thereof, and molecules capable of interacting with such a domain are useful for prognosticating, diagnosing, treating, and inhibiting disorders associated with aberrant binding of TANGO 364 and its normal ligand.

TANGO 364 is involved in binding an animal cell which expresses it with one or more of a protein (e.g., an antibody, an major histocompatibility protein, a lectin, or another cell surface protein), a small molecule (e.g., a sugar, a hormone, or another molecule having a molecular weight less than about 5000, 1000, or 500 or less Daltons), a component of the extracellular matrix (e.g., a collagen protein), another cell of the same animal, a bacterial or fungal cell, and a virus. Thus, TANGO 364 is involved in modulating cell-to-cell adhesion, tissue and extracellular matrix invasivity of cells, infectivity of cells by pathogens (e.g., bacteria and viruses), endocrine signaling processes, tissue developmental and organizational processes, and the like. Thus, TANGO 364 is involved in disorders in which these physiological processes are relevant.

Disorders associated with aberrant cell-to-cell adhesion include tumor growth and metastasis, malformation or degradation of neurological connections, autoimmune disorders, immune insufficiency disorders, atherosclerosis, arteriosclerosis, abnormal blood coagulation, and the like. Disorders associated with tissue and extracellular matrix invasivity of cells include tumor metastasis, osteoporosis, inflammation, and the like. Disorders associated with pathogenic infections include infections associated with bacteria, fungi, mycoplasmas, viruses, eukaryotic parasites, and the like. Disorders associated with aberrant endocrine signaling processes include, for example, diabetes mellitus, hypoglycemia, glucagon disorders, pituitary disorders (e.g., diabetes insipidus), thyroid disorders (e.g., hyper- and hypothyroidism), adrenal disorders (e.g., Addison's disease, adrenal virilism, Cushing's syndrome, and hyperaldosteronism), multiple endocrine neoplasias, and polyglandular deficiency syndromes. Disorders associated with aberrant tissue developmental and organizational processes include, for example, birth defects, benign and malignant carcinogenesis, neurodegenerative disorders (e.g., Alzheimer's disease), and the like. TANGO 364 proteins, nucleic acids encoding them, and agents (e.g., antibodies, peptides, and small molecules) that modulate activity or expression of either of these can be used to prognosticate, diagnose, treat, and inhibit one or more of these disorders.

TANGO 405

A cDNA clone (designated jthLa152h06) encoding at least a portion of human TANGO 405 protein was isolated from a human mixed lymphocyte reaction cDNA library. A corresponding murine cDNA (designated jtmMa025a11) was isolated from a long-term bone marrow cDNA library. Human and murine TANGO 405 proteins are secreted proteins.

The full length of the cDNA encoding human TANGO 405 protein (SEQ ID NO: 51) is 3114 nucleotide residues in length. The open reading frame (ORF) of this cDNA, nucleotide residues 154 to 780 of SEQ ID NO: 51 (i.e., SEQ ID NO: 52), encodes a 209-amino acid residue protein (SEQ ID NO: 53), corresponding to a 161-residue secreted protein.

The invention thus includes purified human TANGO 405 protein, both in the form of the immature 209 amino acid residue protein (SEQ ID NO: 53) and in the form of the mature 161 amino acid residue protein (SEQ ID NO: 55). The invention also includes purified murine TANGO 405 protein, both in the form of the immature 178-amino acid residue protein (SEQ ID NO: 63) and in the form of the mature, secreted 136-amino acid residue protein (SEQ ID NO: 65). Mature human or murine TANGO 405 protein can be synthesized without the signal sequence polypeptide at the amino terminus thereof, or they can be synthesized by generating immature TANGO 405 protein and cleaving the signal sequence therefrom.

The invention also includes nucleic acid molecules which encode a polypeptide of the invention. Such nucleic acids include, for example, a DNA molecule having the nucleotide sequence listed in SEQ ID NO: 51 or some portion thereof or SEQ ID NO: 61 or some portion thereof, such as the portion which encodes mature human or murine TANGO 405 protein, immature human or murine TANGO 405 protein, or a domain of human or murine TANGO 405 protein. These nucleic acids are collectively referred to as nucleic acids of the invention.

TANGO 405 proteins and nucleic acid molecules encoding them comprise a family of molecules having certain conserved structural and functional features.

A common domain present in TANGO 405 proteins is a signal sequence. In one embodiment, a TANGO 405 protein contains a signal sequence corresponding to the portion of the protein from amino acid residue 1 to about amino acid residue 48 of SEQ ID NO: 53 (SEQ ID NO: 54) or to the portion of the protein from amino acid residue 1 to about amino acid residue 42 of SEQ ID NO: 63 (SEQ ID NO: 64). It is recognized that the carboxyl terminal boundary of the signal sequence can be located one or two residues from the residue identified above (i.e., at residue 46, 47, 48, 49, or 50 of SEQ ID NO: 53 or at residue 40, 41, 42, 43 or 44 of SEQ ID NO: 63). The signal sequence is cleaved during processing of the mature protein.

TANGO 405 proteins typically comprise a variety of potential post-translational modification sites (often within an extracellular domain), such as those described herein in Table VII (for human TANGO 405) and VIII (for murine TANGO 405), as predicted by computerized sequence analysis of TANGO 405 proteins using amino acid sequence comparison software (comparing the amino acid sequence of TANGO 405 with the information in the PROSITE database {rel. 12.2; February, 1995} and the Hidden Markov Models database {Rel. PFAM 3.3}).

TABLE VII

| Type of Potential Modification Site or Domain | Amino Acid Residues of SEQ ID NO: 53 | Amino Acid Sequence |
|---|---|---|
| N-glycosylation site | 131 to 134 | NESF |
|  | 170 to 173 | NHSA |
| cAMP- or cGMP-dependent protein kinase phosphorylation site | 52 to 55 | KRLS |
|  | 197 to 200 | RRNS |
| Protein kinase C phosphorylation site | 10 to 12 | TEK |
|  | 17 to 19 | SLR |
|  | 50 to 52 | TGK |
|  | 82 to 84 | SWK |
|  | 196 to 198 | TRR |
| Casein kinase II phosphorylation site | 46 to 49 | TYGE |
|  | 94 to 97 | SSEE |
|  | 101 to 104 | SKSE |
|  | 119 to 122 | TEAE |
|  | 155 to 158 | TPYE |
|  | 200 to 203 | SICE |
| Tyrosine kinase phosphorylation site | 52 to 60 | KRLSELHSY |
| N-myristoylation site | 25 to 30 | GISIAL |
|  | 77 to 82 | GCCPAS |
| Amidation site | 50 to 53 | TGKR |
| C-type lectin domain signature | 176 to 202 | See FIG. 4 |
| C-type lectin domain | 105 to 202 | See FIG. 4 |

TABLE VIII

| Type of Potential Modification Site or Domain | Amino Acid Residues of SEQ ID NO: 63 | Amino Acid Sequence |
|---|---|---|
| N-glycosylation site | 136 to 139 | NESL |
|  | 155 to 158 | NGSM |
| Protein kinase C phosphorylation site | 20 to 22 | TLR |
|  | 54 to 56 | SRR |
|  | 77 to 79 | SEK |
|  | 99 to 101 | STK |
|  | 162 to 164 | SVK |
| Casein kinase II phosphorylation site | 99 to 102 | STKE |
|  | 106 to 109 | STSE |
|  | 124 to 127 | TEAE |
| Tyrosine kinase phosphorylation site | 55 to 63 | RRLYELHTY |

TABLE VIII-continued

| Type of Potential Modification Site or Domain | Amino Acid Residues of SEQ ID NO: 63 | Amino Acid Sequence |
|---|---|---|
| N-myristoylation site | 16 to 21 | GVCWTL |
|  | 73 to 78 | GTMVSE |
|  | 82 to 87 | GCCPNH |
| C-type lectin domain | 110 to 180 | See FIG. 4 |

In various embodiments, the protein of the invention has at least 1, 2, 4, 6, 10, 15, or 20 or more of the post-translational modification sites described herein in Tables VII and VIII.

Examples of additional domains present in human and murine TANGO 405 protein include a C-type lectin domain and a corresponding signature sequence. In one embodiment, the protein of the invention has a C-type lectin domain or signature sequence that is at least 55%, preferably at least about 65%, more preferably at least about 75%, yet more preferably at least about 85%, and most preferably at least about 95% identical to one of those described herein in Tables VII and VIII.

C-type lectin domains are conserved among proteins (e.g., animal lectins) which are involved in calcium-dependent binding of carbohydrates, although it has recently been recognized that these domains can also be involved in binding of proteins (Drickamer, 1988, J. Biol. Chem. 263: 9557–9560; Drickamer, 1993, Prog. Nucl. Acid Res. Mol. Biol. 45:207–232; Drickamer, 1993, Curr. Opin. Struct. Biol. 3:393–400). C-type lectins and their relevant properties are described in greater in P.C.T. Publication No. WO 98/28332, which, as with all references cited herein, is incorporated by reference.

In PCT Publication No. WO 98/28332, a cDNA encoding murine protein, designated dectin-2, was isolated from dendritic cells and described. Human and murine TANGO 405 proteins exhibit amino acid sequence homology with murine dectin-2. As indicated in the alignment in FIG. 4H (made using the ALIGN software; pam120.mat scoring matrix; gap penalties −12/−4), human TANGO 405 exhibits about 89.0% sequence identity with murine dectin-2. As indicated in the alignment in FIG. 4G (made using the ALIGN software; pam120.mat scoring matrix; gap penalties −12/−4), murine TANGO 405 exhibits about 70.3% sequence identity with murine dectin-2.

Another embodiment of a murine TANGO 405 cDNA is shown in the cDNA having the sequence SEQ ID NO: 71 and the ORF having the nucleotide sequence SEQ ID NO: 72. In this embodiment murine TANGO 405 includes a translational frame shift, and the amino acid sequence (SEQ ID NO: 73) of murine TANGO 405 is identical to the amino acid sequence reported for murine dectin-2. These data further confirm that human TANGO 405 is the human ortholog of murine dectin-2.

The signal peptide prediction program SIGNALP (Nielsen et al. (1997) Protein Engineering 10:1–6) predicted that human TANGO 405 protein includes an approximately 48 amino acid signal peptide (amino acid residues 1 to about 48 of SEQ ID NO: 53; SEQ ID NO: 54) preceding the mature TANGO 405 protein (amino acid residues 49 to 209 of SEQ ID NO: 53; SEQ ID NO: 55). It is recognized that both human and murine TANGO 405 can, at least transiently, exist in an integral membrane form, at least until cleavage of the corresponding signal sequence (i.e., either during or following translation of the complete TANGO 405 protein).

Figure 4A:
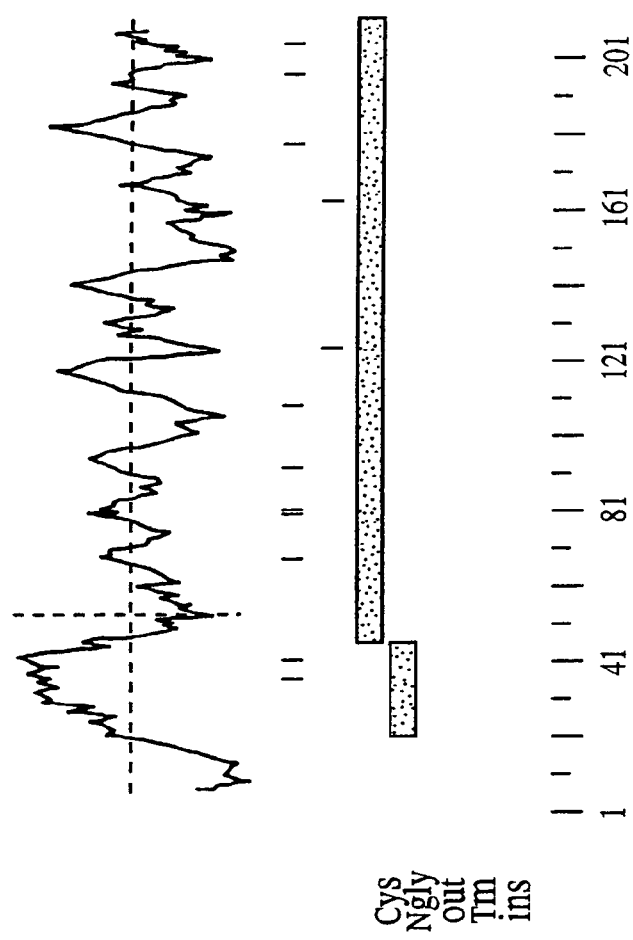
FIG. 4A is a hydrophobicity plot of human TANGO 405 protein.

FIG. 4A depicts a hydrophobicity plot of human TANGO 405 protein. Relatively hydrophobic regions are above the dashed horizontal line, and relatively hydrophilic regions are below the dashed horizontal line. The hydrophobic region which corresponds to amino acid residues 1 to about 48 of SEQ ID NO: 53 is the signal sequence of human TANGO 405 (SEQ ID NO: 54). As described elsewhere herein, relatively hydrophilic regions are generally located at or near the surface of a protein, and are more frequently effective immunogenic epitopes than are relatively hydrophobic regions. For example, the region of human TANGO 405 protein from about amino acid residue 90 to about amino acid residue 105 appears to be located at or near the surface of the protein, while the region from about amino acid residue 110 to about amino acid residue 120 appears not to be located at or near the surface.

The predicted molecular weight of human TANGO 405 protein without modification and prior to cleavage of the signal sequence is about 24.0 kilodaltons. The predicted molecular weight of the mature human TANGO 405 protein without modification and after cleavage of the signal sequence is about 18.6 kilodaltons.

The full length of the cDNA encoding murine TANGO 405 protein (SEQ ID NO: 61) is 821 nucleotide residues, although this cDNA sequence is incomplete. The ORF of this cDNA, nucleotide residues 174 to 707 of SEQ ID NO: 61 (i.e., SEQ ID NO: 62), encodes a protein comprising at least 178 amino acid residues (SEQ ID NO: 63).

The signal peptide prediction program SIGNALP (Nielsen et al. (1997) Protein Engineering 10:1–6) predicted that murine TANGO 405 protein includes an approximately 42 amino acid signal peptide (amino acid residues 1 to about 42 of SEQ ID NO: 63; SEQ ID NO: 64) preceding the mature TANGO 405 protein (amino acid residues 43 to 178 of SEQ ID NO: 63; SEQ ID NO: 65). Murine TANGO 405 protein is a secreted protein.

Figure 4B:
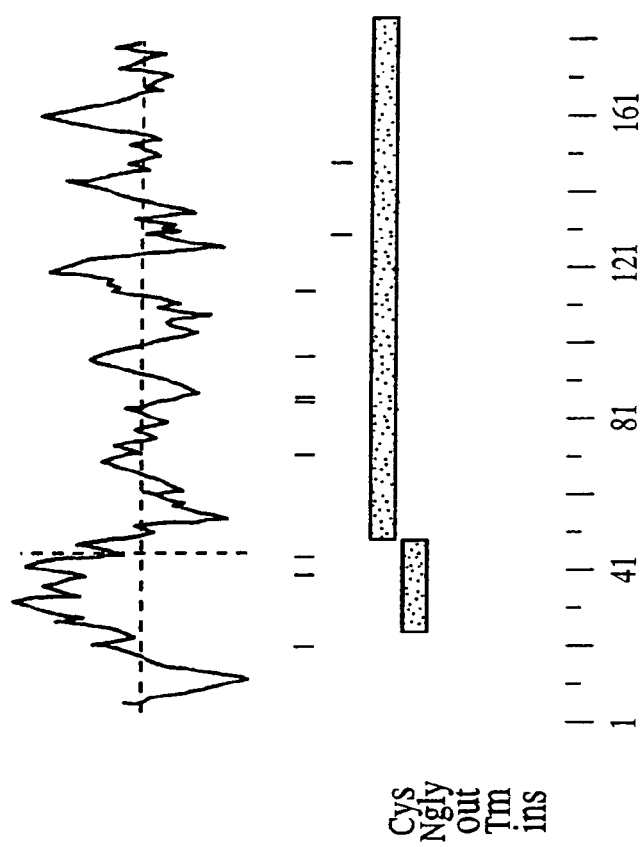
FIG. 4B is a hydrophobicity plot of murine TANGO 405 protein. An alignment of the amino acid sequences of human TANGO 405 protein (SEQ ID NO: 53) and murine TANGO 405 protein (SEQ ID NO: 63) amino acid sequences is shown in FIG. 4C. An alignment of the nucleotide sequences of the human (SEQ ID NO: 52) and murine (SEQ ID NO: 62) ORFs encoding TANGO 405 protein is shown in FIGS. 4D through 4F.

FIG. 4B depicts a hydrophobicity plot of murine TANGO 405 protein. Relatively hydrophobic regions are above the dashed horizontal line, and relatively hydrophilic regions are below the dashed horizontal line. The hydrophobic region which corresponds to amino acid residues 1 to about 42 of SEQ ID NO: 63 is the signal sequence of murine TANGO 405 (SEQ ID NO: 64). As described elsewhere herein, relatively hydrophilic regions are generally located at or near the surface of a protein, and are more frequently effective immunogenic epitopes than are relatively hydrophobic regions. For example, the region of murine TANGO 405 protein from about amino acid residue 95 to about amino acid residue 110 appears to be located at or near the surface of the protein, while the region from about amino acid residue 110 to about amino acid residue 120 appears not to be located at or near the surface The predicted molecular weight of murine TANGO 405 protein without modification and prior to cleavage of the signal sequence is about 20.0 kilodaltons. The predicted molecular weight of the mature murine TANGO 405 protein without modification and after cleavage of the signal sequence is about 25.3 kilodaltons.

Human and murine TANGO 405 proteins exhibit considerable sequence similarity, as indicated herein in FIG. 4C. FIG. 4C depicts an alignment of human and murine TANGO 405 amino acid sequences (SEQ ID NOs: 53 and 63, respectively). In this alignment (made using the ALIGN software {Myers and Miller (1989) CABIOS, ver. 2.0}; pam120.mat scoring matrix; gap penalties −12/−4), the proteins are 51.7% identical in the overlapping region (i.e., amino acid residues 1–209 of SEQ ID NO: 53 and amino acid residues 1–178 of SEQ ID NO: 63). The human and murine ORFs encoding TANGO 405 are 74.5% identical in the 541 nucleotide residue overlapping region, as assessed using the same software and parameters and as indicated in FIGS. 4D through 4F. The nucleotide sequences encoding human and murine TANGO 405 (i.e., SEQ ID NOs: 51 and 61) are about 71.2% identical in the 838 nucleotide residue overlapping region, as assessed using the LALIGN software (Myers and Miller (1989) CABIOS, ver. 2.0; pam120.mat scoring matrix; gap penalties −12/−4).

Uses of TANGO 405 Nucleic Acids,
Polypeptides, and Modulators thereof

TANGO 405 proteins are involved in disorders which affect both tissues in which they are normally expressed and tissues in which they are normally not expressed. Based on the observations that cDNA corresponding to TANGO 405 occurs in a human mixed lymphocyte reaction cDNA library and in a murine long-term bone marrow cDNA library, it is evident that TANGO 405 protein is involved in one or more biological processes which occur in these tissues (i.e., in blood-related tissues, such as tissues containing lymphocytes). In particular, TANGO 405 is involved in modulating one or more of growth, proliferation, survival, differentiation, activity, morphology, and movement/migration of cells of these tissues. TANGO 405 is involved in modulating the structure of extracellular matrix which contacts or is in fluid communication with cells of these tissues. Thus, TANGO 405 has a role in disorders which affect these cells and one or more of their growth, proliferation, survival, differentiation, activity, morphology, and movement/migration, as well as the biological function of tissues comprising one or more of these types of cells.

Presence of a C-type lectin domain in TANGO 405 is an indication that this protein is capable of specifically recognizing particular surfaces, such as the surface of cells of a particular type. Further supportive of this observation is the fact that human TANGO 405 protein exhibits significant sequence homology with murine dectin-2 protein. Murine dectin-2 has been shown to be expressed by murine dendritic cells, and has also been shown to be involved in activation of naive T cells. Murine dectin-2 can also be involved in inflammatory and non-T cell-mediated immune responses. Thus, human and murine TANGO 405 are also involved in activating or inhibiting one or more types of lymphocytes, thereby modulating T cell-mediated immune responses, non-T cell-mediated immune responses, inflammatory responses, and other components of the immune response in mammals. It is recognized that the amino acid sequence differences among murine dectin-2, human TANGO 405, and murine TANGO 405 can lead to different lymphocyte-activating capacities for these three proteins. Human and murine TANGO 405 proteins are involved both in normal activation of lymphocytes (e.g., in response to the presence of a pathogen in a tissue) and in aberrant activation of lymphocytes (e.g., as in auto-immune and immune inflammatory disorders (e.g., asthma), in disorders characterized by an insufficient immune response, and in disorders characterized by non-controlled proliferation of lymphocytes). TANGO 405 proteins are thus involved in a variety of disorders relating to aberrant lymphocyte activation or proliferation. Examples of disorders include leukemias (e.g., ALL, CML, CLL, and myelodysplastic syndrome), lymphomas (e.g., Hodgkin's disease, non-Hodgkin's lymphoma, Burkitt's lymphoma, and mycosis fungoides), plasma cell dyscrasias, auto-immune disorders such as multiple sclerosis, bacterial and viral infections (e.g., acquired immune deficiency syndrome), leukopenias, eosinophilic disorders such as idiopathic hypereosinophilic syndrome, and the like. TANGO 405 proteins, nucleic acids encoding them, and agents that modulate activity or expression of either of these can be used to prognosticate, diagnose, treat, and inhibit one or more of these disorders.

M019 (Also Designated TANGO 533)

A cDNA encoding at least a portion of human M019 protein was isolated from a human adipose tissue cDNA library. The human M019 protein is predicted by structural analysis to be a secreted protein.

The full length of the cDNA encoding human M019 protein (SEQ ID NO: 81) is 1202 nucleotide residues. The ORF of this cDNA, nucleotide residues 331 to 585 of SEQ ID NO: 81 (SEQ ID NO: 82), encodes a 85-amino acid secreted protein (SEQ ID NO: 83).

The invention thus includes purified human M019 protein, both in the form of the immature 85 amino acid residue protein (SEQ ID NO: 83) and in the form of the mature 62 amino acid residue protein (SEQ ID NO: 85). Mature human M019 protein can be synthesized without the signal sequence polypeptide at the amino terminus thereof, or it can be synthesized by generating immature M019 protein and cleaving the signal sequence therefrom.

The invention also includes nucleic acid molecules which encode a polypeptide of the invention. Such nucleic acids include, for example, a DNA molecule having the nucleotide sequence listed in SEQ ID NO: 81 or some portion thereof, such as the portion which encodes mature M019 protein, immature M019 protein, or a domain of M019 protein. These nucleic acids are collectively referred to as nucleic acids of the invention.

M019 proteins and nucleic acid molecules encoding them comprise a family of molecules having certain conserved structural and functional features. Each of these molecules is included in the invention. As used herein, the term "family" is intended to mean two or more proteins or nucleic acid molecules having a common or similar domain structure and having sufficient amino acid or nucleotide sequence identity as defined herein. Family members can be from either the same or different species. For example, a family can comprise two or more proteins of human origin, or can comprise one or more proteins of human origin and one or more of non-human origin.

A common domain present in M019 proteins is a signal sequence. In one embodiment, a M019 protein contains a signal sequence corresponding to amino acid residues 1 to 23 of SEQ ID NO: 83 (SEQ ID NO: 84). The signal sequence is cleaved during processing of the mature protein.

M019 proteins are secreted proteins, and thus include an 'extracellular domain,' both in the mature protein (i.e., wherein the entire mature protein is an 'extracellular domain') and in the immature protein (e.g., wherein the signal sequence, residues 1–23 of SEQ ID NO: 83, is embedded in the membrane prior to cleavage, and the remainder of the protein, about residues 24–85 is extracellular). As used herein, an "extracellular domain" refers to a portion of a protein which is localized to the non-cytoplasmic side of a lipid bilayer of a cell when a nucleic acid encoding the protein is expressed in the cell.

M019 proteins typically comprise a variety of potential post-translational modification sites (often within an extracellular domain), such as those described herein in Table IX, as predicted by computerized sequence analysis of M019 proteins using amino acid sequence comparison software (comparing the amino acid sequence of M019 with the information in the PROSITE database {rel. 12.2; February, 1995} and the Hidden Markov Models database {Rel. PFAM 3.3 }). In certain embodiments, a protein of the invention has at least 1, 2, 3, or all 4 of the post-translational modification sites listed in Table IX.

TABLE IX

| Type of Potential Modification Site or Domain | Amino Acid Residues of SEQ ID NO: 83 | Amino Acid Sequence |
|---|---|---|
| Protein kinase C phosphorylation site | 47 to 49 | SNR |
|  | 75 to 77 | TMK |
| Casein kinase II phosphorylation site | 47 to 50 | SNRE |
| N-myristoylation site | 34 to 49 | GQDSNL |

M019 exhibits no significant amino acid sequence similarity with any known protein. Thus, M019 appears to be a novel protein.

Figure 5A:
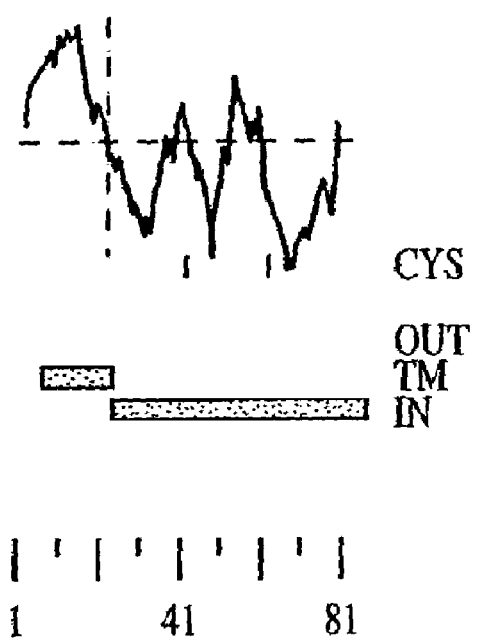
FIG. 5A is a hydrophobicity plot of human M019 protein, in which the locations of cysteine residues ("Cys"), and the predicted extracellular ("out"), intracellular ("ins"), or transmembrane ("TM") locations of the protein backbone is indicated by a horizontal bar.

FIG. 5A depicts a hydrophobicity plot of human M019 protein. Relatively hydrophobic regions are above the dashed horizontal line, and relatively hydrophilic regions are below the dashed horizontal line. The hydrophobic region which corresponds to amino acid residues Ito 23 of SEQ ID NO: 83 is the signal sequence of human M019 (SEQ ID NO: 84). As described elsewhere herein, relatively hydrophilic regions are generally located at or near the surface of a protein, and are more frequently effective immunogenic epitopes than are relatively hydrophobic regions. For example, the region of human M019 protein from about amino acid residue 63 to about amino acid residue 80 appears to be located at or near the surface of the protein, while the region from about amino acid residue 55 to about amino acid residue 60 appears not to be located at or near the surface.

By virtue of its size and the presence of a pair of cysteine residues in its mature form, M019 resembles chemokine molecules, and it therefore believed to be involved in modulating adipose tissue processes involving interaction of cells (e.g., leukocytes) and proteins (e.g., lipoproteins) with the surface of adipose tissue cells. Such processes include, for example, uptake, release, metabolism, and storage of lipids (e.g., triglycerides), cholesterol, lipoproteins, and the like.

M019 exhibits limited sequence similarity with pancreatic proteins, indicating that this protein is involved in physiological processes of the pancreas and in pancreatic disorders, as well as other disorders. Pancreatic disorders in which M019 can be involved include those pancreatic disorders described elsewhere in this disclosure.

Tables A and B summarize sequence data corresponding to the nucleic acids and proteins disclosed herein.

TABLE A

| Protein Designation | SEQ ID NOs | | | Depicted in Figure # | ATCC® Accession # |
|---|---|---|---|---|---|
|  | cDNA | ORF | Protein | | |
| human TANGO 273 | 1 | 2 | 3 | 1 | 207185 |
| murine TANGO 273 | 11 | 12 | 13 | 1 | 207221 |
| human TANGO 325 | 21 | 22 | 23 | 2 | PTA-147 |
| human TANGO 364 | 31 | 32 | 33 | 3 | PTA-425 |
| human TANGO 364 (alternative form) | 41 | 42 | 43 | 3 | PTA-425 |
| human TANGO 405 | 51 | 52 | 53 | 4 | PTA-424 |
| murine TANGO 405 | 61 | 62 | 63 | 4 | |
| murine TANGO 405 (alternative form) | 71 | 72 | 73 | 4 | |
| human M019 | 81 | 82 | 83 | 5 | |

TABLE B

| Protein Desig. | Signal Sequence[1] | | Mature Protein | | Extracellular Domain(s)[2] | | Transmembrane Domain(s) | | Cytoplasmic Domain(s)[2] | |
|---|---|---|---|---|---|---|---|---|---|---|
|  | SEQ ID NOs | | | | | | | | | |
| hum. TANGO 273 | 1 to 22 | 4 | 23 to 172 | 5 | 23 to 60 | 6 | 61 to 81 | 7 | 82 to 172 | 8 |
| mur. TANGO 273 | 1 to 22 | 14 | 23 to 172 | 15 | 23 to 60 | 16 | 61 to 81 | 17 | 82 to 172 | 18 |
| hum. TANGO 325 | 1 to 31 | 24 | 32 to 622 | 25 | 32 to 529 | 26 | 530 to 547 | 27 | 548 to 622 | 28 |
| hum. TANGO 364 | 1 to 31 | 34 | 32 to 510 | 35 | 32 to 345 | 36 | 346 to 370 | 37 | 371 to 510 | 38 |
| hum. TANGO 405 | 1 to 48 | 54 | 49 to 209 | 55 | 49 to 209 | 55 | N/A | | N/A | |
| mur. TANGO 405 | 1 to 52 | 64 | 53 to 178 | 65 | 53 to 178 | 65 | N/A | | N/A | |
| hum. M019 | 1 to 23 | 84 | 24 to 82 | 85 | 24 to 82 | 85 | | | | |
| | | | Amino Acid Residues | | | | | | | |

Notes for Table B:
[1]It is recognized that the carboxyl terminal boundary of the signal sequence can be ±1 or 2 residues from that indicated.
[2]It is recognized that 'extracellular' and cytoplasmic' domains can have the opposite orientation in certain embodiments, as described herein.

Uses of M019 Nucleic Acids, Polypeptides, and Modulators thereof

M019 proteins are involved in disorders which affect both tissues in which they are normally expressed and tissues in which they are normally not expressed. Based on the observation that M019 is expressed in adipose tissue, M019 protein is involved in one or more biological processes which occur in these tissues and in disorders which affect adipose tissue. Such disorder include, for example, obesity, hypercholesterolemia, hyperlipidemia, hyperlipoproteinemia, diabetes, stroke, liver fibrosis, atherosclerosis, arteriosclerosis, and coronary artery disease.

Various aspects of the invention are described in further detail in the following subsections.

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5, 4, 3, 2, 1, 0.5, or 0.1 kilobases of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of all or a portion of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or a complement thereof, or which has a nucleotide sequence comprising one of these sequences, can be isolated using standard molecular biology techniques and the sequence information provided herein. Using all or a portion of the nucleic acid sequences of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, as a hybridization probe, nucleic acid molecules of the invention can be isolated using standard hybridization and cloning techniques (e.g., as described in Sambrook et al., Eds., Molecular Cloning; A Laboratory Manual, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another embodiment, an isolated nucleic acid molecule of the invention comprises a nucleic acid molecule which is a complement of the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425 and PTA-424, or a portion thereof. A nucleic acid molecule which is complementary to a given nucleotide sequence is one which is sufficiently complementary to the given nucleotide sequence that it can hybridize with the given nucleotide sequence thereby forming a stable duplex.

Moreover, a nucleic acid molecule of the invention can comprise a portion of a nucleic acid sequence encoding a full length polypeptide of the invention, such as a fragment which can be used as a probe or primer or a fragment encoding a biologically active portion of a polypeptide of the invention. The nucleotide sequence determined from cloning one gene allows generation of probes and primers designed for identifying and/or cloning homologs in other cell types, e.g., from other tissues, as well as homologs from other mammals. The probe/primer typically comprises substantially purified oligonucleotide. The oligonucleotide typically comprises a region of nucleotide sequence that hybridizes under stringent conditions with at least about 15, preferably about 25, more preferably about 40, 60, 80, 100, 150, 200, 250, 300, 350, 400, 450, 550, 650, 700, 800, 900, 1000, 1200, 1400, 1410, 1600, 1800, 2000, 2200, 2400, 2600, 2800, 3000, or 3500 or more consecutive nucleotides of the sense or anti-sense sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or of a naturally occurring mutant of any of these sequences.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which aberrantly express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of one of SEQ ID NOs: 2, 12, 22, 32, 42, 52, 62, 72, and 82 expressing the encoded portion of the polypeptide protein (e.g., by recombinant expression in vitro), and assessing the activity of the encoded portion of the polypeptide.

The invention further encompasses nucleic acid molecules that differ from the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, due to degeneracy of the genetic code and thus encode the same protein as that encoded by the nucleotide sequence of one of SEQ ID NOs: 2, 12, 22, 32, 42, 52, 62, 72, and 82.

In addition to the nucleotide sequences of one of SEQ ID NOs: 2, 12, 22, 32, 42, 52, 62, 72, and 82, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences (i.e., % identity=# of identical positions/total # of positions {e.g., overlapping positions}×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov.

Another preferred, non-limiting example of a mathematical algorithm utilized for the comparison of sequences is the local homology algorithm of Smith and Waterman (Advances in Applied Mathematics 2: 482–489 (1981)). Such an algorithm is incorporated into the BestFit program, which is part of the Wisconsin™ package, and is used to find the best segment of similarity between two sequences. BestFit reads a scoring matrix that contains values for every possible GCG symbol match. The program uses these values to construct a path matrix that represents the entire surface of comparison with a score at every position for the best possible alignment to that point. The quality score for the best alignment to any point is equal to the sum of the scoring matrix values of the matches in that alignment, less the gap creation penalty multiplied by the number of gaps in that alignment, less the gap extension penalty multiplied by the total length of all gaps in that alignment. The gap creation and gap extension penalties are set by the user. If the best path to any point has a negative value, a zero is put in that position.

After the path matrix is complete, the highest value on the surface of comparison represents the end of the best region of similarity between the sequences. The best path from this highest value backwards to the point where the values revert to zero is the alignment shown by BestFit. This alignment is the best segment of similarity between the two sequences. Further documentation can be found at http://ir.ucdavis.edu/GCGhelp/bestfit.html#algorithm.

Additional algorithms for sequence analysis are known in the art and include ADVANCE and ADAM as described in Torellis and Robotti (1994) Comput. Appl. Biosci., 10:3–5; and FASTA described in Pearson and Lipman (1988) Proc. Natl. Acad. Sci. 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see http://bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, typically exact matches are counted.

As used herein, the phrase "allelic variant" refers to a nucleotide sequence which occurs at a given locus or to a polypeptide encoded by the nucleotide sequence. For example, the TANGO 273 gene exhibits significant homology with a portion of chromosome 7 between chromosomal markers D7S2467 and D7S2552. Allelic variants of any of this gene can be identified by sequencing the corresponding chromosomal portion at the indicated location in multiple individuals.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions. For example, a cDNA encoding a soluble form of a membrane-bound protein of the invention can be isolated based on its hybridization with a nucleic acid molecule encoding all or part of the membrane-bound form. Likewise, a cDNA encoding a membrane-bound form can be isolated based on its hybridization with a nucleic acid molecule encoding all or part of the soluble form.

Accordingly, in another embodiment, an isolated nucleic acid molecule of the invention is at least 15 (25, 40, 60, 80, 100, 150, 200, 250, 300, 350, 400, 450, 500, 600, 700, 800, 900, 1000, 1200, 1400, 1600, 1800, 2000, 2200, 2400, 2600, 2800, 3000, or 3500 or more) nucleotides in length and hybridizes under stringent conditions to the nucleic acid molecule comprising the nucleotide sequence, preferably the coding sequence, of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425, and PTA-424, or a complement thereof. As used herein, the term "hybridizes under stringent conditions" is intended to describe conditions for hybridization and washing under which nucleotide sequences at least 60% (65%, 70%, preferably 75%) identical to each other typically remain hybridized with each other. Such stringent conditions are known to those skilled in the art and can be found in Current Protocols in Molecular Biology, John Wiley & Sons, N.Y. (1989), 6.3.1–6.3.6. A example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147, PTA-425 and PTA-424, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that can exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from any of SEQ ID NOs: 3–8, 13–18, 23–28, 33–38, 43, 53–55, 63–65, 73, and 83–85, yet retain biological activity. In one embodiment, the isolated nucleic acid molecule includes a nucleotide sequence encoding a protein that includes an amino acid sequence that is at least about 40% identical, 50%, 60%, 70%, 80%, 90%, 95%, or 98% identical to the amino acid sequence of any of SEQ ID NOs: 3–8, 13–18, 23–28, 33–38, 43, 53–55, 63–65, 73, and 83–85, or the amino acid sequence encoded by the nucleotide sequence of any of the clones deposited as ATCC® Accession numbers 207185, 207221, PTA-147, PTA-425, and PTA-424.

An isolated nucleic acid molecule encoding a variant protein can be created by introducing one or more nucleotide substitutions, additions or deletions into the nucleotide sequence of any of SEQ ID NOs: 1, 2, 11, 12, 21, 22, 31, 32, 41, 42, 51, 52, 61, 62, 71, 72, 81, 82, and the nucleotide sequence of any of the clones deposited as ATCC® Accession numbers 207185, 207221, PTA-147. PTA-425, and PTA-424, such that one or more amino acid residue substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In one embodiment, a mutant polypeptide that is a variant of a polypeptide of the invention can be assayed for: (1) the ability to form protein:protein interactions with the polypeptide of the invention; (2) the ability to bind a ligand of the polypeptide of the invention; (3) the ability to bind with a modulator or substrate of the polypeptide of the invention; or (4) the ability to modulate a physiological activity of the protein, such as one of those disclosed herein.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' non-translated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind with cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds with DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind with receptors or antigens expressed on a selected cell surface, e.g., by linking the antisense nucleic acid molecules to peptides or antibodies which bind with cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An alpha-anomeric nucleic acid molecule forms specific double-stranded hybrids with complementary RNA in which the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules which are capable of cleaving a single-stranded nucleic acid, such as an mRNA, to which they have a complementary region. Thus, ribozymes (e.g., hammerhead ribozymes as described in Haselhoff and Gerlach (1988) Nature 334:585–591) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the ribozyme active site is complementary to the nucleotide sequence to be cleaved, as described in Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) Science 261: 1411–1418.

The invention includes nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) Anticancer Drug Des. 6(6):569–84; Helene (1992) Ann. N.Y. Acad. Sci. 660:27–36; and Maher (1992) Bioassays 14(12):807–15. "Expression" of a polypeptide, as used herein, refers individually and collectively to the processes of transcription of DNA to generate an RNA transcript and translation of an RNA to generate the polypeptide.

In various embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow specific hybridization with DNA and RNA under conditions of low ionic strength. Synthesis of PNA oligomers can be performed using standard solid phase peptide synthesis protocols such as those described in Hyrup et al. (1996), supra; Perry-O'Keefe et al. (1996) Proc. Natl. Acad. Sci. USA 93: 14670–675.

PNAs can be used in therapeutic and diagnostic applications. For example, PNAs can be used as antisense or anti-gene agents for sequence-specific modulation of gene expression by, e.g., inducing arrest of transcription or translation or by inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) Proc. Natl. Acad. Sci. USA 93: 14670–675).

In another embodiment, PNAs can be modified, e.g., to enhance their stability or cellular uptake, by attaching lipophilic or other helper groups to PNA, by formation of PNA-DNA chimeras, or by use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion provides high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) Nucleic Acids Res. 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) Nucleic Acids Res. 17:5973–88). PNA monomers are then coupled in a step-wise manner to produce a chimeric molecule with a 5' PNA segment and a 3' DNA segment (Finn et al. (1996) Nucleic Acids Res. 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide can include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide can be conjugated with another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to generate antibodies directed against a polypeptide of the invention. In one embodiment, the native polypeptide is isolated from cells or tissue sources by an appropriate purification scheme using standard protein purification techniques. In another embodiment, polypeptides of the invention are produced by recombinant DNA techniques. As an alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals, when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptide regions having an amino acid sequence sufficiently identical to or derived from the amino acid sequence of the protein (e.g., the amino acid sequence shown in any of SEQ ID NOs: 3–8, 13–18, 23–28, 33–38, 43, 53–55, 63–65, 73, and 83–85, or the amino acid sequence encoded by the nucleotide sequence of any of the clones deposited as ATCC® Accession numbers 207185, 207221, PTA-147, PTA-425, and PTA-424), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Examples of polypeptides are those which have the amino acid sequence of any of SEQ ID NOs: 3–8, 13–18, 23–28, 33–38, 43, 53–55, 63–65, 73, and 83–85 or the amino acid sequence encoded by the nucleotide sequence of any of the clones deposited as ATCC® Accession numbers 207185, 207221, PTA-147, PTA-425, and PTA-424. Other useful proteins are substantially identical (e.g., at least about 40%, preferably 50%, 60%, 70%, 80%, 90%, 95%, or 99%) to any of SEQ ID NOs: 3–8, 13–18, 23–28, 33–38, 43, 53–55, 63–65, 73, and 83–85 or the amino acid sequence encoded by the nucleotide sequence of any of the clones deposited as ATCC® Accession numbers 207185, 207221, PTA-147, PTA-425, and PTA-424 and retain the functional activity of the protein of the corresponding naturally-occurring protein. Such proteins can differ in amino acid sequence owing, for example, to natural allelic variation or mutagenesis.

The invention also provides chimeric or fusion proteins. As used herein, a "chimeric protein" or "fusion protein" comprises all or part (preferably biologically active) of a polypeptide of the invention operably linked with a heterologous polypeptide (i.e., a polypeptide other than the same polypeptide of the invention). Within the fusion protein, the term "operably linked" is intended to indicate that the polypeptide of the invention and the heterologous polypeptide are fused in-frame with each other. The heterologous polypeptide can be fused with the amino-terminus or the carboxyl-terminus of the polypeptide of the invention.

One useful fusion protein is a GST fusion protein in which the polypeptide of the invention is fused with the carboxyl terminus of GST sequences. Such fusion proteins can facilitate purification of a recombinant polypeptide of the invention.

In another embodiment, the fusion protein contains a heterologous signal sequence at its amino terminus. For example, the native signal sequence of a polypeptide of the invention can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused with sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands. The immunoglobulin fusion protein can, for example, comprise a portion of a polypeptide of the invention fused with the amino-terminus or the carboxyl-terminus of an immunoglobulin constant region, as disclosed in U.S. Pat. No. 5,714,147, U.S. Pat. No. 5,116,964, U.S. Pat. No. 5,514,582, and U.S. Pat. No. 5,455,165.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be performed using anchor primers which give rise to complementary overhangs between two consecutive gene fragments and which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (e.g., the signal sequence in any of SEQ ID NOs: 3, 13, 23, 33, 43, 53, 63, 73, and 83) can be used to facilitate secretion and isolation of the secreted protein or another protein of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector with a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked with the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, the nucleic acids which flank the signal sequence on its amino-terminal side are likely regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding with a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject, relative to treatment with the naturally occurring form of the protein.

Variants of a protein of the invention which function as either agonists (e.g., mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences can be expressed as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, re-naturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811–7815; Delgrave et al. (1993) Protein Engineering 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 10 (preferably 12, 15, 20, or 30 or more) amino acid residues of the amino acid sequence of any of SEQ ID NOs: 3–8, 13–18, 23–28, 33–38, 43, 53–55, 63–65, 73, and 83–85 or the amino acid sequence encoded by the nucleotide sequence of any of the clones deposited as ATCC® Accession numbers 207185, 207221, PTA-147, PTA-425, and PTA-424, and encompasses an epitope of the protein such that an antibody raised against the peptide forms a specific immune complex with the protein.

Examples of epitopes encompassed by the antigenic peptide are regions that are located on the surface of the protein, e.g., hydrophilic regions. FIGS. 1B, 1C, 2A, 3A, 4A, 4B, and 5A are hydrophobicity plots of proteins of the invention. These plots or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds with a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as papain or pepsin, respectively. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77–96) or trioma techniques. The technology for producing hybridomas is well known (see generally Current Protocols in Immunology (1994) Coligan et al. (Eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SURFZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Cancer Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al. (1994) Bio/technology 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An antibody (or fragment thereof) can be conjugated to a therapeutic moiety such as a cytotoxin, a therapeutic agent, or a radioactive agent (e.g., a radioactive metal ion). Cytotoxins and cytotoxic agents include any agent that is detrimental to cells. Examples of such agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin {formerly designated daunomycin} and doxorubicin), antibiotics (e.g., dactinomycin {formerly designated actinomycin}, bleomycin, mithramycin, and anthramycin), and anti-mitotic agents (e.g., vincristine and vinblastine).

Conjugated antibodies of the invention can be used for modifying a given biological response, the drug moiety not being limited to classical chemical therapeutic agents. For example, the drug moiety can be a protein or polypeptide possessing a desired biological activity. Such proteins include, for example, toxins such as abrin, ricin A, Pseudomonas exotoxin, or diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1, interleukin-2, interleukin-6, granulocyte macrophage colony stimulating factor, granulocyte colony stimulating factor, or other growth factors.

Techniques for conjugating a therapeutic moiety to an antibody are well known (see, e.g., Arnon et al., 1985, "Monoclonal Antibodies For Immunotargeting Of Drugs In Cancer Therapy", in Monoclonal Antibodies And Cancer Therapy, Reisfeld et al., Eds., Alan R. Liss, Inc. pp. 243–256; Hellstrom et al., 1987, "Antibodies For Drug Delivery", in Controlled Drug Delivery, 2nd ed., Robinson et al., Eds., Marcel Dekker, Inc., pp. 623–653; Thorpe, 1985, "Antibody Carriers Of Cytotoxic Agents In Cancer Therapy: A Review", in Monoclonal Antibodies '84: Biological And Clinical Applications, Pinchera et al., Eds., pp. 475–506; "Analysis, Results, And Future Prospective Of The Therapeutic Use Of Radiolabeled Antibody In Cancer Therapy", in Monoclonal Antibodies For Cancer Detection And Therapy, Baldwin et al., Eds., Academic Press, pp. 303–316, 1985; and Thorpe et al., 1982, Immunol. Rev., 62:119–158). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, including expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, designated expression vectors, are capable of directing expression of genes with which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked with the nucleic acid sequence to be expressed. Within a recombinant expression vector, "operably linked" is intended to mean that the nucleotide sequence of interest is linked with the regulatory sequence(s) in a manner which allows expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, and the level of expression of protein desired. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., E. coli) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174 (DE3) from a resident lambda prophage harboring a T7 gn1 gene under the transcriptional control of the lacUV 5 promoter.

One strategy to maximize recombinant protein expression in E. coli is to express the protein in a host bacteria having an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector such that the individual codons for each amino acid are those preferentially used in E. coli (Wada et al. (1992) Nucleic Acids Res. 20:2111–2118). Such alteration of nucleic acid sequences of the invention can be performed by standard DNA synthesis techniques.

In another embodiment, the expression vector is a yeast expression vector. Examples of vectors for expression in yeast S. cerevisiae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187–195). When used in mammalian cells, the expression vector's control functions are often provided by viral regulatory elements. For example, commonly used promoters are derived from polyoma, adenovirus 2, cytomegalovirus and simian virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the alpha-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operably linked with a regulatory sequence in a manner which allows for expression (by transcription of the DNA molecule) of an RNA molecule which is antisense, relative to the mRNA encoding a polypeptide of the invention. Regulatory sequences operably linked with a nucleic acid cloned in the antisense orientation can be selected which direct continuous expression of the antisense RNA molecule in a variety of cell types, for instance viral promoters and/or enhancers, or regulatory sequences can be selected which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, and electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells integrate the foreign DNA into their genome. In order to identify and select these integrants, a gene that encodes a selectable marker (e.g., for resistance to antibiotics) can be introduced into the host cells along with the gene of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene survive, while other cells die).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can be used to produce non-human transgenic animals. For example, in one embodiment, a host cell of the invention is a fertilized oocyte or an embryonic stem cell into which a sequences encoding a polypeptide of the invention have been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a polypeptide of the invention (or a homologue thereof) into the male pronuclei of a fertilized oocyte (e.g., by microinjection or retroviral infection) and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked with the transgene to direct expression of a polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can be used to breed additional animals carrying the transgene. Moreover, transgenic animals harboring the transgene can further be bred to other transgenic animals harboring other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In one embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered, but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Numbers WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can be produced according to the methods described in Wilmut et al. (1997) Nature 385:810–813 and PCT Publication Numbers WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity can, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents and protein or polypeptide agents depends upon a number of factors within the ken of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Examples of doses of a small molecule include milligram or microgram amounts per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). Examples of doses of a protein or polypeptide include gram, milligram or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). For antibodies, examples of dosages are from about 0.1 milligram per kilogram to 100 milligrams per kilogram of body weight (generally 10 milligrams per kilogram to 20 milligrams per kilogram). If the antibody is to act in the brain, a dosage of 50 milligrams per kilogram to 100 milligrams per kilogram is usually appropriate. It is furthermore understood that appropriate doses of one of these agents depend upon the potency of the agent with respect to the expression or activity to be modulated. Such appropriate doses can be determined using the assays described herein. When one or more of these agents is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates; and agents for the adjustment of tonicity such as sodium chloride or dextrose. pH can be adjusted using acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). The composition should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and anti-fungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, examples of methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, adjuvant materials, or both, can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

It is recognized that the pharmaceutical compositions and methods described herein can be used independently or in combination with one another. That is, subjects can be administered one or more of the pharmaceutical compositions, e.g., pharmaceutical compositions comprising a nucleic acid molecule or protein of the invention or a modulator thereof, subjected to one or more of the therapeutic methods described herein, or both, in temporally overlapping or non-overlapping regimens. When therapies overlap temporally, the therapies may generally occur in any order and can be simultaneous (e.g., administered simultaneously together in a composite composition or simultaneously but as separate compositions) or interspersed. By way of example, a subject afflicted with a disorder described herein can be simultaneously or sequentially administered both a cytotoxic agent which selectively kills aberrant cells and an antibody (e.g., an antibody of the invention) which can, in one embodiment, be conjugated or linked with a therapeutic agent, a cytotoxic agent, an imaging agent, or the like.

The pharmaceutical compositions can be included in a container, pack, or dispenser together with instructions for administration.

V. Uses and Methods of the Invention

The nucleic acid molecules, proteins, protein homologs, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used for all of the purposes identified herein in portions of the disclosure relating to individual types of protein of the invention. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind with a polypeptide of the invention or have a stimulatory or inhibitory effect on, for example, expression or activity of a polypeptide of the invention.

In one embodiment, the invention provides assays for screening candidate or test compounds which bind with or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam (1997) Anticancer Drug Des. 12:145).

Examples of methods useful for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds can be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or phage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind with the polypeptide is determined. The cell, for example, can be a yeast cell or a cell of mammalian origin. Determining the ability of the test compound to bind with the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind with the polypeptide or a biologically active portion thereof as compared to the known compound.

In another embodiment, the assay involves assessment of an activity characteristic of the polypeptide, wherein binding of the test compound with the polypeptide or a biologically active portion thereof alters (i.e., increases or decreases) the activity of the polypeptide.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide to bind with or interact with a target molecule or to transport molecules across the cytoplasmic membrane.

Determining the ability of a polypeptide of the invention to bind with or interact with a target molecule can be accomplished by one of the methods described above for determining direct binding. As used herein, a "target molecule" is a molecule with which a selected polypeptide (e.g., a polypeptide of the invention binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates association of downstream signaling molecules with a polypeptide of the invention. Determining the ability of a polypeptide of the invention to bind with or interact with a target molecule can be accomplished by determining the activity of the target molecule. For example, the activity of the target molecule can be determined by detecting induction of a cellular second messenger of the target (e.g., an mRNA, intracellular $Ca^{2+}$, diacylglycerol, IP3, and the like), detecting catalytic/enzymatic activity of the target on an appropriate substrate, detecting induction of a reporter gene (e.g., a regulatory element that is responsive to a polypeptide of the invention operably linked with a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind with the polypeptide or biologically active portion thereof. Binding of the test compound with the polypeptide can be determined either directly or indirectly as described above. In one embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind with the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate activity of the polypeptide can be accomplished, for example, by determining the ability of the polypeptide to bind with a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic activity, the enzymatic activity, or both, of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide. Ability of the test compound to interact with the polypeptide can be determined by assessing the ability of the polypeptide to preferentially bind with or modulate the activity of a target molecule, or by any other method.

The cell-free assays of the present invention are amenable to use of either soluble or membrane-bound forms (where applicable) of a polypeptide of the invention. In the case of cell-free assays comprising a membrane-bound form of the polypeptide, it can be desirable to use a solubilizing agent in order to maintain the membrane-bound form of the polypeptide in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, isotridecypoly(ethylene glycol ether)n, 3-{(3-cholamidopropyl)dimethylamminio}-1-propane sulfonate (CHAPS), 3-{(3-cholamidopropyl)dimethylamminio}-2-hydroxy-1-propane sulfonate (CHAPSO), or N-dodecyl-N,N-dimethyl-3-ammonio-1-propane sulfonate.

In one or more embodiments of the above assay methods of the present invention, it can be desirable to immobilize either the polypeptide of the invention or its target molecule in order to facilitate separation of complexed and non-complexed forms of one or both of the molecules, as well as to accommodate automation of the assay. Binding of a test compound with the polypeptide, or interaction of the polypeptide with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione Sepharose™ beads (Sigma Chemical; St. Louis, Mo.) or glutathione-derivatized microtiter plates, which are combined with the test compound and either the non-adsorbed target protein or a polypeptide of the invention. The combination is incubated under conditions conducive to complex formation (e.g., at physiological conditions for salt and pH). Following incubation, the beads or microtiter plate wells are washed to remove unbound components, and complex formation is measured directly or indirectly, for example, as described above. Alternatively, the complexes can be dissociated from the matrix, and the level of binding or activity of the polypeptide of the invention can be determined using standard techniques, such as those described herein.

Other techniques for immobilizing proteins on matrices can also be used in the screening assays of the invention. For example, either the polypeptide of the invention or a target molecule thereof (e.g., a protein which binds therewith or a substrate or an analog of a substrate of the protein of the invention) can be immobilized using conjugation of biotin and streptavidin. Biotinylated polypeptide of the invention or target molecules can be prepared using biotin-NHS (biotin-N-hydroxy-succinimide) using techniques well known in the art (e.g., using a commercially available kit such as the biotinylation kit manufactured by Pierce Chemical Co.; Rockford, Ill.), and immobilized in the wells of streptavidin-coated 96-well plates (Pierce Chemical). Alternatively, antibodies which are reactive with the polypeptide of the invention or target molecules but which do not interfere with binding of the polypeptide of the invention with its target molecule can be derivatized to the wells of the plate, and unbound target or polypeptide of the invention can be trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and expression of the selected mRNA or protein (i.e., mRNA or protein corresponding to a polypeptide or nucleic acid of the invention) in the cell is determined. The level of expression of the selected mRNA or protein in the presence of the candidate compound is compared with the level of expression of the selected mRNA or protein in the absence of the candidate compound. The candidate compound can then be identified as a modulator of expression of the polypeptide of the invention based on this comparison. For example, if expression of the selected mRNA or protein is greater (i.e., statistically significantly greater) in the presence of the candidate compound than in its absence, then the candidate compound is identified as a stimulator of expression of the selected mRNA or protein. Alternatively, if expression of the selected mRNA or protein is less (i.e., statistically significantly less) in the presence of the candidate compound than in its absence, then the candidate compound is identified as an inhibitor of expression of the selected mRNA or protein. The level of the selected mRNA or protein expression in the cells can be determined by methods described herein.

In yet another aspect of the invention, a polypeptide of the invention can be used as a "bait protein" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins which bind with or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. Mapping of sequences to chromosomes is an important first step in correlating these sequences with genes associated with occurrence of disease. For example, the TANGO 273 gene exhibits significant homology with a portion of chromosome 7 between chromosomal markers D7S2467 and D7S2552.

Briefly, genes can be mapped to chromosomes by preparing PCR primers (preferably 15–25 nucleotide residues in length) from the sequence of a gene of the invention. Computer analysis of the sequence of a gene of the invention can be used to rapidly select primers that do not span more than one exon in the genomic DNA, which would complicate the amplification process. These primers can be used for PCR screening of somatic cell hybrids containing individual human chromosomes. Only those hybrids containing the human gene corresponding to the gene sequences will yield an amplified fragment. For a review of this technique, see D'Eustachio et al. ((1983) Science 220:919–924).

PCR mapping of somatic cell hybrids is a rapid procedure for assigning a particular sequence to a particular chromosome. Three or more sequences can be assigned per day using a single thermal cycler. Using one or more nucleic acid sequences of the invention to design oligonucleotide primers, sub-localization can be achieved using panels of fragments prepared from specific chromosomes. Other mapping strategies which can similarly be used to map a gene to its chromosomal location include in situ hybridization (described in Fan et al. (1990) Proc. Natl. Acad. Sci. USA 87:6223–27), pre-screening with labeled flow-sorted chromosomes, and pre-selection by hybridization with chromosome specific cDNA libraries. Fluorescence in situ hybridization (FISH) of a DNA sequence using a metaphase chromosomal spread can be used to provide a precise chromosomal location in one step. For a review of this technique, see Verma et al. (Human Chromosomes: A Manual of Basic Techniques (Pergamon Press, New York, 1988)).

Reagents for chromosome mapping can be used individually to mark a single chromosome or a single site on a chromosome. Alternatively, panels of reagents can be used for marking multiple sites, multiple chromosomes, or both. Reagents corresponding to non-coding regions of the genes actually are preferred for mapping purposes. Coding sequences are more likely to be conserved within gene families, thus increasing the chance of cross-hybridization during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified by linkage analysis (co-inheritance of physically adjacent genes), described in, e.g., Egeland et al. (1987) Nature 325:783–787.

Moreover, differences in the DNA sequences between individuals affected and non-affected with a disease associated with a gene of the invention can be determined. If a mutation is observed in some or all of the affected individuals, but not in any (or in very few) non-affected individuals, then the mutation is likely to be the causative agent of the particular disease. Comparison of affected and non-affected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of physical identification devices such as general issue "dog tags," which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. The nucleic acid sequences described herein can be used to prepare two PCR primers from the 5' and 3' ends of the sequences. These primers can then be used to amplify an individual's DNA and to subsequently sequence it.

Panels of corresponding DNA sequences from individuals, prepared in this manner, can provide unique individual identifications, because (with the exception of identical twins) every individual has a unique set of such DNA sequences owing, at least in part, to allelic differences. Sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the non-coding regions. It is estimated that allelic variation between individual humans occurs with a frequency of about once per 500 nucleotide residues. Each of the sequences described herein can, to some degree, be used as a standard against which DNA from an individual can be compared for identification purposes. Because greater numbers of polymorphisms occur in the non-coding regions, fewer non-coding sequences are necessary to differentiate individuals. The non-coding sequences of any of SEQ ID NOs: 1, 11, 21, 31, 41, 51, 61, 71, and 81 can comfortably provide positive individual identification with a panel of perhaps 10 to 1,000 primers which each yield a non-coding amplified sequence of 100 bases. If predicted coding sequences, such as those in any of SEQ ID NOs: 2, 12, 22, 32, 42, 52, 62, 72, and 82 are used, a more appropriate number of primers for positive individual identification would be 500–2,000.

If a panel of reagents from the nucleic acid sequences described herein is used to generate a unique identification database for an individual, those same reagents can later be used to identify nucleic acids, cells, or tissue from that individual. Using the unique identification database, positive identification of the individual, living or dead, can be made from extremely small samples.

3. Use of Partial Gene Sequences in Forensic Biology

DNA-based identification techniques can be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues (e.g., hair or skin) or body fluids (e.g., blood, saliva, or semen) found at a crime scene. The amplified sequence can be compared with a standard, thereby allowing identification of the origin of the biological sample.

The sequences of the present invention can be used to provide polynucleotide reagents (e.g., PCR primers) targeted to specific loci in the human genome, which can enhance the reliability of DNA-based forensic identifications by, for example, providing another "identification marker" (i.e., another DNA sequence that is unique to a particular individual). As mentioned above, actual nucleotide sequence information can be used for identification as an accurate alternative to patterns formed by restriction enzyme-generated fragments. Sequences of non-coding regions are particularly appropriate for this use, because greater numbers of polymorphisms occur in non-coding regions, making it easier to differentiate individuals using this technique. Examples of polynucleotide reagents include the nucleic acid sequences of the invention or portions thereof, e.g., fragments derived from non-coding regions having a length of at least 20 or 30 nucleotide residues.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining expression of a gene encoding a polypeptide of the invention as well as activity of a polypeptide of the invention, in the context of a biological sample (e.g., blood, serum, cells, tissue) to thereby determine whether an individual is afflicted with a disease or disorder, or is at risk of developing a disorder, associated with aberrant or unwanted expression of a gene encoding a polypeptide of the invention or aberrant or unwanted activity of a polypeptide of the invention. The invention also provides for prognostic (or predictive) assays for determining whether an individual is at risk of developing a disorder associated with a protein of the invention, with expression of a nucleic acid encoding a polypeptide of the invention, or with activity of a polypeptide of the invention. For example, mutations in a gene encoding a polypeptide of the invention can be assayed in a biological sample. Such assays can be used for prognostic or predictive purpose to thereby prophylactically treat an individual prior to the onset of a disorder characterized by or associated with a polypeptide of the invention, expression of a nucleic acid encoding it, or its activity.

As an alternative to making determinations based on the absolute expression level of selected genes, determinations may be based on the normalized expression levels of these genes. Expression levels are normalized by correcting the absolute expression level of a gene encoding a polypeptide of the invention by comparing its expression to the expression of a different gene, e.g., a housekeeping gene that is constitutively expressed. Suitable genes for normalization include housekeeping genes such as the actin gene. This normalization allows the comparison of the expression level in one sample (e.g., a patient sample), to another sample, or between samples from different sources.

Alternatively, the expression level can be provided as a relative expression level. To determine a relative expression level of a gene, the level of expression of the gene is determined for 10 or more samples of different endothelial (e.g., intestinal endothelium, airway endothelium, or other mucosal epithelium) cell isolates, preferably 50 or more samples, prior to the determination of the expression level for the sample in question. The mean expression level of each of the genes assayed in the larger number of samples is determined and this is used as a baseline expression level for the gene(s) in question. The expression level of the gene determined for the test sample (absolute level of expression) is then divided by the mean expression value obtained for that gene. This provides a relative expression level and aids in identifying extreme cases of disorders associated with aberrant expression of a gene encoding a polypeptide of the invention protein or with aberrant expression of a ligand thereof.

Preferably, the samples used in the baseline determination will be from either or both of cells which aberrantly express a gene encoding a polypeptide of the invention or a ligand thereof (i.e. 'diseased cells') and cells which express a gene encoding a polypeptide of the invention at a normal level or a ligand thereof (i.e. 'normal' cells). The choice of the cell source is dependent on the use of the relative expression level. Using expression found in normal tissues as a mean expression score aids in validating whether aberrance in expression of a gene encoding a polypeptide of the invention occurs specifically in diseased cells. Such a use is particularly important in identifying whether a gene encoding a polypeptide of the invention can serve as a target gene. In addition, as more data is accumulated, the mean expression value can be revised, providing improved relative expression values based on accumulated data. Expression data from endothelial cells (e.g., mucosal endothelial cells) provides a means for grading the severity of the disorder.

Another aspect of the invention pertains to monitoring the influence of agents (e.g., drugs, antibodies, antisense oligonucleotides, or other compounds) on the expression or activity of a polypeptide of the invention in clinical trials.

These and other agents are described in further detail in the following sections.

1. Diagnostic Assays

An example of a method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention. An example of an agent for detecting mRNA or genomic DNA encoding a polypeptide of the invention is a labeled nucleic acid probe capable of hybridizing with mRNA or genomic DNA encoding a polypeptide of the invention. The nucleic acid probe can be, for example, a full-length cDNA, such as the nucleic acid of one of SEQ ID NOs: 1, 11, 21, 31, 41, 51, 61, 71, and 81, or a portion thereof, such as an oligonucleotide of at least 15, 30, 50, 100, 250 or 500 nucleotides in length and sufficient to specifically hybridize under stringent conditions with a mRNA or genomic DNA encoding a polypeptide of the invention. Other suitable probes for use in the diagnostic assays of the invention are described herein.

An example of an agent for detecting a polypeptide of the invention is an antibody capable of binding with a polypeptide of the invention, such as an antibody having a detectable label. Antibodies can be polyclonal or, preferably, monoclonal. An intact antibody, or a fragment thereof (e.g., Fab or F(ab')$_2$) can be used. The term "labeled," with regard to the probe or antibody, includes direct labeling of the probe or antibody by coupling (i.e., physically linking) a detectable substance to the probe or antibody, as well as indirect labeling of the probe or antibody by coupling it with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect mRNA, protein, or genomic DNA in a biological sample in vitro as well as in vivo. For example, in vitro techniques for detection of mRNA include Northern hybridization methods and in situ hybridization methods. In vitro techniques for detection of a polypeptide of the invention include enzyme linked immunosorbent assays (ELISAs), Western blots, immunoprecipitation, and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker, the presence and location of which in a subject can be detected using standard imaging techniques.

In one embodiment, the biological sample contains protein molecules obtained from the test subject. Alternatively, the biological sample can contain mRNA molecules obtained from the test subject or genomic DNA molecules obtained from the test subject. An example of a biological sample is a peripheral blood leukocyte-containing sample obtained by conventional means from a subject (e.g., isolated peripheral blood leukocytes).

In another embodiment, the methods further involve obtaining a control biological sample from a control (i.e., non-afflicted) subject, contacting the control sample with a compound or agent capable of detecting a polypeptide of the invention or mRNA or genomic DNA encoding a polypeptide of the invention. The presence or amount of the polypeptide, mRNA, or genomic DNA encoding the polypeptide in the control and test samples can be compared to assess the degree, if any, to which the presence or amount in the test sample differs from that in the control sample.

The invention also encompasses kits for detecting the presence of a polypeptide or nucleic acid of the invention in a biological sample obtained from a subject. Such kits can be used to determine if a subject is suffering from or is at increased risk of developing a disorder associated with aberrant expression of a polypeptide of the invention (e.g., one of the disorders described in the section of this disclosure wherein the individual polypeptide of the invention is discussed). For example, the kit can comprise a labeled compound or agent capable of detecting the polypeptide or mRNA encoding the polypeptide in a biological sample. The kit can also, or alternatively, contain means for determining the amount of the polypeptide or mRNA in the sample (e.g., an antibody which specifically binds with the polypeptide or an oligonucleotide probe which binds with a nucleic acid encoding the polypeptide). Kits can include instructions for assessing whether the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which specifically binds with a polypeptide of the invention; and, optionally, (2) a second, different antibody which specifically binds with either the polypeptide or the first antibody and is conjugated with a detectable agent.

For oligonucleotide-based kits, the kit can comprise, for example: (1) an oligonucleotide (e.g., a detectably labeled oligonucleotide) which hybridizes with a nucleic acid encoding a polypeptide of the invention or (2) a pair of primers useful for amplifying a nucleic acid encoding a polypeptide of the invention. The kit can comprise, for example, a buffering agent, a preservative, or a protein stabilizing agent. The kit can also comprise components necessary for detecting the detectable agent (e.g., an enzyme or a substrate). The kit can contain a control sample or a series of control samples which can be assayed and compared with the test sample assay results. Each component of the kit can be enclosed within an individual container and all of the various containers can furthermore be within a single package, optionally with instructions for assessing whether the tested subject is suffering from or is at risk of developing a disorder associated with aberrant expression of the polypeptide.

2. Prognostic Assays

The methods described herein can furthermore be used as diagnostic or prognostic assays to identify subjects having or at risk of developing a disease or disorder associated with aberrant expression or activity of a polypeptide of the invention (e.g., one of the disorders described in the section of this disclosure wherein the individual polypeptide of the invention is discussed). Thus, the present invention provides a method in which a test sample is obtained from a subject and a polypeptide or nucleic acid (e.g., mRNA, genomic DNA) of the invention is detected, wherein the presence, level, or activity of the polypeptide or nucleic acid in the sample is associated with an enhanced or diminished risk of developing a disease or disorder associated with aberrant expression or activity of the polypeptide.

Furthermore, the prognostic assays described herein can be used to determine whether an agent (e.g., an agonist, antagonist, peptidomimetic, protein, peptide, nucleic acid, small molecule, or other drug candidate) can be administered to a subject in order to treat a disease or disorder associated with aberrant expression or activity of a polypeptide of the invention. For example, such methods can be used to determine whether a subject can be effectively treated using a specific agent or class of agents (e.g., agents of a type which decrease activity of the polypeptide). Thus, the present invention provides methods for determining whether an agent can be administered to a subject in order to effectively treat a disorder associated with aberrant expression or activity of a polypeptide of the invention. When efficacious agents are known or found, such assays can also be used to estimate tan efficacious dose of the agent.

The methods of the invention can be used to detect genetic lesions or mutations in a gene of the invention in order to assess if a subject having the lesioned or mutated gene is at risk for a disorder characterized aberrant expression or activity of a polypeptide of the invention. In certain embodiments, the methods include detecting, in a sample of cells obtained from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) a non-wild type splicing pattern of a messenger RNA transcript of the gene; 8) a non-wild type level of the protein encoded by the gene; 9) an allelic loss of the gene; and 10) an inappropriate post-translational modification of the protein encoded by the gene. As described herein, there are a large number of assay techniques known in the art which can be used for detecting such lesions and mutations in a gene.

In certain embodiments, detection of the lesion involves the use of an oligonucleotide primer in a polymerase chain reaction (PCR; see, e.g., U.S. Pat. Nos. 4,683,195 and 4,683,202), such as anchor PCR or RACE PCR, or, alternatively, in a ligation chain reaction (LCR; see, e.g., Landegran et al. (1988) Science 241:1077–1080; and Nakazawa et al. (1994) Proc. Natl. Acad. Sci. USA 91:360–364), the latter of which can be particularly useful for detecting point mutations in a gene (see, e.g., Abravaya et al. (1995) Nucleic Acids Res. 23:675–682). This method can include the steps of collecting a sample of cells from a patient, isolating nucleic acid (e.g., genomic, mRNA, or both) from the cells of the sample, contacting the nucleic acid sample with one or more primers which specifically hybridize with the selected gene under conditions such that hybridization and amplification of the gene (if present) occurs, and detecting the presence or absence of an amplification product. The method can also include detecting the size of the amplification product and comparing the length to the length of a corresponding product obtained in the same manner from a control sample. PCR, LCR, or both can be used as a preliminary amplification step in conjunction with any of the techniques used for detecting mutations described herein.

Alternative amplification methods include: self-sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using any of a variety of techniques well known to those of skill in the art. These detection schemes are especially useful for detection of nucleic acid molecules if such molecules are present in very low numbers.

In an alternative embodiment, mutations in a selected gene can be identified in a sample by detecting alterations in restriction enzyme cleavage patterns. For example, sample and control DNA is isolated, (optionally) amplified, digested with one or more restriction endonucleases, and fragment length sizes are determined by gel electrophoresis and compared. Differences in fragment length sizes between sample and control DNA indicates occurrence of mutations or other sequence differences in the sample DNA. Moreover, sequence specific ribozymes (see, e.g., U.S. Pat. No. 5,498,531) can be used to score for the presence of specific mutations by development or loss of a ribozyme cleavage site.

In other embodiments, genetic mutations are identified by hybridizing a sample and control nucleic acids, e.g., DNA or RNA, with high density arrays containing hundreds or thousands of oligonucleotides probes (Cronin et al. (1996) Human Mutation 7:244–255; Kozal et al. (1996) Nature Medicine 2:753–759). For example, genetic mutations can be identified using two-dimensional arrays of light-generated DNA probes fixed to a surface, as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by hybridization of the nucleic acid sample with a second hybridization array in order to characterize specific mutations using smaller, specialized probe arrays complementary to many or all potential variants or mutations. Each mutation array is composed of parallel probe sets, one complementary to the wild-type gene and the other complementary to the mutant gene.

In yet another embodiment, any of a variety of sequencing methods known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be used when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in a selected gene include methods in which protection from cleavage agents is used to detect mismatched bases in RNA/RNA or RNA/DNA heteroduplexes (Myers et al. (1985) Science 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent that cleaves single-stranded regions of the duplex such as those which exist due to base pair mismatches between the control and sample strands. RNA/DNA duplexes can be treated with RNase to digest mismatched regions, and DNA/DNA hybrids can be treated with S1 nuclease to digest mismatched regions.

In other embodiments, DNA/DNA or RNA/DNA duplexes can be treated with hydroxylamine or osmium tetroxide and with piperidine in order to digest mismatched regions. After digestion of the mismatched regions, the resulting material is separated by size on denaturing polyacrylamide gels to determine the site of the mutated or mismatched region. See, e.g., Cotton et al. (1988) Proc. Natl. Acad. Sci. USA 85:4397; Saleeba et al. (1992) Methods Enzymol. 217:286–295. In one embodiment, the control DNA or RNA is labeled for detection.

In still another embodiment, the mismatch cleavage reaction employs one or more proteins that recognize mismatched base pairs in double-stranded DNA (so called DNA mismatch repair enzymes) in defined systems for detecting and mapping point mutations in cDNAs obtained from samples of cells. For example, the mutY enzyme of *E. coli* cleaves following A residues at G/A mismatches and the thymidine DNA glycosylase from HeLa cells cleaves following T residues at G/T mismatches (Hsu et al. (1994) Carcinogenesis 15:1657–1662). According to one embodiment, a probe based on a selected sequence, e.g., a wild-type sequence, is hybridized with a cDNA or other DNA product obtained from a test cell(s). The duplex is treated with a DNA mismatch repair enzyme, and the cleavage products, if any, are detected using an electrophoresis protocol or another polynucleotide-separating method. See, e.g., U.S. Pat. No. 5,459,039.

In other embodiments, alterations in electrophoretic mobility are used to identify mutations in genes. For example, single strand conformation polymorphism (SSCP) analysis can be used to detect differences in electrophoretic mobility between mutant and wild type nucleic acids (Orita et al. (1989) Proc. Natl. Acad. Sci. USA 86:2766; see also Cotton (1993) Mutat. Res. 285:125–144; Hayashi (1992) Genet. Anal. Tech. Appl. 9:73–79). Single-stranded DNA fragments of sample and control nucleic acids are denatured and allowed to re-nature. The secondary structure of single-stranded nucleic acids varies according to their nucleotide sequence, and the resulting alteration in electrophoretic mobility enables detection of even a single base change. The DNA fragments can be labeled or detected using labeled probes. The sensitivity of the assay can be enhanced by using RNA (rather than DNA), because the secondary structure of RNA is more sensitive to sequence changes. In one embodiment, the method uses heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE), as described (Myers et al. (1985) Nature 313:495). When DGGE is used as the method of analysis, DNA is modified to ensure that it does not completely denature, for example by adding a 'GC clamp' of approximately 40 nucleotide residues of high-melting GC-rich DNA to one or both ends of the DNA strands, for example using a PCR method. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, and selective primer extension. For example, oligonucleotide primers can be prepared in which the known mutation is located centrally. The primers are hybridized with target DNA under conditions which permit hybridization only if a perfect complementary nucleotide sequence match occurs (Saiki et al. (1986) Nature 324:163); Saiki et al. (1989) Proc. Natl. Acad. Sci. USA 86:6230). Such allele specific oligonucleotides are hybridized with PCR-amplified target DNA or attached to a surface for hybridization.

Alternatively, allele specific amplification technology can be used in conjunction with the methods of the invention. Oligonucleotides used as primers for specific amplification have a sequence complementary to the nucleotide sequence of a mutation of interest in the center of the molecule, so that occurrence of amplification depends on occurrence of the mutation in the sample nucleic acid (Gibbs et al. (1989) Nucleic Acids Res. 17:2437–2448) or at the extreme 3' end of one primer where, under appropriate conditions, mismatching can prevent or inhibit polymerase extension (Prossner (1993) Tibtech 11:238). In addition, it can be desirable to introduce a novel restriction site in the region of the mutation in order to facilitate cleavage-based detection (Gasparini et al. (1992) Mol. Cell Probes 6:1). Amplification can be performed using Taq ligase (Barany (1991) Proc. Natl. Acad. Sci. USA 88:189). In such cases, ligation will occur only if there is a perfect match at the $_3$' end of the 5' sequence, thereby making it possible to assess the presence of a known mutation at a specific site by looking for the presence or absence of amplification.

The methods described herein can be performed, for example, using pre-packaged diagnostic kits comprising at least one probe nucleic acid or antibody reagent described herein. Such kits can be used, for example, in clinical settings to diagnose patients exhibiting symptoms or a family history of a disorder involving a gene encoding a polypeptide of the invention. Furthermore, any cell type or tissue in which the polypeptide of the invention is expressed (e.g., a blood sample containing peripheral blood leukocytes for proteins which are secreted or which occur on or in peripheral blood leukocytes) can be used in the prognostic assays described herein.

3. Pharmacogenomics

Agents which have a stimulatory or inhibitory effect on activity or expression of a polypeptide of the invention, as identified by a screening assay described herein for example, can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual can be considered. Differences in metabolism of therapeutics can lead to severe toxicity or therapeutic failure by altering the relation between dose and blood concentration of the pharmacologically active drug. Thus, the pharmacogenomics of the individual permits selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to facilitate selection of one or more appropriate agents for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism." These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 {NAT 2} and cytochrome P450 enzymes CYP2D6 and CYP2C19) explains why some patients do not obtain the expected drug effects or exhibit exaggerated drug response and serious toxicity following administration of standard and safe doses of a drug. These polymorphisms are expressed in two phenotypes in the population, the extensive metabolizer (EM) and poor metabolizer (PM). The prevalence of PM is different among different populations. For example, the gene encoding CYP2D6 is highly polymorphic, and several mutations have been identified in PM. Each of these mutations results in absence of functional CYP2D6. Poor metabolizers of CYP2D6 and CYP2C19 frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, activity of a polypeptide of the invention, expression of a nucleic acid encoding the polypeptide, or mutation content of a gene encoding the polypeptide in an individual can be determined to facilitate selection of appropriate agents for therapeutic or prophylactic treatment of the individual. In addition, pharmacogenetic studies can be used to apply genotyping of polymorphic alleles encoding drug-metabolizing enzymes to identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the screening assays described herein.

4. Monitoring of Effects During Clinical Trials

Monitoring the influence of agents (e.g., drug compounds) on expression or activity of a polypeptide of the invention (e.g., ability to modulate aberrant cell proliferation chemotaxis, differentiation, or both) can be applied not only in basic drug screening, but also in clinical trials. For example, the effectiveness of an agent, as determined by a screening assay as described herein, to increase gene expression, protein levels, or protein activity can be monitored in clinical trials of subjects exhibiting decreased gene expression, protein levels, or protein activity. Alternatively, the effectiveness of an agent, as determined by a screening assay, to decrease gene expression, protein levels, or protein activity can be monitored in clinical trials of subjects exhibiting increased gene expression, protein levels, or protein activity. In such clinical trials, expression or activity of a polypeptide of the invention and, optionally, that of other polypeptide that have been implicated in similar disorders, can be used as a marker of the immune responsiveness of a particular cell.

For example, genes (including those of the invention) that are modulated in cells by treatment with an agent (e.g., a peptide, a drug, or another small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and their RNA can be prepared and analyzed to determine the level of expression of one or more genes of the invention and, optionally, other genes implicated in the disorder. The levels of gene expression (i.e., a gene expression pattern) can be quantified by Northern blot analysis or by RT-PCR, as described herein, or by assessing the amount of protein produced, by one of the methods as described herein, or by measuring the level of activity of a gene of the invention or other gene(s). In this way, the gene expression pattern can serve as an indicator of the physiological response of the cells to the agent. Accordingly, this response state can be determined before, and at various points during, or after treatment of the individual with the agent (or, of course, at more than one of these stages).

In one embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising (i) obtaining a pre-administration sample from a subject prior to administration of the agent; (ii) detecting the level of the polypeptide or nucleic acid of the invention in the pre-administration sample; (iii) obtaining one or more post-administration samples from the subject; (iv) detecting the level the of the polypeptide or nucleic acid of the invention in the post-administration sample(s); (v) comparing the level of the polypeptide or nucleic acid of the invention in the pre-administration sample with the level of the polypeptide or nucleic acid of the invention in the post-administration sample(s); and (vi) altering the administration of the agent to the subject accordingly. For example, increased administration of the agent can be desirable to increase the expression or activity of the polypeptide to levels higher than those detected, i.e., to increase the effectiveness of the agent. Alternatively, decreased administration of the agent can be desirable to decrease expression or activity of the polypeptide to levels lower than those detected, i.e., to decrease the effectiveness of the agent.

C. Methods of Treatment

The present invention provides both prophylactic and therapeutic methods of treating a subject afflicted with, at risk for developing, or susceptible to a disorder associated with aberrant expression or activity of a polypeptide of the invention. Such disorders are described elsewhere in this disclosure.

1. Prophylactic Methods

In one aspect, the invention provides a method for preventing in a subject, a disorder associated with aberrant expression or activity of a polypeptide of the invention, by administering to the subject an agent which modulates expression of the polypeptide or at least one activity of the polypeptide. Subjects at risk for a disease which is caused or contributed to by aberrant expression or activity of a polypeptide of the invention can be identified by, for example, any one or combination of the diagnostic and prognostic assays described herein. Administration of a prophylactic agent can occur prior to the manifestation of symptoms characteristic of the aberrance, so that the disease or disorder is prevented or, alternatively, delayed in its onset or progression. Depending on the type of aberrance, for example, an agonist or antagonist agent can be used for treating the subject. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid, or a protein, a naturally-occurring cognate ligand of the polypeptide, a peptide, a peptidomimetic, or a small molecule. In one embodiment, the agent stimulates one or more of the biological activities of the polypeptide. Examples of such stimulatory agents include a polypeptide of the invention, a biologically active portion of such a polypeptide, a portion of such a polypeptide which comprises an epitope of the native polypeptide, and a nucleic acid molecule encoding the polypeptide of the invention that has been introduced into the cell. In another embodiment, the agent inhibits a biological activity of the polypeptide of the invention or expression of a protein or nucleic acid of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., up-regulates or down-regulates) expression or activity. In another embodiment, the method involves administering a polypeptide of the invention or a nucleic acid molecule of the invention as therapy to compensate or substitute for reduced or aberrant expression or activity of the polypeptide.

Stimulation of activity is desirable in situations in which activity or expression is abnormally low or in which increased activity is likely to have a beneficial effect. Conversely, inhibition of activity is desirable in situations in which activity or expression is abnormally high or in which decreased activity is likely to have a beneficial effect.

The contents of all references, patents, and published patent applications cited in this disclosure are hereby incorporated by reference.

Deposits of Clones

Clone containing one or more cDNA molecules encoding polypeptides of the invention have been deposited with the American Type Culture Collection (ATCC®; 10801 University Boulevard, Manassas, Va. 20110-2209) on dates disclosed herein, and these deposits were assigned the Accession Numbers disclosed herein. These deposits will be maintained under the terms of the Budapest Treaty on the International Recognition of the Deposit of Microorganisms for the Purposes of Patent Procedure. These deposits were made merely as a convenience for those of skill in the art and are not an admission that any deposit is required in order to comply with 35 U.S.C. §112.

Where a clone containing multiple cDNA molecules was deposited, the following standard digest procedure can be used to liberate fragments corresponding to individual cDNA molecules, except as otherwise described. To isolate the cDNA clone, an aliquot of the deposited clone can be streaked out to yield single colonies on nutrient medium (e.g., Luria broth plates) supplemented with 100 micrograms per milliliter ampicillin. Single colonies are grown, and plasmid DNA is extracted from single colonies using a standard mini-preparation procedure. Next, a sample of the DNA mini-preparation is digested using a combination of the restriction enzymes Sal I and Not I, and the resulting products are resolved on a 0.8% (w/v) agarose gel using standard DNA electrophoresis conditions.

Clone EpT273, encoding human TANGO 273 was deposited with ATCC® on Apr. 2, 1999 and was assigned Accession Number 207185.

Clones containing cDNA molecules encoding murine TANGO 273 were deposited with ATCC® on Apr. 21, 1999 and were assigned Accession Number 207221, as part of a composite deposit representing a mixture of five strains, each carrying one recombinant plasmid harboring a particular cDNA clone. The standard digest procedure (except that restriction enzymes SalI, NotI, and ApaI are used) liberates a fragment as follows:

mouse TANGO 273 (clone EpTm273): 0.3 kilobase and 2.6 kilobase (mouse TANGO 273 has a Apa I cut site at about base pair 298).

The identity of the strain can be inferred from the fragment liberated.

Clones comprising cDNA molecules encoding human TANGO 325 were deposited with ATCC® on May 28, 1999, as part of a composite deposit representing a mixture of five strains, each carrying one recombinant plasmid harboring a particular cDNA clone. This deposit was assigned Accession Number PTA-147. The standard digest procedure (except that restriction enzymes SalI, NotI, and SmaI are used) liberates a fragment as follows:

human TANGO 325 (clone EpT325): 2.2 kilobases

The identity of the strain can be inferred from the fragment liberated.

Clones containing cDNA molecules encoding TANGO 364 (clones Aped), were deposited with ATCC® on Jul. 23, 1999 as Accession No. PTA-425, as part of a composite deposit representing a mixture of three strains, each carrying one recombinant plasmid harboring a particular cDNA clone. The standard digest procedure liberates a fragment as follows:

TANGO 364 (Aped): 3.5 kilobase pairs

The identity of the strain can be inferred from the fragment liberated.

Clones containing cDNA molecules encoding TANGO 405 (including clone 405), were deposited with ATCC® on Jul. 23, 1999 as Accession No. PTA-424, as part of a composite deposit representing a mixture of five strains, each carrying one recombinant plasmid harboring a particular cDNA clone. The standard digest procedure liberates a fragment as follows:

TANGO 405 (405): 3.1 kilobase pairs

The identity of the strain can be inferred from the fragment liberated.

Those skilled in the art will recognize, or be able to ascertain using no more than routine experimentation, many equivalents to the embodiments of the invention described herein. Such equivalents are encompassed by the following claims.

What is claimed is:

1. An isolated nucleic acid molecule selected from the group consisting of:
   a) a nucleic acid molecule comprising a nucleotide sequence which is at least 95% identical to the nucleotide sequence of any of SEQ ID NO:51, SEQ ID NO:52, or the nucleotide sequence of the clone deposited as ATCC Accession number PTA-424, wherein the nucleotide sequence encodes a polypeptide capable of mediating T-cell activation;
   b) a nucleic acid molecule which encodes a polypeptide which is at least 95% identical to the amino acid sequence of SEQ ID NO:53, wherein the polypeptide is capable of mediating T-cell activation;
   c) a nucleic acid molecule comprising the nucleotide sequence of any of SEQ ID NO:51, SEQ ID NO:52, or the nucleotide sequence of the clone deposited as ATCC Accession PTA-424, or a full complement thereof; and
   d) a nucleic acid molecule which encodes a polypeptide comprising the amino acid sequence of SEQ ID NO: 53, or the amino acid sequence encoded by the nucleotide sequence of the clone deposited as ATCC Accession number PTA-424.

2. The nucleic acid molecule of claim 1, wherein the nucleic acid molecule comprises a nucleotide sequence which is at least 95% identical to the nucleotide sequence of any of SEQ ID NO:51, SEQ ID NO:52, or the nucleotide sequence of the clone deposited as ATCC Accession number PTA-424, wherein the nucleotide sequence encodes a polypeptide capable of mediating T-cell activation.

3. The nucleic acid molecule of claim 1, wherein the nucleic acid molecule encodes a polypeptide which is at least 95% identical to the amino acid sequence of SEQ ID NO:53, wherein the polypeptide is capable of mediating T-cell activation.

4. The nucleic acid molecule of claim 1, wherein the nucleic acid molecule comprises the nucleotide sequence of any of SEQ ID NO:51, SEQ ID NO:52, or the nucleotide sequence of the clone deposited as ATCC Accession PTA-424, or a full complement thereof.

5. The nucleic acid molecule of claim 1, wherein the nucleic acid molecule encodes a polypeptide comprising the amino acid sequence of SEQ ID NO:53, or the amino acid sequence encoded by the nucleotide sequence of the clone deposited as ATCC Accession number PTA-424.

6. The nucleic acid molecule of claim 1 further comprising nucleic acid sequences encoding a heterologous polypeptide.

7. The nucleic acid molecule of claim 1, further comprising vector nucleic acid sequences.

8. An isolated non-human mammalian host cell containing the nucleic acid molecule of claim 1.

9. An isolated host cell which contains the nucleic acid molecule of claim 1.

10. The host cell of claim 9 which is a mammalian host cell.

11. A method for producing a polypeptide comprising the amino acid sequence of SEQ ID NO:53 or the amino acid sequence encoded by the nucleotide sequence of the clone deposited as ATCC Accession number PTA-424, the method comprising culturing the host cell of claim 9 under conditions in which the nucleic acid molecule is expressed.

* * * * *